(12) United States Patent
Markovitz et al.

(10) Patent No.: US 10,138,486 B2
(45) Date of Patent: Nov. 27, 2018

(54) INHIBITORS OF DEK PROTEIN AND RELATED METHODS

(71) Applicant: THE REGENTS OF THE UNIVERSITY OF MICHIGAN, Ann Arbor, MI (US)

(72) Inventors: David Markovitz, Ann Arbor, MI (US); Nirit Mor-Vaknin, Ann Arbor, MI (US); Maureen Legendre, Ann Arbor, MI (US); David Engelke, Ann Arbor, MI (US); Kristine Benford, Ann Arbor, MI (US); Dave Pai, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/557,757

(22) PCT Filed: Mar. 11, 2016

(86) PCT No.: PCT/US2016/022100
§ 371 (c)(1),
(2) Date: Sep. 12, 2017

(87) PCT Pub. No.: WO2016/145362
PCT Pub. Date: Sep. 15, 2016

(65) Prior Publication Data
US 2018/0187196 A1 Jul. 5, 2018

Related U.S. Application Data

(60) Provisional application No. 62/132,308, filed on Mar. 12, 2015.

(51) Int. Cl.
| | |
|---|---|
| A61K 31/70 | (2006.01) |
| C07H 21/02 | (2006.01) |
| C12N 15/115 | (2010.01) |
| A61K 31/713 | (2006.01) |
| A61K 45/06 | (2006.01) |
| G01N 33/53 | (2006.01) |
| A01K 67/00 | (2006.01) |

(52) U.S. Cl.
CPC .......... *C12N 15/115* (2013.01); *A61K 31/713* (2013.01); *A61K 45/06* (2013.01); *G01N 33/5308* (2013.01); *C12N 2310/16* (2013.01); *C12N 2320/31* (2013.01); *G01N 2333/46* (2013.01)

(58) Field of Classification Search
CPC ...... C12N 15/115; C12N 15/00; A61K 48/00; A61K 31/7088
See application file for complete search history.

(56) References Cited

U.S. PATENT DOCUMENTS

| | | | |
|---|---|---|---|
| 4,522,811 | A | 6/1985 | Eppstein et al. |
| 5,475,096 | A | 12/1995 | Gold et al. |
| 5,580,737 | A | 12/1996 | Polisky et al. |
| 5,660,985 | A | 8/1997 | Pieken et al. |
| 5,705,337 | A | 1/1998 | Gold et al. |
| 5,719,273 | A | 2/1998 | Tu et al. |
| 5,945,527 | A | 8/1999 | Tu et al. |
| 6,376,190 | B1 | 4/2002 | Gold et al. |
| 7,855,054 | B2 | 12/2010 | Schneider et al. |
| 7,947,447 | B2 | 5/2011 | Zichi et al. |
| 2007/0166740 | A1 | 7/2007 | Heil et al. |
| 2009/0004197 | A1 | 1/2009 | Markovitz et al. |
| 2009/0098549 | A1 | 4/2009 | Schneider et al. |
| 2011/0085980 | A1 | 4/2011 | Dugas et al. |
| 2013/0209514 | A1 | 8/2013 | Gilboa et al. |

OTHER PUBLICATIONS

Mor-Vaknin et al. DEK-targeting DNA aptamers as therapeutics for inflammatory arthritis. Nature Communications 8:14252; DOI: 10.1038/ncomms14252, pp. 1-13 (Year: 2017).*
Altschul et al., "Basic Local Alignment Search Tool" J. Mol. Biol. May 15, 1990:(215):403-410.
Broxmeyer et al. "A Role for DEK in Stem/Progenitor Cell Biology". Stem Cells. May 2013, 31(8) 1-16.
Brinkmann et al., "Neutrophil extracellular traps: is immunity the second function of chromatin?" J Cell Biol 198(5) 773-783.
Di Carlo et al., "On the composition of zymosan" Science. Apr. 4, 1958;127(3301):756-757.
Frasnelli et al, "TLR2 modulates inflammation in zymosan-induced arthritis in mice". Arthritis Res Ther. 2005;7(2):370-379.).
Gupta et al., "Rapid Histochemistry Using Slow Off-rate Modified AptamersWithAnionicCompetion" May 19, 2011 (3):273-278.
Kahlenberg et al., "Neutrophil extracellular trap-associated protein activation of the NLRP3 inflammasome is enhanced in lupus macrophages". J Immunol. 2013;190(3):1217-1226).
Kaplan et al., Neutrophil Extracellular Traps: Double-Edged swords of Innate Immunity. J Immunol 189, 2012, 2689-2695.
Kappes et al., "DEK is a poly(ADP-ribose) acceptor in apoptosis 5 and mediates resistance to genotoxic stress". Mol Cell Biol. 2008;28(10):3245-3257.
Kappes et al., "The DEK oncoprotein is a Su(var) that is essential to heterochromatin integrity". Genes Dev. 2011;25(7):673-678.

(Continued)

*Primary Examiner* — Quang Nguyen
(74) *Attorney, Agent, or Firm* — Casimir Jones, S.C.; Kirk Hogan

(57) ABSTRACT

The present invention provides methods of treatment using inhibitors of DEK protein and DEK activity. Such methods include, but are not limited to, methods of preventing, treating, and/or ameliorating inflammatory diseases, infections, autoimmune diseases, malignant diseases, and other diseases or conditions in which DEK has been implicated. Such inhibitors of DEK protein include, but are not limited to, pharmaceutical compositions including single stranded DNA or RNA aptamers capable of binding to DEK. In some embodiments, such aptamers are useful for diagnosing DEK related diseases or conditions. Related kits and compositions are further provided.

6 Claims, 43 Drawing Sheets

Specification includes a Sequence Listing.

(56) References Cited

OTHER PUBLICATIONS

Kappes et al., "Phosphorylation or Protein Kinase CK2 Changes the DNA Binding Properties of Human 20 Chromatin Protein DEK" Molecular and Cellular Biology. Jul. 2004, 24 (13)6011-6020.

Keshari et al., "Cytokines Induced Neutrophil Extracellular Traps Formation: Implication for the Inflammatory Disease Condition" PLoS ONE 7(10): 1-8.

Kessenbrock et al. "Netting neutrophils in autoimmune small-vessel vasculitis". Nat Med. 2009;15(6):623-625.

Koleva et al., "C/EBPalpha and DEK coordinately regulate myeloid differentiation". Blood Journal. May 24, 2012, 119(21): 4678-4688.

Lane et al., Stability and Kinetics of G-quadruplex Structures. Nucleic Acids Research. 2008 36(17): 5482:5515.

Lovell et al., "Interleukin-1 blockade by anakinra improves clinical symptoms in patients with neonatal-onset multisystem inflammatory disease". Arthritis & Rheumatism. Apr. 4, 2005. 52(4): 1283-1286.

Mehan et al., "Protein Signature of Lung Cancer Tissues" PLoS One, Apr. 2012 7(4)1-15.

Mor-Vaknin et al., "The DEK nuclear antigen is a secreted chemotactic factor", Mol Cell Biol Dec. 2006 26(24): 9484-9496.

Mor-Vaknin et al., "DEK in synovium of patients with juvenile idiopathic arthritis: characterization of DEK antibodies and post-translational modification of the DEK autoantigen", Arthritis Rheum. Feb. 2011 63: 556-567.

Mor-Vaknin et al., "DEK-Targeting DNA APTAMER as Novel Therapeutics for Inflammatory Arthritis" Arthritis & Rheumatology, meeting abstract 933, Sep. 29, 2015.

Nash et al., "Tumour necrosis factor inhibitors" Med J Aust. Aug. 15, 2005. 183(4): 205-208.

Needleman et al., "A General Method Applicable to the Search Similarities in the Amino Acid Squence of Two Proteins" J. Mol. Biol., 1970, 48:443.

Ostroff et al., Unlocking Biomarker Discovery: Large Scale Application of Aptamer Proteomic Technology for Early Detection of Lung Cancer PLoS One 5(12) Dec. 2010.

Pearson et al., "Improved tools for biological sequence comparision" Proc. Nat'l. Acad. Sci. USA Apr. 1988, (85) 2444-2448.

Que-Gewirth et al., "Gene therapy progress and prospects: RNA aptamers". Gene therapy. 2007;14(4):283-291.

Nimjee et al., "Aptamers: an emerging class of therapeutics". 10 Annu Rev Med. 2005;56: 555-583.

Saha et al., "Intercellular trafficking of the nuclear oncoprotein DEK". Proc Natl Acad Sci U S A. 2013;110(17):6847-6852.

Serezani et al., "Leukotrienes enhance the bactericidal activity of alveolar macrophages against Klebsiella pneumoniae through the activation of NADPH oxidase".Blood Aug. 1, 2005, 106(3)1067-1075.

Sierakowska et al.,"The putative oncoprotein DEK, part of a chimera protein associated with acute myeloid leukaemia, is an autoantigen in juvenile rheumatoid arthritis" Clin Exp Immunol,1993; 94, 435-439.

Smith et al, "Comparision of Biosequences" Adv. Appl. Math., 1981 2:482-489.

Waldmann et al., "The DEK protein—an abundant and ubiquitous constituent of mammalian chromatin", Gene 2004, 343: 1-9.

Woods et al. "IL-4 adenoviral gene therapy reduces inflammation, proinflammatory cytokines, vascularization, and bony destruction in rat adjuvant-induced arthritis". J Immunol. 2001, 166, 1214-1222.

Zhang et al., "Expression of a soluble TGF-beta receptor by tumor cells enhances dendritic cell/tumor fusion vaccine efficacy". J Immunol. 2008, 181, 3690-3697.

* cited by examiner

SEQUENCE LISTING

<160> NUMBER OF SEQ ID NOS: 6

<210> SEQ ID NO 1
<211> LENGTH: 85
<212> TYPE: DNA
<213> ORGANISM: Artificial sequence
<220> FEATURE:
<223> OTHER INFORMATION: Synthetic

<400> SEQUENCE: 1
atagggagtc gaccgaccag aagggggttaa atattcccac attgcctgcg ccagtacaaa    60
tagtatgtgc gtctacatct agact                                          85

<210> SEQ ID NO 2
<211> LENGTH: 85
<212> TYPE: DNA
<213> ORGANISM: Artificial sequence
<220> FEATURE:
<223> OTHER INFORMATION: Synthetic

<400> SEQUENCE: 2
atagggagtc gaccgaccag aataccgtgg catctggttg tagcatcacg tcttatgcgg    60
ccgtatgtgc gtctacatct agact                                          85

<210> SEQ ID NO 3
<211> LENGTH: 86
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (23)..(77)
<223> OTHER INFORMATION: n is a, c, g, t or u

<400> SEQUENCE: 3
ataggagtcg accgaccaga annnnnnnnn nnnnnnnnnn nnnnnnnnnn nnnnnnnnnn    60
ntatgtgcgt ctacatctag actcat                                         86

<210> SEQ ID NO 4
<211> LENGTH: 21
<212> TYPE: DNA
<213> ORGANISM: Artificial sequence
<220> FEATURE:
<223> OTHER INFORMATION: Synthetic

<400> SEQUENCE: 4
ataggagtcg accgaccaga a                                              21

<210> SEQ ID NO 5
<211> LENGTH: 25
<212> TYPE: DNA
<213> ORGANISM: Artificial sequence
<220> FEATURE:
<223> OTHER INFORMATION: Synthetic

<400> SEQUENCE: 5
atgagtctag atgtagacgc acata                                          25

<210> SEQ ID NO 6
<211> LENGTH: 41

```
<212> TYPE: DNA
<213> ORGANISM: Artificial sequence
<220> FEATURE:
<223> OTHER INFORMATION: Synthetic

<400> SEQUENCE: 6
ggggttaaat attcccacat tgcctgcgcc agtacaaata g                              41
```

INHIBITORS OF DEK PROTEIN AND RELATED METHODS

CROSS-REFERENCE TO RELATED APPLICATIONS

The present Application claims priority to U.S. Provisional Application Ser. No. 62/132,308 filed Mar. 12, 2015, the entirety of which is incorporated by reference herein.

STATEMENT REGARDING FEDERALLY SPONSORED RESEARCH OR DEVELOPMENT

This invention was made with government support under R01 AI062248, R01 AI062248, R03 AR056748-01, and K01 AR055620 awarded by the National Institute of Health. The government has certain rights in the invention.

FIELD OF THE INVENTION

Provided herein are methods of treatment using inhibitors of DEK protein and DEK activity. Such methods include, but are not limited to, methods of preventing, treating, and/or ameliorating inflammatory diseases, infections, autoimmune diseases, malignant diseases, and other diseases or conditions in which DEK has been implicated. Such inhibitors of DEK protein include, but are not limited to, pharmaceutical compositions including single stranded DNA or RNA aptamers capable of binding to DEK. In some embodiments, such aptamers are useful for diagnosing DEK related diseases or conditions. Related kits and compositions are further provided.

BACKGROUND OF THE INVENTION

Tissue inflammatory responses participate in the pathogenesis of a diversity of conditions, syndromes and disorders including, for example, arthritis and ocular inflammation. An important mediator of inflammation is the DEK protein, an abundant and ubiquitous chromatin protein in multicellular organisms. DEK comprises two DNA binding modules of which one includes a SAP box, a sequence motif that DEK shares with other chromatin proteins. DEK has no apparent affinity to specific DNA sequences, but preferentially binds to super-helical and cruciform DNA, and induces positive supercoils into closed circular DNA (Waldmann T. et al., "The DEK protein—an abundant and ubiquitous constituent of mammalian chromatin", Gene 343: 1-9, 2004.). DEK has recently been found to play a significant role in inflammatory diseases like arthritis (Mor-Vaknin N. et al., "DEK in synovium of patients with juvenile idiopathic arthritis: characterization of DEK antibodies and posttranslational modification of the DEK autoantigen", Arthritis Rheum. 63: 556-567, 2011, Mor-Vanknin H. et al., "The DEK nuclear antigen is a secreted chemotactic factor", Mol Cell Biol 26: 9484-9496, 2006.). Because of the structural motifs of DEK, DEK is not a favorable candidate for traditional small-molecule drug discovery.

Improved methods for treating DEK-mediated arthritis and inflammatory disorders are needed.

SUMMARY OF THE INVENTION

Provided herein are aptamers that bind to DEK, and compositions comprising aptamers that bind to DEK. Aptamers are oligonucleotides that bind their targets with high affinity and specificity. Aptamers may be selected using the SELEX (systematic evolution of ligands by exponential enrichment) method. In some instances, base modifications may mediate hydrophobic interactions between the aptamer and target, leading to significant improvement in binding affinity. The disclosed aptamers are useful as therapeutics for preventing, treating, and/or ameliorating inflammatory diseases, malignant diseases, infections, autoimmune diseases, and/or other diseases or conditions in which DEK is implicated. The aptamers also find use in research, drug screening, and other applications. Also provided herein are pharmaceutical compositions or formulations comprising a DEK aptamer, or a pharmaceutically acceptable salt thereof, and at least one pharmaceutically acceptable carrier. Such compositions can be prepared in any suitable pharmaceutically acceptable dosage form.

In experiments conducted during the course of developing embodiments of the present invention, single stranded DNA aptamers that bind and inhibit DEK with high specificity and affinity, and that block its inflammatory effects, have been identified.

In some embodiments, provided herein are methods of treating, ameliorating, or preventing recurrence of an inflammatory condition in a patient, comprising administering to a patient (e.g., a human patient) a therapeutically effective amount of a DEK aptamer, and a pharmaceutically acceptable carrier. In certain embodiments, the DEK aptamer is a DNA aptamer. In further embodiments, the DNA aptamer comprises or consists of 18 to 200 nucleotides, or 18 to 150 nucleotides, or 18 to 100 nucleotides, or 18 to 75 nucleotides, or 18 to 50 nucleotides, or 20 to 150 nucleotides, or 20 to 100 nucleotides, or 20 to 75 nucleotides, or 20 to 50 nucleotides, wherein each nucleotide may, independently, be a modified or unmodified nucleotide. In further embodiments, the DNA aptamer comprises or is SEQ ID NO: 1, SEQ ID NO: 2 or SEQ ID NO: 6. In particular embodiments, the inflammatory condition is one or more conditions selected from arthritis, rheumatoid arthritis, juvenile rheumatoid arthritis, and inflammatory disease or an autoimmune disease. In specific embodiments, the patient is a human patient and the DEK is human DEK. Some embodiments further comprise administering to a patient one or more anti-inflammatory agents. In other embodiments, the anti-inflammatory agent is a steroidal anti-inflammatory agent. In still other embodiments, the anti-inflammatory agent is a non-steroidal anti-inflammatory agent.

In some embodiments, provided herein are kits comprising a pharmaceutical composition comprising a DEK aptamer, and, optionally, instructions for administering the pharmaceutical composition to a patient diagnosed with arthritis, rheumatoid arthritis, juvenile rheumatoid arthritis, and uveitis. In other embodiments, the kit comprises one or more anti-inflammatory agents. In certain embodiments, the pharmaceutical composition is to be administered together with one or more other anti-inflammatory agents. In preferred embodiments, the DEK aptamer is selected from the group consisting of SEQ ID NO: 1, SEQ ID NO: 2 or SEQ ID NO: 6.

In some embodiments, provided herein are methods of inhibiting signs of inflammation, comprising exposing to a sample comprising inflammatory cells a composition comprising an anti-DEK aptamer, wherein said exposing results in inhibition of signs of inflammation. In some embodiments, the DEK aptamer is SEQ ID NO: 1, SEQ ID NO: 2 or SEQ ID NO: 6. In some embodiments, the sample is from a human. In certain embodiments, the human is diagnosed with arthritis, rheumatoid arthritis or juvenile rheumatoid arthritis.

In some embodiments, provided herein are methods of detecting DEK in a sample, comprising contacting proteins from a sample with a DEK aptamer. In certain embodiments, the sample is a human sample selected from the group consisting of a blood sample, a serum sample, a plasma sample, a saliva sample, a urine sample, a synovial fluid sample, a cartilage sample, and a tissue sample.

In some embodiments, provided herein are compositions comprising an aptamer that specifically binds to DEK. In certain embodiments the aptamer is selected from the group consisting of SEQ ID NO: 1, SEQ ID NO: 2 or SEQ ID NO: 6. In further embodiments, the aptamer comprises at least one modified pyrimidine. In still further embodiments the modified aptamer is an aromatic modified aptamer. In other embodiments, the aptamer comprises 2 to 6 modified pyrimidines.

In some embodiments, provided herein are pharmaceutical compositions comprising at least one DEK aptamer, or a pharmaceutically acceptable salt thereof, and a pharmaceutically acceptable carrier.

Methods and pharmaceutical compositions or formulations for preventing, treating, and/or ameliorating a disease or condition mediated by DEK are provided. In some embodiments, a method comprises administering a DEK aptamer, or pharmaceutical compositions or formulations comprising a DEK aptamer, to a subject, such as a mammal. In some embodiments, the subject is a human.

In some embodiments, methods and pharmaceutical compositions or formulations are provided for preventing, treating, and/or ameliorating inflammatory diseases, malignant diseases, infections, autoimmune diseases, and/or other diseases or conditions in which DEK is implicated. Non-limiting exemplary inflammatory diseases that may be treated with the DEK aptamers described herein include rheumatoid arthritis, juvenile idiopathic arthritis, systemic-onset juvenile idiopathic arthritis, osteoarthritis, uveitis, gout, sepsis, asthma, interstitial lung disease, inflammatory bowel disease, systemic sclerosis, intraocular inflammation, Grave's disease, endometriosis, systemic sclerosis, adult-onset still disease, amyloid A amyloidosis, polymyalgia rheumatic, remitting seronegative symmetrical synovitis with pitting edema, Behcet's disease, uveitis, graft-versus-host diseases, and TNFR-associated periodic syndrome.

Malignant diseases that may be treated with the DEK aptamers described herein include cancers and cancer-related conditions. Non-limiting exemplary cancers include multiple myeloma, leukemia, pancreatic cancer, breast cancer, colorectal cancer, cachexia, melanoma, cervical cancer, ovarian cancer, lymphoma, gastrointestinal, lung cancer, prostate cancer, renal cell carcinoma, metastatic kidney cancer, solid tumors, non-small cell lung carcinoma, non-Hodgkin's lymphoma, bladder cancer, oral cancer, myeloproliferative neoplasm, B-cell lymphoproliferative disease, and plasma cell leukemia. Non-limiting exemplary cancer-related conditions include non-small cell lung cancer-related fatigue and cancer related anorexia.

Non-limiting exemplary infections that may be treated with the DEK aptamers described herein include human immunodeficiency virus (HIV), human T-lymphotropic virus (HTLV), cerebral malaria, urinary tract infections, and meningococcal infections.

Non-limiting exemplary autoimmune diseases that may be treated with the DEK aptamers described herein include systemic lupus erythromatosus, systemic sclerosis, polymyositis, vasculitis syndrome including giant cell arteritis, takayasu aeteritis, cryoglobulinemia, myeloperoxidase-antineutrophilcytoplasmic antibody-associated crescentic glomerulonephritis, rheumatoid vasculitis, Crohn's disease, relapsing polychondritis, acquired hemophilia A, and autoimmune hemolytic anemia.

Further diseases that may be treated with the DEK aptamers described herein include, but are not limited to, Castleman's disease, ankylosing spondyliytis, coronary heart disease, cardiovascular disease in rheumatoid arthritis, pulmonary arterial hypertension, chronic obstructive pulmonary disease (COPD), atopic dermatitis, psoriasis, sciatica, type II diabetes, obesity, giant cell arteritis, acute graft-versus-host disease (GVHD), non-ST elevation myocardial infarction, anti-neutrophil cytoplasmic antibody (ANCA) associated vasculitis, neuromyelitis optica, chronic glomerulonephritis, and Takayasu arteritis.

In some embodiments, aptamers disclosed herein have applications ranging from biomarker discovery and diagnostics (Ostroff, R. M., et al., PLoS One, 2010. 5(12): p. e15003; Mehan, M., et al., PLoS One, 2012.) to histochemistry and imaging (Gupta, S., et al., Appl Immunohistochem Mol Morphol, 2011. 19(3): p. 273-8).

In some embodiments, a therapeutic effect (e.g., treating, preventing, and/or ameliorating inflammatory diseases, malignant diseases, infections, autoimmune diseases, and other diseases or conditions in which DEK has been implicated) may be achieved by administering at least one DEK aptamer such that the aptamer is exposed to, and can bind to, DEK. In some embodiments, such binding occurs regardless of the method of delivery of the aptamer to the subject being treated. In some embodiments, the therapeutic effect may be achieved by administering at least one DEK aptamer such that it is exposed to, and binds to, DEK and prevents or reduces the binding of DEK to one or more cell receptors.

In some embodiments, the binding of a DEK aptamer to DEK interferes with the binding of DEK to a DEK receptor. In some embodiments, a DEK aptamer reduces signaling along the signal transduction pathway of a DEK receptor.

In some embodiments, a DEK aptamer is administered with one or more additional active agents. Such administration may be sequential or in combination. Non-limiting exemplary additional active agents include TNF-alpha inhibitors, IL-1 inhibitors, IL-23 inhibitors, IFN-gamma inhibitors, IL-17 inhibitors, IL-22 inhibitors, IL-4/IL-13 inhibitors, IL-13 inhibitors, IL-5 inhibitors, and JAK inhibitors.

In certain embodiments, provided herein are methods for treating, ameliorating, or preventing recurrence of a condition involving inflammation in a patient (e.g., a human patient) comprising administering to the patient a therapeutically effective amount of a DEK aptamer, including salts, esters and prodrugs thereof, and pharmaceutically acceptable carrier. Such methods are not limited to a particular DEK aptamer. In some embodiments, the DEK aptamer upon administration to the patient does not induce a cytokine response, an inflammatory response, and/or systemic toxicity in the patient. In certain embodiments, the present invention provides kits comprising a pharmaceutical composition comprising a DEK aptamer and instructions for administering the pharmaceutical composition to a patient (e.g., a human patient) an inflammatory or autoimmune disorder. In some embodiments, the kits further comprise one or more anti-inflammatory agents.

In some embodiments, an in vitro or in vivo diagnostic method comprising contacting a DEK aptamer with a sample suspected of comprising DEK is provided. In some embodiments, an in vivo diagnostic method comprising administering a suitably labeled DEK aptamer to an individual suspected of having a DEK-mediated disease or disorder is provided, wherein the labeled aptamer is detected for the purpose of diagnosing or evaluating the health status of the individual. The label used may be selected in accordance with the imaging modality to be used. In some embodiments, a diagnostic kit or device comprising a DEK aptamer is provided. In some embodiments, a DEK aptamer that specifically binds DEK is provided.

In some embodiments, aptamers comprise one or more of a linker, a modified nucleotide, an unmodified nucleotide, an aromatic modified pyrimidine, an alkylene glycol, a polyalkylene glycol, a substituted or unsubstituted $C_2$-$C_{20}$ linker, a 1,3-propane diol, a poly(1,3-propane diol) having from 2 to 100 1,3-propane diol units, an ethylene glycol, and a polyethylene glycol having from 2 to 100 ethylene glycol units, In certain embodiments, each substituted or unsubstituted $C_2$-$C_{20}$ linker is a substituted or unsubstituted $C_2$-$C_8$ linker, a substituted or unsubstituted $C_2$-$C_6$ linker, a substituted or unsubstituted $C_2$-$C_5$ linker, a substituted or unsubstituted $C_2$-$C_4$ linker, or a substituted or unsubstituted $C_3$ linker.

In some embodiments, an aptamer comprises a G quartet motif. In certain embodiments described herein, an aptamer may comprise at least one modified pyrimidine.

In particular embodiments, each modified pyrimidine may be independently selected from: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-tyrosylcarboxyamide)-2'-deoxyuridine (TyrdU), 5-(N-3,4-methylenedioxybenzylcarboxyamide)-2'-deoxyuridine (MBndU), 5-(N-4-fluorobenzylcarboxyamide)-2'-deoxyuridine (FBndU), 5-(N-3-phenylpropylcarboxyamide)-2'-deoxyuridine (PPdU), 5-(N-imidizolylethylcarboxyamide)-2'-deoxyuridine (ImdU), 5-(N-isobutylcarboxyamide)-2'-O-methyluridine, 5-(N-isobutylcarboxyamide) -2'-fluorouridine, 5-(N-tryptaminocarboxyamide)-2'-deoxyuridine (TrpdU), 5-(N—R-threoninylcarboxyamide)-2'-deoxyuridine (ThrdU), 5-(N-tryptaminocarboxyamide)-2'-O-methyluridine, 5-(N-tryptaminocarboxyamide)-2'-fluorouridine, 5-(N-[1-(3-trimethylamonium)propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethyl carboxyamide)-2'-fluorouridine, 5-(N-[1-(2,3-dihydroxypropyl)]carboxyamide)-2'-deoxyuridine), 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine.

In further embodiments, aptamers comprise one or more of 5-(N-1-naphthylmethylcarboxyamide)-2'-deoxyuridine (NapdU), 5-(N-1-naphthylmethylcarboxyamide)-2'-O-methyluridine, 5-(N-1-naphthylmethylcarboxyamide)-2'-fluorouridine, 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine.

In some embodiments, the aptamer comprises at least 2 to 6 modified pyrimidines and/or a 2'-OMe. In certain embodiments, an aptamer may comprise at least one, or at least 2 to 5 phosphorothioate linkages.

In some embodiments, a pharmaceutical composition is provided that comprises any of the aptamers described herein, or pharmaceutically acceptable salt thereof, and a pharmaceutically acceptable carrier. In some embodiments, the pharmaceutical composition is for treating a disease or condition mediated by DEK.

In some embodiments, an aptamer that binds DEK with an affinity of less than 10 nM is provided. In some embodiments, the aptamer binds DEK 1 with an affinity of less than 10 nM. In some embodiments, the aptamer binds DEK with an affinity of less than 8 nM, or less than 7 nM, or less than 6 nM, or less than 5 nM, or less than 4 nM, or less than 3 nM, or less than 2 nM, or less than 1 nM.

In embodiments described herein, the aptamer may consist of 18 to 200 nucleotides, or 18 to 150 nucleotides, or 18 to 100 nucleotides, or 18 to 75 nucleotides, or 18 to 50 nucleotides, or 20 to 150 nucleotides, or 20 to 100 nucleotides, or 20 to 75 nucleotides, or 20 to 50 nucleotides, wherein each nucleotide may, independently, be a modified or unmodified nucleotide. In embodiments described herein, the aptamer may comprise a detectable label.

In some embodiments, a method of detecting DEK in a sample is provided, comprising contacting proteins from a sample with an aptamer described herein. In some embodiments, a method of determining whether a sample comprises DEK, comprises contacting proteins from the sample with an aptamer described herein. In some embodiments, the method comprises contacting the sample with the aptamer under stringent conditions.

In some embodiments, the sample is a sample from a human. In some embodiments, the sample is selected from blood, serum, plasma, saliva, urine, synovial fluid, cartilage and a tissue sample.

The foregoing and other objects, features, and advantages of the invention will become more apparent from the following detailed description, which proceeds with reference to the accompanying figures.

DEFINITIONS AND METHODS

Figure 1:
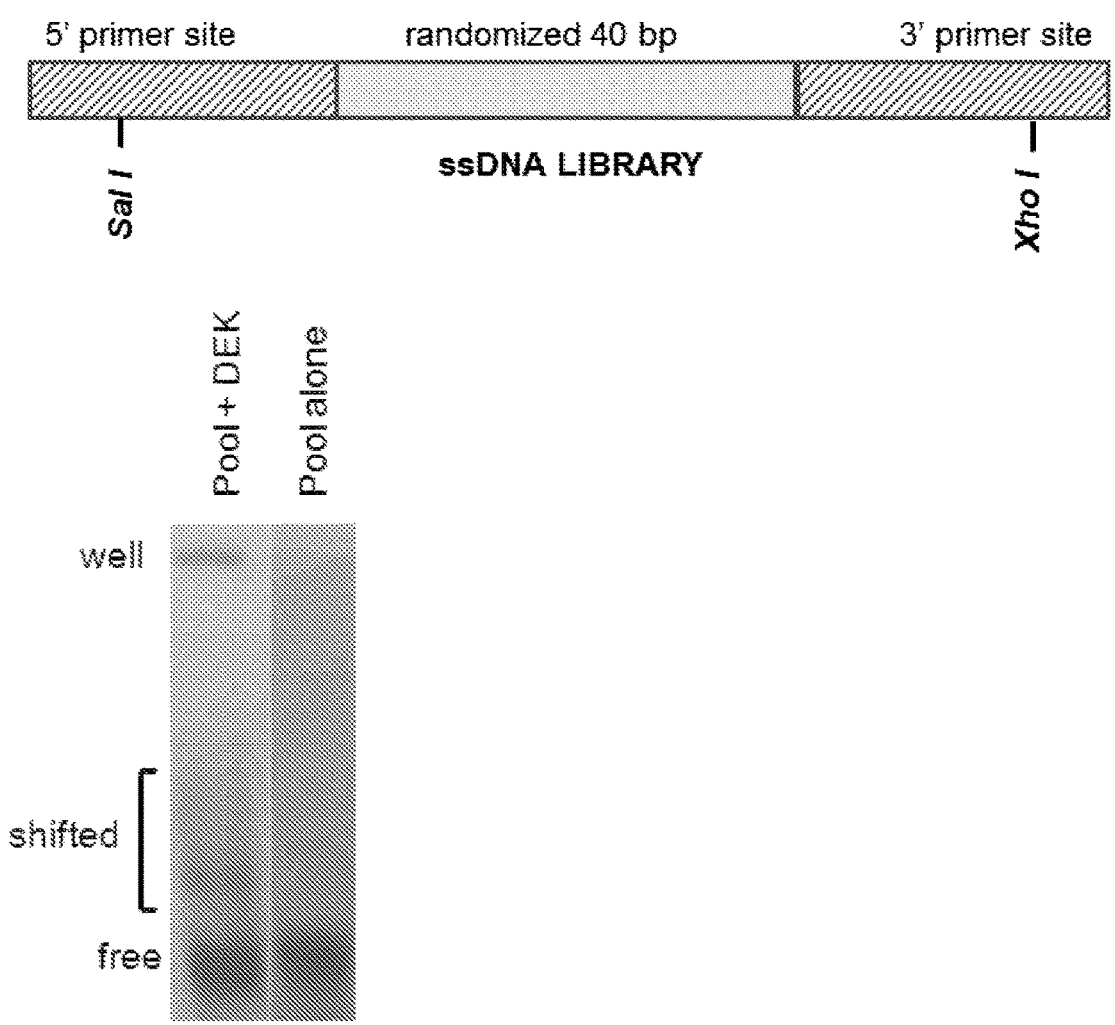
FIG. 1: Shows a DNA oligomer containing 40 central nucleotides of sequence flanked by defined primer-binding sites.

While the invention will be described in conjunction with certain representative embodiments, it will be understood that the invention is not limited to these illustrative examples. One skilled in the art will recognize many methods and materials similar or equivalent to those described herein may be used in the practice of the present invention. The present invention is in no way limited to the methods and materials described.

Unless defined otherwise, technical and scientific terms used herein have the meaning commonly understood by one of ordinary skill in the art to which this invention belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Although any methods, devices, and materials similar or equivalent to those described herein can be used in the practice of the invention, certain methods, devices, and materials are described herein. It is further to be understood that all base sizes or amino acid sizes, and all molecular weight or molecular mass values, given for nucleic acids or polypeptides are approximate, and are provided for description.

Unless defined otherwise, technical and scientific terms used herein have the same meaning as commonly understood by one of ordinary skill in the art(s) to which this invention belongs. Although any methods, devices, and materials similar or equivalent to those described herein can be used in the practice or testing of the invention, the preferred methods, devices and materials are now described.

As used in this disclosure, including the appended claims, the singular forms "a," "an," and "the" include plural references, unless the content clearly dictates otherwise, and are used interchangeably with "at least one" and "one or more." Thus, reference to "an aptamer" includes mixtures of aptamers, and the like.

As used herein, the term "about" represents an insignificant modification or variation of the numerical value such that the basic function of the item to which the numerical value relates is unchanged.

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs). When a base is indicated as "A", "C", "G", "U", or "T", it is intended to encompass both ribonucleotides and deoxyribonucleoties, and modified forms and analogs thereof.

As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included.

The terms "polynucleotide," "oligonucleotide," and "nucleic acid" include double- or single-stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers but the terms nucleic acid, oligonucleotide, and polynucleotide are not limited to aptamers.

As used herein, the terms "modify", "modified", "modification", and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. In some embodiments, the modified nucleotides lead to predominantly hydrophobic interactions of aptamers with protein targets resulting in high binding efficiency and stable co-crystal complexes. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers, in some embodiments, ranging from about 10 to about 80 kDa, PEG polymers, in some embodiments, ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

As used herein, the term "nuclease" refers to an enzyme capable of cleaving the phosphodiester bond between nucleotide subunits of an oligonucleotide. As used herein, the term "endonuclease" refers to an enzyme that cleaves phosphodiester bond(s) at a site internal to the oligonucleotide. As used herein, the term "exonuclease" refers to an enzyme which cleaves phosphodiester bond(s) linking the end nucleotides of an oligonucleotide. Biological fluids typically contain a mixture of both endonucleases and exonucleases.

As used herein, the terms "nuclease resistant" and "nuclease resistance" refers to the reduced ability of an oligonucleotide to serve as a substrate for an endo- or exonuclease, such that, when contacted with such an enzyme, the oligonucleotide is either not degraded (e.g., not detectably degraded) or is degraded more slowly than an oligonucleotide composed of unmodified nucleotides.

As used herein, the term "C-5 modified pyrimidine" refers to a pyrimidine with a modification at the C-5 position. Examples of a C-5 modified pyrimidine include those described in U.S. Pat. Nos. 5,719,273 and 5,945,527. Examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), phenethylcarboxyamide (alternatively phenethylamino carbonyl) (Pe), thiophenylmethylcarboxyamide (alternatively thiophenylmethylaminocarbonyl) (Th) and isobutylcarboxyamide (alternatively isobutylaminocarbonyl) (iBu).

Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-O-methyluridine, 5-(N-phenethylcarboxyamide)-2'-deoxyuridine (PedU), 5-(N-thiophenylmethylcarboxyamide)-2'-deoxyuridine (ThdU), 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium)propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine or 5-(N-[1-(2,3-dihydroxypropyl)]carboxyamide)-2'-deoxyuridine).

Nucleotides can be modified either before or after synthesis of an oligonucleotide. A sequence of nucleotides in an oligonucleotide may be interrupted by one or more non-nucleotide components. A modified oligonucleotide may be further modified after polymerization, such as, for example, by conjugation with any suitable labeling component. As used herein, the term "at least one pyrimidine," when referring to modifications of a nucleic acid, refers to one, several, or all pyrimidines in the nucleic acid, indicating that any or all occurrences of any or all of C, T, or U in a nucleic acid may be modified or not.

As used herein, "nucleic acid ligand," "aptamer," and "clone" are used interchangeably to refer to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In one embodiment, the action is specific binding affinity for a target molecule, such target molecule being a three dimensional chemical structure other than a polynucleotide that binds to the nucleic acid ligand through a mechanism which is independent of Watson/Crick base pairing or triple helix formation, wherein the aptamer is not a nucleic acid having the known physiological function of being bound by the target molecule. As used herein, an "aptamer" refers to a nucleic acid that has a specific binding affinity for a target molecule (see e.g., Nimjee S M, Rusconi C P, Sullenger B A. "Aptamers: an emerging class of therapeutics". Annu Rev Med. 2005; 56:555-583. Que-Gewirth N S, Sullenger B A. "Gene therapy progress and prospects: RNA aptamers". Gene therapy. 2007; 14(4):283-291.). It is recognized that affinity interactions are a matter of degree. However, in this context, the "specific binding affinity" of an aptamer for its target means that the aptamer binds to its target generally with a much higher degree of affinity than it binds to other components in a test sample. An "aptamer" is a set of copies of one type or species of nucleic acid molecule that has a particular nucleotide sequence. An aptamer can include any suitable number of nucleotides, including any number of chemically modified nucleotides. "Aptamers" refers to more than one such set of molecules. Different aptamers can have either the same or different numbers of nucleotides. Any of the aptamer methods disclosed herein can include the use of two or more aptamers that specifically bind the same target molecule. An aptamer can be identified using any known method, including the SELEX process (see below). Once identified, an aptamer can be prepared or synthesized in accordance with any known method, including chemical synthetic methods and enzymatic synthetic methods. DEK aptamer, or anti-DEK aptamer, as used herein, refers to an aptamer that specifically binds to a mature DEK protein.

Aptamers to a given target include nucleic acids that are identified from a candidate mixture of nucleic acids, where the aptamer is a ligand of the target, by a method comprising: (a) contacting the candidate mixture with the target, wherein nucleic acids having an increased affinity to the target relative to other nucleic acids in the candidate mixture are partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby aptamers of the target molecule are identified. Aptamers may be DNA or RNA and may be single stranded, double stranded, or contain double stranded or triple stranded regions. Aptamers can comprise chemically modified nucleic acids and can include higher ordered structures.

As used here, a "G quartet" is a nucleotide sequence motif that comprises four pairs of G nucleotides with at least one nucleotide or spacer group between each pair of G nucleotides. G quartet motifs are described, e.g., in Lane, A. N., et al., NAR, 2008. 36(17): 5482:5515.

As used herein, "protein" is used synonymously with "peptide," "polypeptide," or "peptide fragment." A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "inflammatory disease" refers to a disease or condition involving an inflammatory response. The inflammatory response may be acute and/or chronic. In some embodiments, chronic inflammation involves an increase in the level of DEK. Non-limiting exemplary inflammatory diseases that may be treated with the DEK aptamers described herein include rheumatoid arthritis, juvenile idiopathic arthritis, systemic-onset juvenile idiopathic arthritis, osteoarthritis, sepsis, asthma, interstitial lung disease, inflammatory bowel disease, systemic sclerosis, intraocular inflammation, Grave's disease, endometriosis, systemic sclerosis, adult-onset still disease, amyloid A amyloidosis, polymyalgia rheumatic, remitting seronegative symmetrical synovitis with pitting edema, Behcet's disease, uveitis, graft-versus-host diseases, and TNFR-associated periodic syndrome.

As used herein, "malignant disease" includes cancer and cancer-related conditions.

As used herein, "cancer" means a disease or condition involving unregulated and abnormal cell growth. Non-limiting exemplary cancers that may be treated with the DEK aptamers described herein include multiple myeloma, leukemia, pancreatic cancer, breast cancer, colorectal cancer, cachexia, melanoma, cervical cancer, ovarian cancer, lymphoma, gastrointestinal, lung cancer, prostate cancer, renal cell carcinoma, metastatic kidney cancer, solid tumors, non-small cell lung carcinoma, non-Hodgkin's lymphoma, bladder cancer, oral cancer, myeloproliferative neoplasm, B-cell lymphoproliferative disease, and plasma cell leukemia. Non-limiting exemplary cancer-related conditions include non-small cell lung cancer-related fatigue and cancer related anorexia.

As used herein, "infection" refers to a disease or condition caused by a pathogen, such as a bacteria, virus, fungus, etc. Non-limiting exemplary infections that may be treated with the DEK aptamers described herein include human immunodeficiency virus (HIV), human T-lymphotropic virus (HTLV), cerebral malaria, urinary tract infections, and meningococcal infections.

As used herein, "autoimmune disease" refers to a disease or condition arising from an inappropriate immune response against the body's own components, such as tissues and other components. In some embodiments, DEK levels are elevated in autoimmune disease. Non-limiting exemplary autoimmune diseases that may be treated with the DEK aptamers described herein include systemic lupus erythromatosus, systemic sclerosis, polymyositis, vasculitis syndrome including giant cell arteritis, takayasu aeteritis, cryoglobulinemia, myeloperoxidase-antineutrophilcytoplasmic antibody-associated crescentic glomerulonephritis, rheumatoid vasculitis, Crohn's disease, relapsing polychondritis, acquired hemophilia A, and autoimmune hemolytic anemia.

As used herein, a "DEK mediated disease or condition" refers to a disease or condition in which at least some of the symptoms and/or progression of the disease or condition is caused by DEK-mediated signaling. Non-limiting exemplary DEK mediated diseases or conditions include inflammatory diseases, malignant diseases (including cancer and cancer-related conditions), infections, and autoimmune diseases. Further non-limiting exemplary DEK mediated diseases include, but are not limited to, Castleman's disease, ankylosing spondyliytis, coronary heart disease, cardiovascular disease in rheumatoid arthritis, pulmonary arterial hypertension, chronic obstructive pulmonary disease (COPD), atopic dermatitis, psoriasis, sciatica, type II diabetes, obesity, giant cell arteritis, acute graft-versus-host disease (GVHD), non-ST elevation myocardial infarction, anti-neutrophil cytoplasmic antibody (ANCA) associated vasculitis, neuromyelitis optica, chronic glomerulonephritis, and Takayasu arteritis.

As used herein, "modulate" means to alter, either by increasing or decreasing, the level of a peptide or polypeptide, or to alter, either by increasing or decreasing, the stability or activity of a peptide or a polypeptide. The term "inhibit", as used herein, means to prevent or reduce the expression of a peptide or a polypeptide to an extent that the peptide or polypeptide no longer has measurable activity or bioactivity; or to reduce the stability and/or reduce or prevent the activity of a peptide or a polypeptide to an extent that the peptide or polypeptide no longer has measurable activity or bioactivity. As described herein, the protein which is modulated or inhibited is DEK.

As used herein, the term "bioactivity" indicates an effect on one or more cellular or extracellular process (e.g., via binding, signaling, etc.) which can impact physiological or pathophysiological processes. As used herein, the terms "DEK" refer to naturally-occurring DEK, including naturally-occurring isoforms and variants. As used herein, DEK includes all mammalian species of DEK, including human, canine, feline, murine, primate, equine, and bovine.

As used herein, "DEK receptor" refers to a receptor that is bound by and activated by DEK. DEK receptors include the receptors of any mammalian species, including, but are not limited to, human, canine, feline, murine, equine, primate, and bovine.

A "DEK aptamer" is an aptamer that specifically binds to and modifies the activity of DEK. In some embodiments, a DEK aptamer inhibits at least one activity of DEK in vitro. In some embodiments, a DEK aptamer inhibits at least one activity of DEK in vivo. Non-limiting exemplary activities of DEK include binding to a DEK receptor, and meditating inflammation.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to, such sterile liquids as water and oils.

A "pharmaceutically acceptable salt" or "salt" of a DEK aptamer is a product of the disclosed compound that contains an ionic bond and is typically produced by reacting the disclosed compound with either an acid or a base, suitable for administering to an individual. A pharmaceutically acceptable salt can include, but is not limited to, acid addition salts including hydrochlorides, hydrobromides, phosphates, sulphates, hydrogen sulphates, alkyl sulphonates, aryl sulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising a DEK aptamer in a form suitable for administration to an individual. A pharmaceutical composition is typically formulated to be compatible with its intended route of administration. Examples of routes of administration include, but are not limited to, oral and parenteral, e.g., intravenous, intradermal, subcutaneous, inhalation, topical, transdermal, transmucosal, intra-articular, intra-ocular, and rectal administration.

As used herein, the term "therapeutically effective amount" generally means the amount necessary to ameliorate at least one symptom of a disorder or condition to be prevented, reduced, or treated as described herein. The phrase "therapeutically effective amount" as it relates to the DEK aptamers of the present disclosure means the aptamer dosage that provides the specific pharmacological response for which the aptamer is administered in a significant number of individuals in need of such treatment. It is emphasized that a therapeutically effective amount of an aptamer that is administered to a particular individual in a particular instance will not always be effective in treating the conditions/diseases described herein, even though such dosage is deemed to be a therapeutically effective amount by those of skill in the art.

The terms "SELEX" and "SELEX process" are used interchangeably herein to refer generally to a combination of (1) the selection of nucleic acids that interact with a target molecule in a desirable manner, for example, binding with high affinity to a protein, with (2) the amplification of those selected nucleic acids. The SELEX process can be used to identify aptamers with high affinity to a specific target molecule. SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. (See, e.g., U.S. Pat. No. 5,475,096, entitled "Nucleic Acid Ligands.") The SELEX process can be used to generate an aptamer that covalently binds its target as well as an aptamer that non-covalently binds its target. (See, e.g., U.S. Pat. No. 5,705,337 entitled "Systematic Evolution of Nucleic Acid Ligands by Exponential Enrichment: Chemi-SELEX.")

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the C5 and/or 2'-positions of pyrimidines. U.S. Pat. No. 5,580,737, see supra, describes highly specific aptamers containing one or more nucleotides modified with 2'-amino (2'-$NH_2$), 2'-fluoro (2'-F), and/or 2'-O-methyl (2'-OMe). See also, U.S. Patent Application Publication No. 20090098549, entitled "SELEX and PHOTOSELEX," which describes nucleic acid libraries having expanded physical and chemical properties and their use in SELEX and photoSELEX.

In some embodiments, provided herein are methods for producing oligonucleotides with improved nuclease resistance. The nuclease resistant oligonucleotides may include at least one pyrimidine modified at the C-5 position. In certain embodiments, the modifications include substitution of deoxyuridine at the C-5 position with a substituent independently selected from: benzylcarboxyamide (Bn), phenethyl (Pe), thiophenylmethyl (Th), naphthylmethylcarboxyamide (Nap), tryptaminocarboxyamide (Trp), and isobutylcarboxyamide as illustrated above.

As used herein a "linker" is a molecular entity that connects two or more molecular entities through covalent bond or non-covalent interactions, and can allow spatial separation of the molecular entities in a manner that preserves the functional properties of one or more of the molecular entities. A linker can also be known as a spacer. Appropriate linker sequences will be readily ascertained by those of skill in the art based upon the present disclosure.

As used herein, a linker can comprise one or more molecules or sub-components, selected from the group including, but not limited to a polynucleotide, a polypeptide, a peptide nucleic acid, a locked nucleic acid, an oligosaccharide, a polysaccharide, an antibody, an affybody, an antibody mimic, an aliphatic, aromatic or heteroaromatic carbon molecule, alkylene glycol (e.g., ethylene glycol, 1,3-propane diol), a polyalkylene glycol (e.g., polyethylene glycol (PEG)), a cell receptor, a ligand, a lipid, any fragment or derivative of these structures, any combination of the foregoing, or any other chemical structure or component.

In some embodiments, as used herein a linker or spacer may be a backbone comprising a chain of 2 to 20 carbon atoms ($C_2$-$C_{20}$) (saturated, unsaturated, straight chain, branched or cyclic), 0 to 10 aryl groups, 0 to 10 heteroaryl groups, and 0 to 10 heterocyclic groups, optionally comprising an ether (—O—) linkage, (e.g., one or more alkylene glycol units, including but not limited to one or more ethylene glycol units —O—($CH_2CH_2O$)—; one or more 1,3-propane diol units -O—($CH_2CH_2CH_2O$)—, etc.; in some embodiments, a linker comprises 1 to 100 units, 1 to 50 units, 1 to 40 units, 1 to 30 units, 1 to 20 units, 1 to 12 units, or 1 to 10 units); an amine (—NH—) linkage; an amide (—NC(O)—) linkage; and a thioether (—S—) linkage; etc.; wherein each backbone carbon atom may be independently unsubstituted (i.e., comprising —H substituents) or may be substituted with one or more groups selected from a $C_1$ to $C_3$ alkyl, —OH, —$NH_2$, —SH, —O—($C_1$ to $C_6$ alkyl), —S—($C_1$ to $C_6$ alkyl), halogen, —OC(O)($C_1$ to $C_6$ alkyl), —NH—($C_1$ to $C_6$ alkyl), and the like. In some embodiments, a $C_2$-$C_{20}$ linker is a $C_2$-$C_8$ linker, a $C_2$-$C_6$ linker, a $C_2$-$C_5$ linker, a $C_2$-$C_4$ linker, or a $C_3$ linker, wherein each carbon may be independently substituted as described above.

SELEX can also be used to identify aptamers that have desirable off-rate characteristics. See U.S. Pat. No. 7,947,447, entitled "Method for Generating Aptamers with Improved Off-Rates," which describes improved SELEX methods for generating aptamers that can bind to target molecules. Methods for producing aptamers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates dissociate and do not reform, while complexes with slow dissociation rates remain intact. Additionally, the methods include the use of modified nucleotides in the production of candidate nucleic acid mixtures to generate aptamers with improved off-rate performance (see U.S. Patent Publication No. 2009/0098549, entitled "SELEX and PhotoSELEX"). (See also U.S. Pat. No. 7,855,054 and U.S. Patent Publication No. 2007/0166740). Each of these applications is incorporated herein by reference in its entirety.

In some embodiments, methods of selecting aptamers that bind to a target molecule including, for example, DEK are provided, comprising: (a) preparing a candidate mixture of nucleic acids, wherein the candidate mixture comprises modified nucleic acids in which at least one pyrimidine in at least one, or in each, nucleic acid of the candidate mixture is chemically modified at the C5-position; (b) contacting the candidate mixture with a target molecule, wherein nucleic acids having an increased affinity to the target molecule relative to other nucleic acids in the candidate mixture bind the target molecule, forming nucleic acid-target molecule complexes; (c) partitioning the increased affinity nucleic acids from the remainder of the candidate mixture; and (d) amplifying the increased affinity nucleic acids to yield a mixture of nucleic acids enriched in nucleic acid sequences that are capable of binding to the target molecule with increased affinity, whereby an aptamer to the target molecule is identified. In certain embodiments, the method further includes performing a slow off-rate enrichment process.

"Target" or "target molecule" or "target" refers herein to any compound upon which a nucleic acid can act in a desirable manner. A target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc., without limitation. Virtually any chemical or biological effector may be a suitable target. Molecules of any size can serve as targets. A target can also be modified in certain ways to enhance the likelihood or strength of an interaction between the target and the nucleic acid. A target can also include any minor variation of a particular compound or molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Embodiments of the SELEX process in which the target is a peptide are described in U.S. Pat. No. 6,376,190, entitled "Modified SELEX Processes Without Purified Proteins.

The term "second agent" refers to a therapeutic agent other than the DEK aptamer in accordance with the present invention. In certain instances, the second agent is an anti-inflammatory agent.

The term "co-administration" refers to the administration of at least two agent(s) (e.g., DEK aptamer) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

The term "combination therapy" includes the administration of an anti-inflammatory agent (e.g., DEK aptamer) and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule or injection having a fixed ratio of each therapeutic agent or in multiple, single capsules or injections for each of the therapeutic agents. Sequential or substantially simultaneous administration of each therapeutic agent can be effected by any appropriate route including, but not limited to, oral routes, intravenous routes, intramuscular routes, intra-articular routes, corneal routes, topical routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Sequence identity, as used herein, in the context of two or more nucleic acid sequences is a function of the number of identical nucleotide positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www (dot) ncbi (dot) nlm (dot) nih (dot) gov/BLAST). For sequence comparisons, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith and Waterman, Adv. Appl. Math., 2:482, 1981, by the homology alignment algorithm of Needleman and Wunsch, J. Mol. Biol., 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M. et al., *Current Protocols in Molecular Biology*, pub. by Greene Publishing Assoc. and Wiley-Interscience (1987)). As used herein, when describing the percent identity of a nucleic acid it is intended that the nucleic acid sequence is identical to the reference sequence except that the nucleic acid sequence may include up to five point mutations per each 100 nucleotides of the reference nucleic acid sequence. In other words, to obtain a desired nucleic acid sequence, the sequence of which is at least about 95% identical to a reference nucleic acid sequence, up to 5% of the nucleotides in the reference sequence may be deleted or substituted with another nucleotide, or some number of nucleotides up to 5% of the total number of nucleotides in the reference sequence may be inserted into the reference sequence (referred to herein as an insertion). These mutations of the reference sequence to generate the desired sequence may occur at the 5' or 3' terminal positions of the reference nucleotide sequence or anywhere between those terminal positions, interspersed either individually among nucleotides in the reference sequence or in one or more contiguous groups within the reference sequence.

Ranges provided herein are understood to be shorthand for all of the values within the range. For example, a range of 1 to 50 is understood to include any number, combination of numbers, or sub-range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated.

DETAILED DESCRIPTION

DEK

DEK is a nuclear protein that regulates hematopoiesis and participates in pathways involving secretion, receptor engagement, uptake, and subsequent modulation of heterochromatin biology, gene expression and hematopoietic cell cycling and migration. (Broxmeyer H E, et al. "A Role for DEK in Stem/Progenitor Cell Biology". Stem Cells. 2013. Epub 2013/06/05; Kappes F, et al. "The DEK oncoprotein is a Su(var) that is essential to heterochromatin integrity". Genes Dev. 2011; 25(7):673-678; Mor-Vaknin N et al. "The DEK nuclear autoantigen is a secreted chemotactic factor". Mol Cell Biol. 2006; 26(24):9484-9496; Kappes F, et al. "DEK is a poly(ADP-ribose) acceptor in apoptosis and mediates resistance to genotoxic stress". Mol Cell Biol. 2008; 28(10):3245-3257; Saha A K et al. "Intercellular trafficking of the nuclear oncoprotein DEK". Proc Natl Acad Sci USA. 2013; 110(17):6847-6852.) DEK aptamers are nucleic acid molecules, or derivatives of variants thereof, that are selected through screening of large random libraries of nucleic acid molecules for those that bind to a protein of interest. Hits that emerge are put through multiple rounds of selection to discover aptamers that bind most tightly to a protein of interest. Using SELEX, single-stranded DNA aptamers that bind avidly and specifically to DEK, inactivate its function, and treat arthritis in an in vivo mouse model have been discovered. DEK aptamers of the present invention provide utility in the treatment of, for example, arthritis, rheumatoid arthritis (RA), juvenile rheumatoid arthritis (JRA), juvenile idiopathic arthritis (JIA), gout, autoimmune disorders, infectious disorders, malignant disorders and other disorders mediated by an inflammatory response.

DEK Aptamers

In some embodiments, a DEK aptamer comprises a nucleotide sequence shown in any one of SEQ ID NOs: 1 (5' ATA GGG AGT CGA CCG ACC AGA AGG GGT TAA ATA TTC
CCA CAT TGC CTG CGC CAG TAC AAA TAG TAT GTG CGT CTA CAT CTA GACT
3')
(DEK aptamer 64), and SEQ ID NO: 2 (5' ATA GGG AGT CGA CCG ACC AGA ATA CCG TGG CAT CTG GTT GTA GCA TCA CGT CTT ATG CGG CCG TAT GTG CGT CTA CAT CTA GACT 3' (DEK aptamer 85) and SEQ ID NO: 6 (5'-GGG GTT AAA TAT TCC CAC ATT GCC TGC GCC AGT ACA AAT AG-3').

In some embodiments, 1 to 20, 1 to 15, 1 to 12, 1 to 8, 1 to 5, or 1 to 3 nucleotides of SEQ ID NOs: 1, 2 or 6 may be substituted, deleted, or inserted. The number of nucleotides substituted, deleted, or inserted is not particularly limited as long as the aptamer specifically binds DEK with affinity ($K_d$) of, for example, less than 20 nM and/or has DEK antagonist activity ($IC_{50}$) of, for example, less than 10 nM ($10^{-8}$M). In some embodiments, the DEK aptamer comprises not more than 10, and in some embodiments, 4, 3, 2, or 1, nucleotide substitutions, deletions, and/or insertions relative to a sequence of any one of SEQ ID NOs: 1, 2 and 6.

In some embodiments, the present disclosure provides a DEK aptamer that, upon binding DEK, modulates a DEK function. In some embodiments, a DEK aptamer described herein inhibits DEK-mediated inflammation. In various embodiments, the aptamer modulates a DEK function in vivo, such as inhibiting inflammation. In some embodiments, the DEK aptamer comprises at least 12, at least 13, at least 14, at least 15, at least 16, at least 17, at least 18, at least 19, at least 20, at least 21, at least 21, at least 22, at least 23, at least 24, at least 25, at least 26, at least 27, at least 28, at least 29, or at least 30 contiguous nucleotides of an aptamer selected from SEQ ID NOs: 1, 2 and 6 wherein the aptamer specifically binds DEK with an affinity ($K_d$) of, for example, less than 20 nM and/or has DEK antagonist activity ($IC_{50}$) of, for example, less than 10 nM ($10^{-8}$M).

In some embodiments, a DEK aptamer may comprise additional nucleotides or other chemical moieties on the 5' end, the 3' end, or both the 5' and the 3' end of the aptamer. The DEK aptamer can contain any number of nucleotides in addition to the DEK binding region. In various embodiments, the DEK aptamer can include up to about 100 nucleotides, up to about 95 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides, up to about 35 nucleotides, up to about 30 nucleotides, up to about 25 nucleotides, and up to about 20 nucleotides.

In some embodiments, the DEK aptamer is selected from an aptamer that has similar binding characteristics and ability to treat DEK associated inflammatory diseases, malignant diseases, infections, autoimmune diseases, and other diseases or conditions in which DEK has been implicated as an aptamer selected from SEQ ID NOs: 1, 2 and 6. In some embodiments, a DEK aptamer is provided that binds to the same region of DEK as an aptamer selected from the aptamers of SEQ ID NOs: 1, 2 and 6.

In some embodiments, the DEK aptamers specifically bind mature DEK. In some embodiments, the DEK aptamer is selected to have any suitable dissociation constant ($K_d$) for DEK. In some embodiments, a DEK aptamer has a dissociation constant ($K_d$) for DEK of less than 30 nM, less than 25 nM, less than 20 nM, less than 15 nM, less than 10 nM, less than 9 nM, less than 8 nM, less than 7 nM, less than 6 nM, less than 5 nM, less than 4 nM, less than 3 nM, less than 2 nM, or less than 1 nM. Dissociation constants may be determined with a binding assay using a multi-point titration and fitting the equation $y=(max-min)(Protein)/(K_d+Protein)+min$ In some embodiments, a DEKaptamer has DEK antagonist activity ($IC_{50}$) of less than $10^{-8}$M (<10 nM), less than $10^{-9}$M, less than $10^{-10}$ M, or less than $10^{-11}$M. In various embodiments, DEK antagonist activity may be determined using, for example, a cell inflammation assay and/or a gene reporter assay Methods of Detecting DEK In some embodiments, methods of detecting DEK in a sample are provided, comprising contacting the sample with an aptamer described herein. In some embodiments, the method comprises contacting the sample with a DEK aptamer described herein in the presence of a polyanionic inhibitor. Detecting and/or quantifying DEK bound by the DEK aptamer can be accomplished using methods in the art and/or methods described herein. In some embodiments, the DEK aptamer comprises a detectable label. In some embodiments, the DEK aptamer is bound to a solid support, or comprises a member of a binding pair that may be captured on a solid support (for example, a biotinylated aptamer may be bound to a solid support comprising streptavidin).

Pharmaceutical Compositions Comprising DEK Aptamers

In some embodiments, pharmaceutical compositions comprising at least one aptamer described herein and at least one pharmaceutically acceptable carrier are provided. Suitable carriers are described in "Remington: The Science and Practice of Pharmacy, Twenty-first Edition," published by Lippincott Williams & Wilkins, which is incorporated herein by reference.

Pharmaceutical compositions that include at least one aptamer described herein and at least one pharmaceutically acceptable carrier may also include one or more other active agents. The aptamers described herein can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the aptamers described herein can be formulated: (a) for administration selected from any of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from any of liquid dispersions, gels, aerosols, ointments, creams, tablets, sachets and capsules; (c) into a dosage form selected from any of lyophilized formulations, dry powders, fast melt formulations, controlled release formulations, delayed release formulations, extended release formulations, pulsatile release formulations, and mixed immediate release and controlled release formulations; or (d) any combination thereof.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition should be sterile and should be fluid to the extent that easy syringability exists. The pharmaceutical composition should be stable under the conditions of manufacture and storage and should be preserved against the contaminating action of microorganisms such as bacteria and fungi. The term "stable", as used herein, means remaining in a state or condition that is suitable for administration to a subject.

The carrier can be a solvent or dispersion medium, including, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent (e.g., a DEK aptamer) in an appropriate amount in an appropriate solvent with one or a combination of ingredients enumerated above, as desired, followed by filtered sterilization. Generally, dispersions are prepared by incorporating at least one DEK aptamer into a sterile vehicle that contains a basic dispersion medium and any other desired ingredient. In the case of sterile powders for the preparation of sterile injectable solutions, exemplary methods of preparation include vacuum drying and freeze-drying, both of which will yield a powder of a DEK aptamer plus any additional desired ingredient from a previously sterile-filtered solution thereof. Oral compositions generally include an inert diluent or an edible carrier. They can be enclosed, for example, in gelatin capsules or compressed into tablets. For the purpose of oral therapeutic administration, the DEK aptamer can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from a pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In some embodiments, a DEK aptamer is prepared with a carrier that protects against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of a DEK aptamer may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

In some embodiments, it is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of a DEK aptamer calculated to produce the desired therapeutic effect in association with the required pharmaceutical carrier. The specification for the dosage unit forms of DEK aptamers described herein are dictated by and directly dependent on the characteristics of the particular DEK aptamer and the particular therapeutic effect to be achieved, and the limitations inherent in the art of compounding such an active agent for the treatment of individuals.

Pharmaceutical compositions comprising at least one DEK aptamer can include one or more pharmaceutical excipients. Examples of such excipients include, but are not limited to, binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as AVICEL. PH101 and AVICEL. PH102, silicified microcrystalline cellulose (ProSolv SMCC), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, crosspovidone, sodium starch glycolate, and mixtures thereof; (4) lubricants, including agents that act on the flowability of a powder to be compressed, include magnesium stearate, colloidal silicon dioxide, such as AEROSIL 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as AVICEL PH101 and AVICEL. PH102; lactose such as lactose monohydrate, lactose anhydrous, and PHARMATOSE. DCL21; dibasic calcium phosphate such as EMCOMPRESS; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, MAGNASWEET (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In various embodiments, the formulations described herein are substantially pure. As used herein, "substantially pure" means the active ingredient (e.g., a DEK aptamer) is the predominant species present (i.e., on a molar basis it is more abundant than any other individual species in the composition). In one embodiment, a substantially purified fraction is a composition wherein the active ingredient comprises at least about 50 percent (on a molar basis) of all macromolecular species present. Generally, a substantially pure composition will include more than about 80% of all macromolecular species present in the composition. In various embodiments, a substantially pure composition will include at least about 85%, at least about 90%, at least about 95%, or at least about 99% of all macromolecular species present in the composition. In various embodiments, the active ingredient is purified to homogeneity (contaminant species cannot be detected in the composition by conventional detection methods) wherein the composition consists essentially of a single macromolecular species.

Kits Comprising DEK Aptamer Compositions

The present disclosure provides kits comprising any of the DEK aptamers described herein. Such kits can comprise, for example, (1) at least one DEK aptamer; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus.

In certain embodiments, the present invention provides instructions for administering said inhibitors of inflammation (e.g., DEK aptamer) to a subject. In certain embodiments, the present invention provides instructions for using the compositions contained in a kit for the treatment of conditions characterized by inflammation in a cell or tissue (e.g., providing dosing, route of administration, decision trees for treating physicians for correlating patient-specific characteristics with therapeutic courses of action). In certain embodiments, the present invention provides instructions for using the compositions contained in the kit to treat a variety of medical conditions associated with inflammation (e.g., arthritis, rheumatoid arthritis, juvenile rheumatoid arthritis). In certain embodiments, the present invention provides instructions for using the compositions contained in the kit to treat a variety of medical conditions associated with inflammation, and/or autoimmune conditions.

Methods of Treatment

In some embodiments, provided herein are methods of preventing or treating (e.g., alleviating one or more symptoms of) medical conditions through the use of a DEK aptamer. The methods comprise administering a therapeutically effective amount of a DEK aptamer to a subject in need thereof. The described aptamers can also be used for prophylactic therapy. In some embodiments, the DEK aptamer is administered intra-articularly. In some embodiments the DEK aptamer is administered intra-ocularly. The DEK aptamer used in methods of treatment can be: (1) a DEK aptamer described herein, or a pharmaceutically acceptable salt thereof, or a prodrug thereof. The individual or subject can be any animal (domestic, livestock or wild), including, but not limited to, cats, dogs, horses, pigs and cattle, and preferably human subjects. As used herein, the terms patient, individual, and subject may be used interchangeably.

As used herein, "treating" describes the management and care of a patient for the purpose of treating a disease, condition, or disorder and includes the administration of a DEK aptamer to prevent the onset of the symptoms or complications of a disease, condition or disorder; to alleviate symptoms or complications of the disease, condition, or disorder; or to eliminate the presence of the disease, condition or disorder in the patient. More specifically, "treating" includes reversing, attenuating, alleviating, minimizing, suppressing or halting at least one deleterious symptom or effect of a disease (disorder) state, disease progression, disease causative agent or other abnormal condition. Treatment is generally continued as long as symptoms and/or pathology ameliorate.

In some embodiments, compositions and methods of the present invention are used to prevent, treat, and/or ameliorate inflammatory diseases, malignant diseases, infections, autoimmune diseases, and/or other diseases or conditions in which DEK is implicated. Non-limiting exemplary inflammatory diseases that may be treated with the DEK aptamers described herein include rheumatoid arthritis, juvenile idiopathic arthritis, systemic-onset juvenile idiopathic arthritis, gout, osteoarthritis, sepsis, asthma, interstitial lung disease, inflammatory bowel disease, systemic sclerosis, intraocular inflammation, Grave's disease, endometriosis, systemic sclerosis, adult-onset still disease, amyloid A amyloidosis, polymyalgia rheumatic, remitting seronegative symmetrical synovitis with pitting edema, Behcet's disease, uveitis, graft-versus-host diseases, and TNFR-associated periodic syndrome. Malignant diseases that may be treated with the DEK aptamers described herein include cancers and cancer-related conditions. Non-limiting exemplary cancers include multiple myeloma, leukemia, pancreatic cancer, breast cancer, colorectal cancer, cachexia, melanoma, cervical cancer, ovarian cancer, lymphoma, gastrointestinal, lung cancer, prostate cancer, renal cell carcinoma, metastatic kidney cancer, solid tumors, non-small cell lung carcinoma, non-Hodgkin's lymphoma, bladder cancer, oral cancer, myeloproliferative neoplasm, B-cell lymphoproliferative disease, and plasma cell leukemia. Non-limiting exemplary cancer-related conditions include non-small cell lung cancer-related fatigue and cancer related anorexia. Non-limiting exemplary infections that may be treated with the DEK aptamers described herein include human immunodeficiency virus (HIV), human T-lymphotropic virus (HTLV), cerebral malaria, urinary tract infections, and meningococcal infections. Non-limiting exemplary autoimmune diseases that may be treated with the DEK aptamers described herein include systemic lupus erythromatosus, systemic sclerosis, polymyositis, vasculitis syndrome including giant cell arteritis, takayasu aeteritis, cryoglobulinemia, myeloperoxidase-antineutrophilcytoplasmic antibody-associated crescentic glomerulonephritis, rheumatoid vasculitis, Crohn's disease, relapsing polychondritis, acquired hemophilia A, and autoimmune hemolytic anemia. Further diseases that may be treated with the DEK aptamers described herein include, but are not limited to, Castleman's disease, ankylosing spondyliytis, coronary heart disease, cardiovascular disease in rheumatoid arthritis, pulmonary arterial hypertension, chronic obstructive pulmonary disease (COPD), atopic dermatitis, psoriasis, sciatica, type II diabetes, obesity, giant cell arteritis, acute graft-versus-host disease (GVHD), non-ST elevation myocardial infarction, anti-neutrophil cytoplasmic antibody (ANCA) associated vasculitis, neuromyelitis optica, chronic glomerulonephritis, and Takayasu arteritis.

In some embodiments, the disclosed compounds or pharmaceutically acceptable salts thereof, or prodrugs, can be administered in combination with other active agents. Compositions including the disclosed DEK aptamers may contain, for example, more than one aptamer. In some embodiments, a composition containing one or more DEK aptamers is administered in combination with one or more additional agents for preventing, treating, and/or ameliorating inflammatory diseases, malignant diseases, infections, autoimmune diseases, and/or other diseases or conditions in which DEK is implicated.

The dosage regimen utilizing the DEK aptamers is selected in accordance with a variety of factors, including, for example, type, species, age, weight, sex and medical condition of the subject; the severity of the condition to be treated; the route of administration; the renal and hepatic function of the subject; and the particular aptamer or salts thereof employed. An ordinarily skilled physician or veterinarian can readily determine and prescribe the effective amount of the composition required to prevent, counter or arrest the progress of the condition. In general, the dosage, i.e., the therapeutically effective amount, ranges from about 1 ng/kg to about 1 g/kg body weight, in some embodiments about 1 ug/kg to about 1 g/kg body weight, in some embodiments about 1 ug/kg to about 100 mg/kg body weight, in some embodiments about 1 ug/kg to about 10 mg/kg body weight of the subject being treated, per day.

Methods for Diagnosing and Detecting

Aptamers that bind DEK, described herein, find use as diagnostic reagents, either in vitro or in vivo. The DEK aptamers identified herein can be used in any diagnostic, detection, imaging, high throughput screening or target validation techniques or procedures or assays for which aptamers, oligonucleotides, antibodies and ligands, without limitation can be used. For example, DEK aptamers identified herein can be used according to the methods described in detail in U.S. Pat. No. 7,855,054, entitled "Multiplexed Analyses of Test Samples", which is incorporated by reference herein in its entirety.

Aptamers capable of binding DEK, described herein, find use in a variety of assays including, assays that use planar arrays, beads, and other types of solid supports. The assays may be used in a variety of contexts including in life science research applications, clinical diagnostic applications, (e.g., a diagnostic test for a disease, or a "wellness" test for preventative healthcare); ALONA and UPS assays, and in vivo imaging applications. For some applications, multiplexed assays employing the described DEK aptamers and may be used.

In some embodiments, the DEK aptamers are used as sensitive and specific reagents for incorporation into a variety of in vitro diagnostic methods or kits. In some embodiments, the DEK aptamers are used as substitutes for antibodies in a number of infectious, or other type of, disease detection methods where the aptamer to DEK includes either or both a detectable material and an immobilization or capture component. In these embodiments, after the aptamer from the kit is mixed with a clinical specimen, a variety of assay formats may be utilized. In one embodiment, the aptamer also includes a detectable label, such as a fluorophore. In other embodiments, the assay format may include fluorescence quenching, hybridization methods, flow cytometry, mass spectroscopy, inhibition or competition methods, enzyme linked oligonucleotide assays, SPR, evanescent wave methods, etc. In some embodiments, the aptamer is provided in the kit in solution. In other embodiments, the aptamer in the kit is immobilized onto a solid support used in conjunction with the assay for testing the specimen. In various embodiments, the solid support is designed for the detection of one or more targets of interest. In other embodiments, the kit may further include reagents to extract the target of interest, reagents for amplifying the aptamer, reagents for performing washing, detection reagents, etc.

Diagnostic or assay devices, e.g. columns, test strips or biochips, having one or more DEK aptamers adhered to a solid surface of the device are also provided. The aptamer(s) may be positioned so as to be capable of binding DEK molecules that are contacted with the solid surface to form aptamer-target complexes that remain adhered to the surface of the device, thereby capturing the target and enabling detection and optionally quantitation of the target. An array of aptamers (which may be the same or different) may be provided on such a device.

In one embodiment for detecting DEK, an aptamer affinity complex or aptamer covalent complex is contacted with a labeling agent that includes a binding partner that is specific for DEK. The specific binding partner may be any suitable moiety, including an antibody, an antibody fragment, a synthetic antibody mimetic, a biomimetic, an aptamer, a molecular imprinted ligand, and the like. The specific binding partner is conjugated or linked to another labeling agent component, usually, a detectable moiety or label. In one embodiment for detecting DEK, an aptamer affinity complex or aptamer covalent complex is contacted with a labeling agent that is capable of labeling DEK, without a binding partner, and comprises a detectable moiety or label.

The detectable moiety or label is capable of being detected directly or indirectly. In general, any reporter molecule that is detectable can be a label. Labels include, for example, (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation, and (v) a specific polynucleotide sequence or recognition sequence that can act as a ligand, such as, for example, a repressor protein, wherein in the latter two instances the oligonucleotide primer or repressor protein will have, or be capable of having, a reporter molecule, and so forth. The reporter molecule can be a catalyst, such as an enzyme, a polynucleotide coding for a catalyst, promoter, dye, fluorescent molecule, quantum dot, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like. The label can be selected from electromagnetic or electrochemical materials. In one embodiment, the detectable label is a fluorescent dye. Other labels and labeling schemes will be evident to one skilled in the art based on the disclosure herein.

EXAMPLES

The invention, now being generally described, will be more readily understood by reference to the following examples, which are included merely for purposes of illustration of certain aspects and embodiments of the present invention, and are not intended to limit the invention. Data are presented as means±SEM. The difference between means was analyzed using the unpaired Student's t-test. A p value <0.05 was considered significant. All protocols for animal and human studies were approved by the University of Michigan's Committee on Use and Care of Animal or the Institutional Review Board.

Example 1

This example describes a selection protocol for DEK aptamers.

SELEX technology, a method that selects for either single-stranded DNAs or RNAs that bind tightly to the protein of interest and can potentially inactivate its function, was used to generate anti-DEK apamters. (Nimjee, S. M., Rusconi, C. P. & Sullenger, B. A. Aptamers: an emerging class of therapeutics. *Annu Rev Med* 56, 555-583, doi: 10.1146/annurev.med.56.062904.144915 (2005), Que-Gewirth, N. S. & Sullenger, B. A. Gene therapy progress and prospects: RNA aptamers. *Gene therapy* 14, 283-291, doi: 10.1038/sj.gt.3302900 (2007).) SELEX is performed using multiple rounds of selection and involves screening large numbers of random DNA or RNA sequences to identify a sequence of interest. A 40 nucleotide, single-stranded DNA 5'-GGG GTT AAA TAT TCC CAC ATT GCC TGC GCC AGT ACA AAT AG-3' (SEQ ID NO: 6), with high affinity for recombinant DEK protein produced in a baculovirus system which binds tightly to DEK.

A pool of 86-nucleotide DNA oligomer containing 40 central nucleotides of random sequence flanked by defined primer-binding sites (FIG. 1) was synthesized to order by Integrated DNA Technologies (Coralville, Iowa). This resulted in an initial pool with estimated complexity of $10^{14}$-$10^{16}$ different sequences: (5'-ATAGGAGTC-GAC-CGACCAGAA [N]40 TATGTGCGTCTACATCTA-GACT-CAT-3') (SEQ ID NO: 3). Short DNA oligonucleotides for amplifying selected sequences were: 5'-primer, 5'-ATAG-GAGTCGACCGACCAGA A (SEQ ID NO: 4); 3'-primer, 5'-ATGAGTCTAGATGTAGACGCACATA (SEQ ID NO: 5). FIG. 1 shows recombinant DEK protein conjugated to nickel agarose beads incubated with a library including a pool of $10^{14}$-$10^{16}$ random single-stranded DNA sequences. Each sequence includes 40 nucleotides (nt) flanked by 22 known nt on each side that serve as primers for amplification by PCR. After extensive washes, the bound nt are eluted and amplified by PCR reaction. The steps were repeated up to 6 times to achieve specificity and to eliminate nonspecific binding of the sequences to the naked beads.

Round 1

For the first round of selection, approximately 1 mg of randomized single-stranded DNA library (Integrated DNA Technologies, Corralville, Iowa) was incubated with 1.5 mL bed volume of nickel-nitrilotriacetic acid (Ni-NTA) agarose resin (Qiagen, Germantown, Md.) conjugated to histidine-tagged DEK protein (at ~1 mg DEK per mL of resin) in 5 mL of binding buffer (20 mM Tris pH 7.6; 100 mM NaCl; 5 mM $MgCl_2$). To obtain the DEK protein, the open reading frame of human DEK was cloned into the multiple cloning site of pBlueBacHis2A (Invitrogen). SF-9 cells (Invitrogen) were co-transfected with linearized *Autographa californica* nuclear polyhedrosis virus DNA with the Bac-N-Blue DNA transfection kit (Invitrogen) in accordance with the manufacturer's protocol. Five days after cotransfection, the supernatant was harvested and subjected to plaque assays. Single plaques were picked, and a high-titer virus stock was raised. Three days post-infection with a high-titer virus stock, HighFive cells were harvested and washed three times with phosphate-buffered saline prior to lysis with 2 ml of lysis buffer per 175-$cm^2$ flask (100 mM Tris-Cl [pH 7.5], 150 mM NaCl, 5 mM KCl, 0.5 mM $MgCl_2$, 1% NP-40.5 mM imidazole). To disrupt DNA-protein and protein-protein interactions, the lysed cells were further incubated in the presence of 1.3 M NaCl for 20 min at room temperature. The lysate was cleared (100,000×g, 10 min), adjusted to 10% glycerol, diluted with lysis buffer to a final concentration of 700 mM NaCl, and incubated with 10 ul of equilibrated 50% Ni-nitrilotriacetic acid (NTA)-agarose (Qiagen, Germantown, Md.) per 2 ml of lysate. After binding for 1 h at 4° C., the beads were washed three times with 10 volumes of buffer 1 [(50 mM Tris-Cl [pH 7.5], 150 mM NaCl, 50 mM imidazole)], three times with 10 volumes of buffer 2 [(50 mM Tris-Cl [pH 7.5], 300 mM NaCl, and 50 mM imidazole)], and again with 10 volumes of buffer 1. Elution was performed with 50 mM Tris-Cl [pH 7.5]—150 mM NaCl—500 mM imidazole. Aliquots of recombinant protein were stored at −70° C. in elution buffer. (See, for example, Kappes et al., *Phosphorylation or Protein Kinase CK2 Changes the DNA Binding Properties of Human* Chromatin Protein DEK. Molecular and Cellular Biology. 24: 6011-6020, 2004.) The library was allowed to bind to the resin-conjugated DEK for one hour at room temperature on a rotating wheel. The resin was spun down gently in a swinging-bucket centrifuge and the supernatant was removed. In fresh binding buffer, the resin was transferred to a clean 50-mL conical tube and washed 4 times with 25 mL binding buffer, 15 minutes each wash, transferring to a clean conical tube after the second wash. To elute, the resin was transferred to a clean 15-mL conical tube and incubated with 1.5 mL elution buffer (20 mM Tris pH 7.6; 5 mM $MgCl_2$; 1 M NaCl; 7 M urea) for 1 hour on a rotating wheel at room temperature. The resin slurry in elution buffer was applied to 0.45 µm spin columns (Millipore, Darmstadt, Germany), and spun in a microcentrifuge to separate the eluate from the beads. An additional 500 µL of elution buffer was applied to the 15-mL conical tube to recover any additional beads that had stuck to the sides during the elution step; this too was spun through the spin columns. Thus, the total recovery volume was ~2 mL. This volume was then extracted twice, with equal volume phenol:chloroform:isoamyl alcohol (25:24:1), extracted once with equal volume chloroform, then precipitated with 2.5 volumes of ethanol and resuspended in 20 mM Tris pH 7.6.

To amplify aptamers that bind to DEK, asymmetric PCR amplification was performed with DNA oligonucleotide primers complementary to end sequences (5:1 ratio of 5' primer to 3' primer) (5'-primer, 5'-ATAGGAGTCGAC-CGACCAGA A (SEQ ID NO. 4); 3'-primer, 5'-AT-GAGTCTAGATGTAGACGCACATA SEQ ID No. 5; Integrated DNA Technologies, Coralville, Iowa). The amplified DNA pool was then gel purified through denaturing polyacrylamide gel electrophoresis (PAGE), and soaking elution/ethanol precipitation to proceed to the next round.

Round 2

One-fourth of the resin from the Round 1 step (i.e., approx. 375 µL bed volume) was used for Round 2 and subsequent rounds. The resin was washed in binding buffer and transferred to a pre-lubricated Eppendorf tube (Sorenson BioScience, #11700, Salt Lake City, Utah). To this resin was added the amplified and gel-purified DNA pool from Round 1. This mixture was allowed to bind for one hour at room temperature on a rotating wheel. The mixture was then transferred to a 0.45 µm spin column and the unbound fraction was spun out. The resin was washed 4 times, each in 500 µL binding buffer, keeping the resin in the spin column during the washes, inverting vigorously several times each, and spinning out. To elute, with the resin still in the column, 200 µL of elution buffer was added, and eluted for 15 minutes on a room temperature rotating wheel. The eluate was spun through in a microcentrifuge to separate away from the resin. In order to dilute the salt and the urea, 200 uL of water was added to the eluate prior to proceeding with ethanol precipitation.

Asymmetric PCR amplification was performed with DNA oligonucleotide primers complementary to end sequences (5:1 ratio of 5' primer to 3' primer) as above. The amplified DNA pool was then gel purified through denaturing polyacrylamide gel electrophoresis, and soaking elution/ethanol precipitation before proceeding to the next round.

Rounds 3-5

Prior to proceeding to Round 3, a subtraction was performed to remove nonspecific binders. 100 µL of Ni-NTA slurry (with no DEK conjugated) was washed once in binding buffer and added to the Round 2 DNA pool in fresh binding buffer. This mixture was incubated for 30 minutes on a rotating wheel at room temperature to allow nonspecific binders to separate. To continue with Round 3, the supernatant was spun out and added to the same DEK-conjugated resin used for Round 2. Round 3 proceeded exactly as Round 2.

After PCR and gel purification, Round 4 was performed without subtraction. Between Rounds 4 and 5, a second subtraction step was performed as above. Round 5 selection was done as with other rounds. Asymmetric PCR amplification was performed with DNA oligonucleotide primers complementary to end sequences (5:1 ratio of 5' primer to 3' primer) as above. The amplified DNA pool was then gel purified through denaturing polyacrylamide gel electrophoresis and soaking elution/ethanol precipitation to proceed to the next round.

Round 6

The gel-purified DNA pool from Round 5 was radiolabeled to provide visualization via native PAGE gel shift. Approximately 1 million counts (<1 microgram) of labeled DNA was incubated with titrated amounts of soluble (i.e., not conjugated to [his×6]) DEK protein (starting at 128 ng, with two-fold dilutions down to 1 ng) in 10 microliters. Bound DEK-DNA complex was separated from free DNA on a 6% native gel supplemented with 5 mM $MgCl_2$ and 5% glycerol. From the lane that gave the greatest % shift of DNA in a single band, the bound complex was excised and eluted in 20 mM Tris pH 7.6.

The Round 6 DEK pool was amplified via asymmetric PCR (5:1 (250 uM: 50 uM) ratio of 5' primer to 3' primer) and radiolabeled following the T4-polynucleotide kinase (PNK) protocol (New England Bioscience, Ipswich, Mass.): 1 ul T4 PNK, 1 ul $^{32}P$ ATP (3,000 Ci/mmol, 5 mCi/ml), 2 ul 10×T4 PNK buffer, 1 ug DNA, and $H_2O$ up to 20 uL). The radiolabeled DNA was separated from the unincorporated $^{32}P$ via a 6% denaturing gel. The bands corresponding to the correct size were excised and soaked in 400 uL of water overnight. The DNA was then precipitated and re-suspended in water. The amount of $^{32}P$ labeled DNA in each tube was determined using a scintillation counter (Beckman LS6500, Beckman Coulter, Indianapolis, Ind.).

DEK Round 6 Binding

To test binding of the radiolabeled pools to the DEK protein, a dot blot was performed. Glass fiber filter paper A (Whatman/GE Healthcare, Pittsburgh, Pa.) and DEAE filters (Whatman/GE Healthcare, Pittsburgh, Pa.) were soaked in binding buffer for one-hour prior to use. 100 ng of DEK protein was incubated in binding buffer and 100 ug/ml of salmon sperm DNA for 15 min. 5,000 CPM of the radiolabeled DNA pool was incubated with the DEK and salmon sperm solution on a rotator for one hour. The dot blot vacuum filter apparatus was set up with the DEAE paper on the bottom and the GFC/A paper on top. Each well was washed with 100 uL of cold binding buffer (see Round 1 above). 100 uL of the radiolabeled pool/DEK protein solution was placed into each well 8 samples at a time, and immediately vacuumed until the solution passed through the membrane. The wells were then immediately washed with 100 uL of cold binding buffer. When all of the samples were loaded, all of the wells were washed 3× with 200 uL of binding buffer. The membrane was then dried, and signal determined using a Typhoon phosporimager (GE Healtcare, Pittsburgh, Pa.) for 1-2 hours to determine individual aptamers that had signal above background of the same reaction without DEK protein.

Example 2

This example describes cloning via pGEM-T kit to obtain "monoclonal" aptamers with individual sequences and properties.

Cloning was performed following the protocol in the Promega pGEM-T kit (Model A3600, Madison, Wis.) using a 3:1 molar ratio of final aptamer pool made double-stranded by PCR to pGEM plasmid, and the electroporation transformation (BioRad Gene Pulser, according to manufacturer's instructions (Hercules, Calif.). After plating on LB/Amp media and incubating overnight, white colonies were randomly selected and placed into a symmetric (1:1 (125 uM: 125 nM) 5' primer to 3' primer PCR reaction. (Symmetric PCR conditions: 94° C. 5' [94° C. 30 s, 55° C. 30 s, 72° C. 30 s]×20 rounds, 72° C. C 10', 4° C. hold) using the 5' and 3' primers as above.

Example 3

This example describes PCR amplification with radiolabeling.

After the symmetric PCR was complete to create double-stranded DNA corresponding to the DEK-binding aptamers, the DNA was gel-isolated through 6% denaturing polyacrylamide gels, soaked out into water, and ethanol precipitated with 2.5 volumes of ethanol. This DNA was used with an approximately 5× molar excess of only the 5' primer (sequence same as above) that had been radiolabeled to approximately 10,000,000 counts per microgram labeling with T4 polynucleotide kinase and gamma-$^{32}$P-ATP as above. The asymmetric PCR (repeated unidirectional primer extension) components were as follows:

| Reagents | Amount per reaction (uL) |
| --- | --- |
| DNA from Symmetric PCR | 10 |
| Taq polymerase | 1 standard unit |
| Taq Buffer 10x (no gelatin) | 10 |
| dNTPs (8 mM) | 2.5 |
| 5' LIB SEL No T7 (non-radiolabeled) | 0.25 |
| $^{32}$p 5' | 1,000,000 CPM |
| Taq DNA pol (1:20 dilution of stock) | 5 |
| H$_2$O | Up to 100 uL |

The asymmetric PCR conditions were: 94° C. 5", [94° C. 30", 59° C. 0", 72° C. 30"]×15 rounds, 72° C. 7", 4° hold.

Example 4

This example describes DEK binding.

ssDNA aptamers were amplified from the 96 colonies, with single-stranded asymmetric PCR products radiolabeled as above, and tested to determine their binding ability. Dot blots were performed as in DEK Round 6 binding above. Dot blots of aptamers giving the highest binding signal were repeated in quadruplicate to verify reproducibility.

Example 5

This example describes sequencing of plasmid DNA comprising aptamer sequences.

The corresponding plasmid DNA of high affinity aptamer positive clones were purified using QIAprep spin miniprep kits (Qiagen) and sequenced by the University of Michigan DNA Sequencing Core.

Example 6

This example describes Southwestern blotting to determine aptamer binding to denatured DEK.

After determining the sequences of individual aptamer clones, the corresponding DNA oligonucleotides with and without 5' and 3' priming sequences were ordered from IDT (Coralville, Iowa), and radiolabeled with $^{32}$P according to the NEB T4 Kinase kit protocol as above. Binding was then tested using a southwestern blot of purified DEK protein. A conventional western blot was performed using PVDF Immobillon P (EMDMillipore, Darmstadt, Germany). After the transfer, the membrane was soaked in PreHyb buffer [(10 mM Hepes (pH 7.9), 100 ug/mL salmon sperm DNA (Sigma-Aldrich, St. Louis, Mo.), 5% bovine serum albumin (Sigma-Aldrich, St. Louis, Mo.)] for 30 min on the shaker at room temperature to block the membrane. The PreHyb buffer was then removed and 5 mL of Hyb Buffer [(10 mM Hepes (pH 7.9), 50 mM NaCl, 1 mM EDTA, 1 mM DTT, 0.25% BSA, 2 ug/ul salmon sperm DNA, 50 million CPM aptamer)] was added and incubated on the shaker at room temperature for one hour. The Hyb Buffer was removed and the membrane was washed 3× on the shaker at room temperature for 20 min with wash buffer [(10 mM Hepes (pH 7.9), 300 mM NaCl, 1 mM EDTA, 1 mM DTT, 0.25% BSA)]. The membranes were dried and exposed on a Typhoon Phosphor imager (GE Healthcare, Pittsburgh, Pa.) cassette overnight to visualize the radiolabeled DNA bound to the bands corresponding to DEK protein. SEQ ID NOs 1 and 2 provide positive DNA aptamer sequences comprising 5' and 3' priming sequences. No quantitation was determined.

Example 7

This example describes DEK aptamers that block neutrophil extracellular trap (NET) formation by activated human neutrophils.

DEK protein participates in the formation of NETs i.e., chromatin-containing structures that are vital to the innate immune response (Kessenbrock K. et al. "Netting neutrophils in autoimmune small-vessel vasculitis". Nat Med. 2009; 15(6):623-625, Kahlenberg J M et al., "Neutrophil extracellular trap-associated protein activation of the NLRP3 inflammasome is enhanced in lupus macrophages". J Immunol. 2013; 190(3):1217-1226.). NETs are extracellular structures composed of chromatin, DNA, histones and antimicrobial factors such as neutrophil elastase and myeloperoxidase. DEK is found in the extracellular space and is important for chromatin architecture, and is linked to the pathogenesis of autoimmunity. (Kaplan, M. J. & Radic, M. Neutrophil extracellular traps: double-edged swords of innate immunity. *J Immunol* 189, 2689-2695, doi:10.4049/jimmunol.1201719 189/6/2689 [pii] (2012).)

Forty milliliters of venous blood was collected from each healthy volunteer into a 60 ml sterile syringe containing 7 ml 0.25 M Citrate (0.17 M sodium citrate and 0.083 M citric acid) and 6% Dextran in PBS buffer (without calcium or magnesium). The blood was incubated for 30 min at room temperature prior to collecting the upper phase by Histopaque-1077 (Sigma, St Louis, Mo., USA) and centrifugation for 30 min at 700×g. The neutrophil fraction was resuspended in 10 ml HBSS buffer, after which it was layered on Histopaque-1119 (Sigma, St Louis, Mo., USA) for an additional 30 minute separation by centrifugation at 700×g. The neutrophil fraction was collected, washed once in HBSS, and resuspended to a concentration of 500,000 cells/ml/coverslip in RPMI supplemented with 2% BSA. Cells were mounted on 22×22 mm, 2.5 μm glass coverslips treated with 0.001% poly-L-Lysine (Sigma, St Louis, Mo., USA). A one-hour treatment with LPS (1 μg/ml) or PMA (10 ng/ml) (Sigma, St Louis, Mo., USA) was used to induce NET formation. Aptamers to DEK were added at 1-50 ng/ml (0.78 nM-3.94 nM) to the neutrophil culture prior to phorbol myristate acetate (PMA) stimulation (10 ng/ml) (Sigma, St Louis, Mo., USA) used to induce NETs formation. Cells were fixed in 4% paraformaldehyde/PBS, pH=7, prior to immune-histochemical examination.

Neutrophils were incubated for 1 hour at 37° C., then fixed and stained for NETs with anti-myeloperoxidase (MPO) antibodies and 4, 6-diamidino-2-phenylindole (DAPI) for DNA. (40× magnification) at room temperature for 1 hour followed by incubation with AlexaFluor 488 goat anti-rabbit or AlexaFluor 594 goat anti-mouse antibody (Invitrogen). Other cells were stained with rabbit anti-DEK antibody (1:100) or mouse anti-DEK antibody (1:50 or 1:500, BD Bioscience, 610948), mouse monoclonal anti-elastase (1:500, Abcam, Cambridge, Mass. ab78187), rabbit anti-elastase (1:1000, Abcam, ab 21595), mouse anti-LL-37 (1:100, Abcam, ab64892), or rabbit anti-MPO (1:500, Dako A0398) Nuclei and NETs were visualized by DAPI—Prolong gold antifade (Invitrogen P-36931) or stained with Hoechst. Slides were analyzed using a fluorescence microscope (BX; Olympus) or confocal microscope (Nikon) including Z-stacks of 80 0.3 micron optical sections (60×). Ten high power (40×) images were captured. Images were loaded onto Adobe Photoshop (Adobe System) and NETs were counted manually and shown as a percentage of total neutrophils per field. NETs were counted by at least three independent observers and identified based on overlap of DAPI staining with the NET markers elastase and MPO. For NET quantification Metamorph 7.7 was used compare NET to neutrophil ratios by the Center for Live Cell Imaging (CLCI) at the University of Michigan. The program takes two 24 bit (color) images, a DAPI and a FITC stained image. The RGB channels are split and then the two green channels are added together as well as the two blue channels. The minimum value is set to the average+standard deviation/2 of all the pixels in the image. This threshold is then turned into a binary, where it passes through image filters that connect some of the finer image structures, showing the presence of NETs. Regions are automatically created around the NETs and information is pulled into an excel sheet indicating image number, plane number, region number, area, integrated green signal, nucleus count, green nets, and nets/nuclei.

Figure 2:
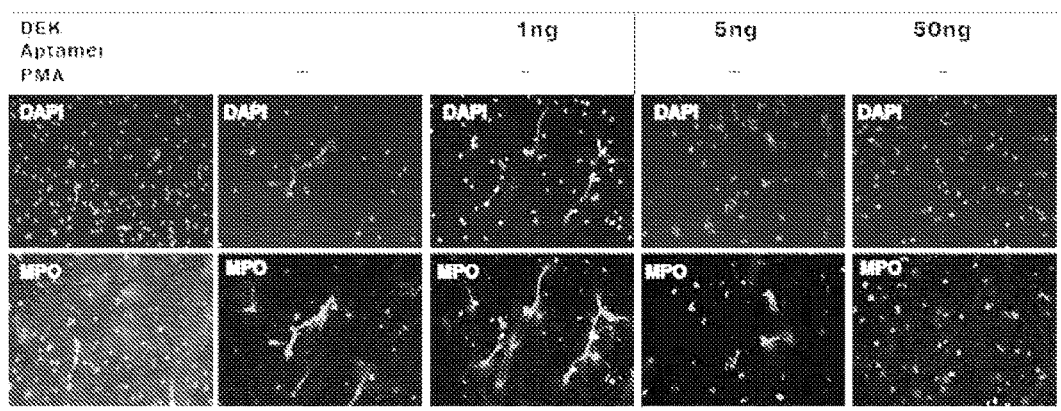
FIG. 2: Shows that DEK aptamers block neutrophil extracellular trap (NET) formation by activated human neutrophils
Figure 3A:
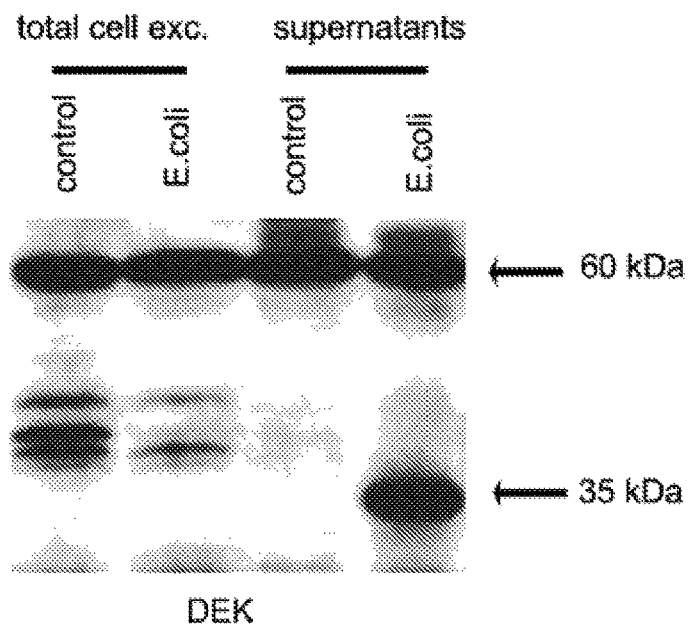
FIG. 3: Shows that stimulation of primary human neutrophils from healthy donors with led to the release of DEK into the extracellular milieu.
Figure 3B:
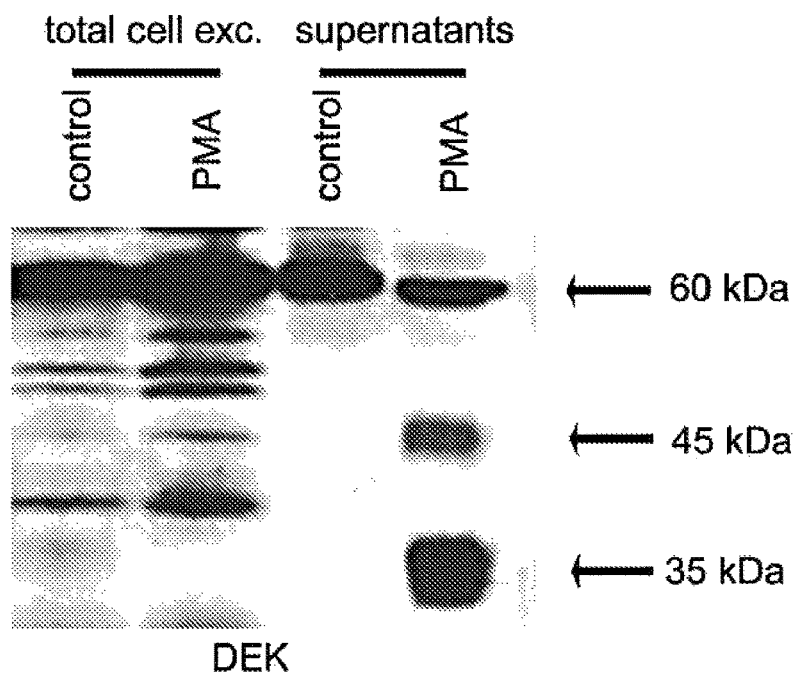
Figure 3C:
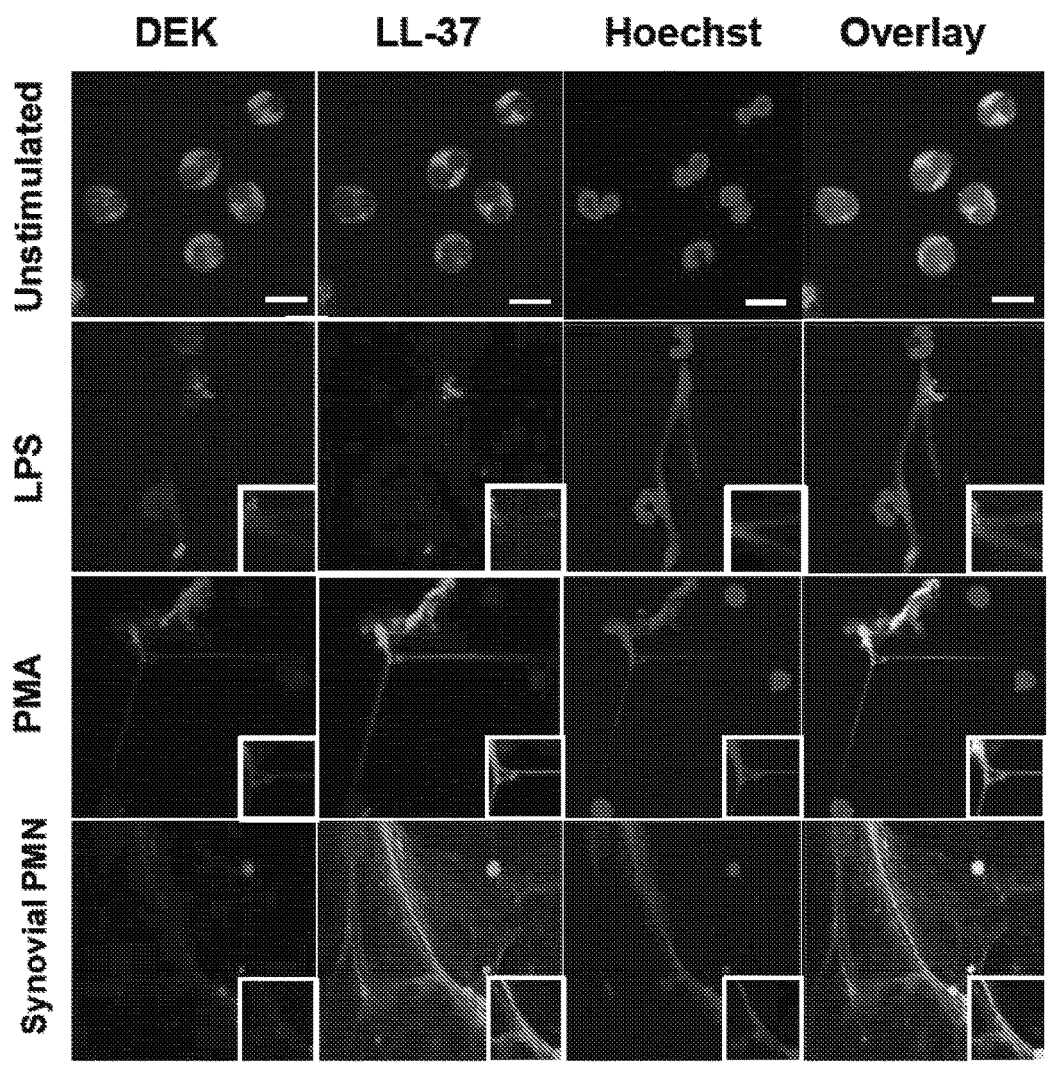
Figure 3D:
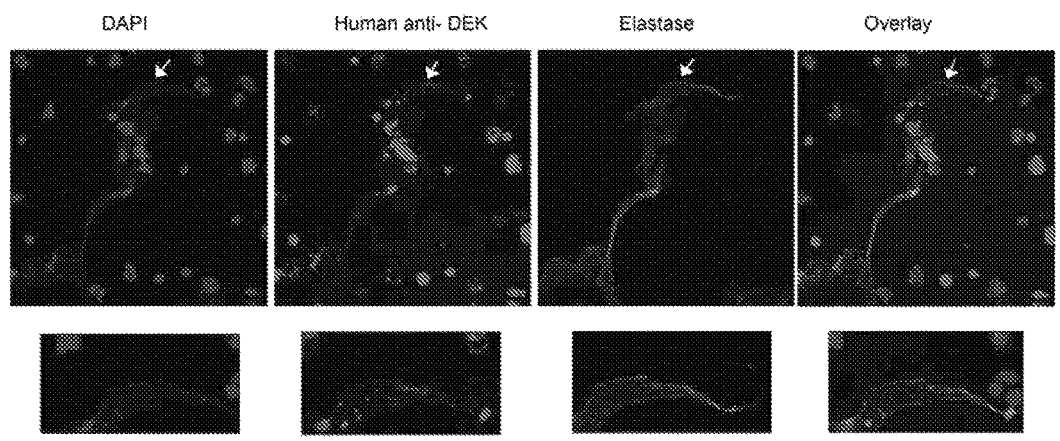
Figure 4A:
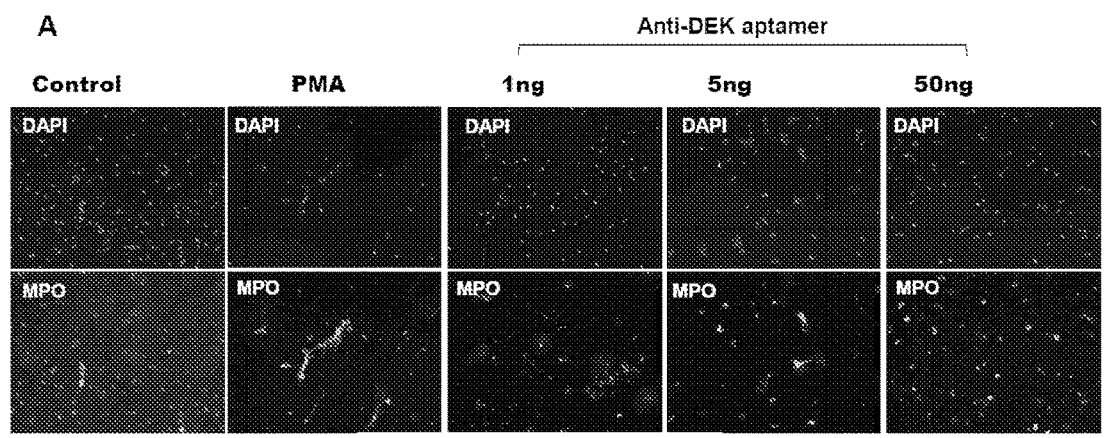
FIG. 4. Shows that incubation with the anti-DEK aptamer SEQ ID NO: 6 blocked formation of PMA-induced NETs by healthy control human peripheral blood neutrophils in a dose-dependent manner.
Figure 4B:
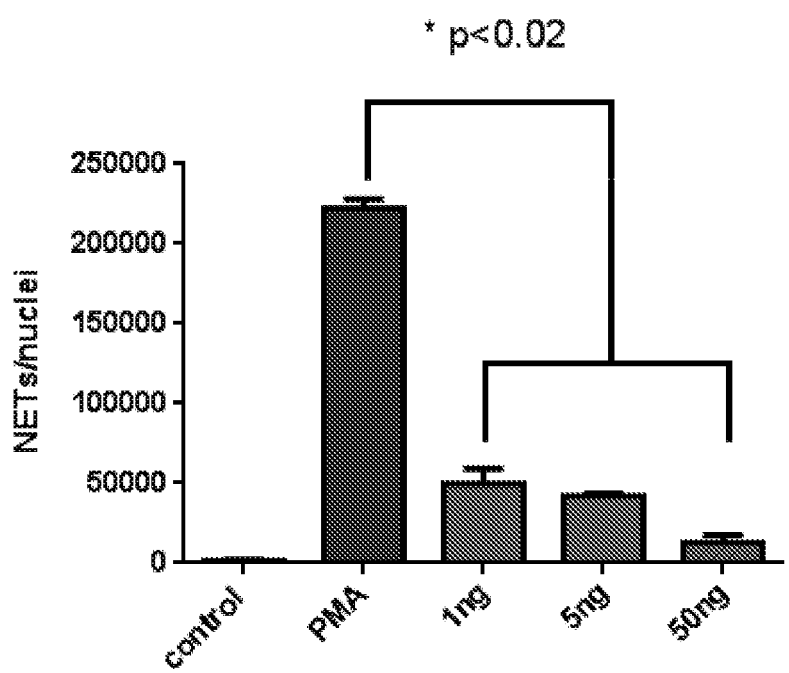

Two DEK aptamers (SEQ ID NO: 1 (aptamer 64) and SEQ ID NO: 2 (aptamer 85) impeded formation of NETs in human primary neutrophils from healthy volunteers (FIG. 2). Stimulation of primary human neutrophils from healthy donors with *Escherichia coli* (*E. coli*) (FIG. 3A) or 10 ng/ml PMA (FIG. 3B) led to the release of DEK into the extracellular milieu. The banding patterns demonstrated by immunoblot analysis are consistent with previously reported findings of numerous DEK isoforms in primary cells. (Mor-Vaknin, N. et al. DEK in the synovium of patients with juvenile idiopathic arthritis: characterization of DEK antibodies and posttranslational modification of the DEK autoantigen. *Arthritis Rheum* 63, 556-567, doi:10.1002/art.30138 (2011)., Sierakowska, H., Williams, K. R., Szer, I. S. & Szer, W. The putative oncoprotein DEK, part of a chimera protein associated with acute myeloid leukaemia, is an autoantigen in juvenile rheumatoid arthritis. *Clin Exp Immunol* 94, 435-439 (1993).) Exposure of fresh neutrophils to *E. coli* or PMA for two hours primarily induced the release of the 35 kDa and 45 kDa forms of DEK, suggesting that DEK is modified as a result of neutrophil activation by *E. coli* or PMA. A 60 kDa form of DEK is detected in the supernatant and in cell extracts of the unstimulated cells. Human peripheral blood neutrophils subjected to LPS or PMA treatment to induce NET formation demonstrated co-localization of DEK with the NET markers LL-37 and neutrophil elastase. (Brinkmann, V. & Zychlinsky, A. Neutrophil extracellular traps: is immunity the second function of chromatin? *J Cell Biol* 198, 773-783, doi:10.1083/jcb.201203170 jcb.201203170 [pii] (2012).) (FIG. 3C) Incubation with the anti-DEK aptamer SEQ ID NO: 6 blocked formation of PMA-induced NETs by healthy control human peripheral blood neutrophils in a dose-dependent manner (FIG. 4A and FIG. 4B).

These results indicate that DEK is present in human NETs, and underscore the important role of DEK in NET formation and inflammation as a target in the treatment of human inflammatory diseases. Treatment of activated human neurophils with anti-DEK apatamer resulted in loss of their ability to generate NETs which are extracellular containing structures.

Example 8

This example describes treatment of arthritis in a mouse model with a DEK aptamer.

Zymosan is a polysaccharide composed primarily of glucan and mannan residues from the cell wall of *Saccharomyces cervesiae* (Di Carlo F J, Fiore J V. "On the composition of zymosan". *Science*. 1958; 127(3301):756-757.) Intra-articular (i.a.) injection of zymosan is used to induce inflammatory arthritis in mice because zymosan is stimulates an innate immune response (Frasnelli M E, Tarussio D, Chobaz-Peclat V, Busso N, So A. "TLR2 modulates inflammation in zymosan-induced arthritis in mice". Arthritis Res Ther. 2005; 7(2):R370-3799.). Monocytes, macrophages, and neutrophils are cell types that recognize and ingest zymosan, thereby leading to their activation.

Zymosan A from *Saccharomyces cerevisiae* (Sigma, St Louis, Mo., USA) (30 mg) was resuspended in 2 ml of endotoxin-free saline, and was subsequently boiled and homogenized by sonic emulsification. Arthritis was induced by intra-articular (i.a.) injection of 300 μg (20 μl) of zymosan through the suprapatellar ligament into the joint space. The contralateral knee was injected with an equal volume of sterile saline (20 μl) as a control. Injection with PBS alone and zymosan alone provided further negative and positive controls. Twelve to 13-week-old female mice (WT) were injected i.a. with zymosan into the knees of both hind legs on day 0. Knee circumference was measured by 2 different investigators in a blind fashion before injection on day 0 and at 24 and 48 hours after injection. Knee circumference determination was achieved by measuring two perpendicular diameters of the joint with calipers. Knee circumference was determined using the following geometric formula: circumference=$2\pi(\sqrt{(a^2+b^2/2)})$, where a is the latero-lateral diameter, and b is the antero-posterior diameter, as previously described. (Woods, J. M. et al. IL-4 adenoviral gene therapy reduces inflammation, proinflammatory cytokines, vascularization, and bony destruction in rat adjuvant-induced arthritis. *J Immunol* 166, 1214-1222 (2001).

Aptamers to DEK and a control from the library (e.g., scrambled/random sequence) were diluted in PBS to a concentration of 5-500 ng/20 ul volume for i.a. injection.

Figure 5A:
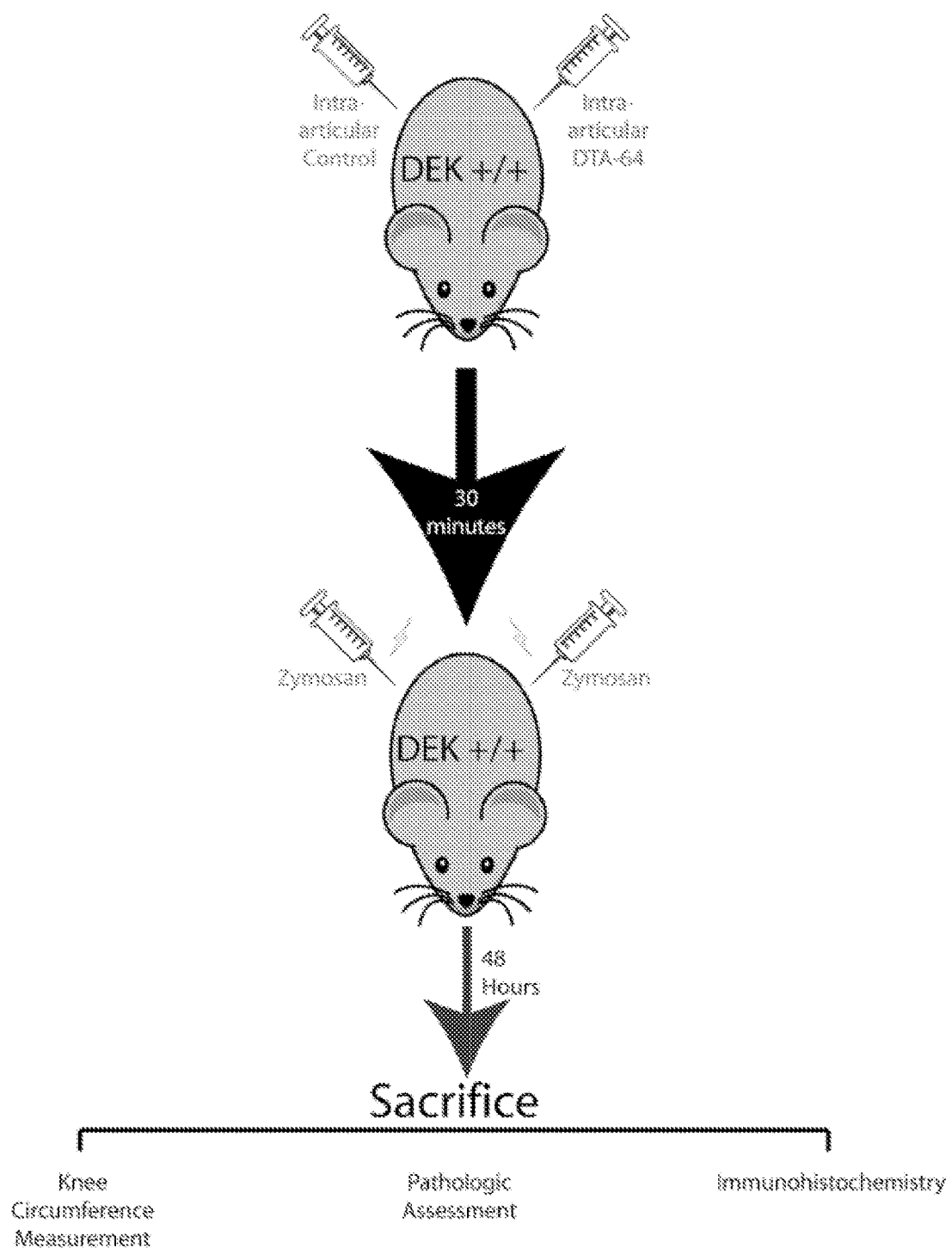
FIG. 5: Shows a zyomsan-induced arthritis (ZIA) model in which anti-DEK aptamer attenuated inflammation in WT mice.
Figure 5B:
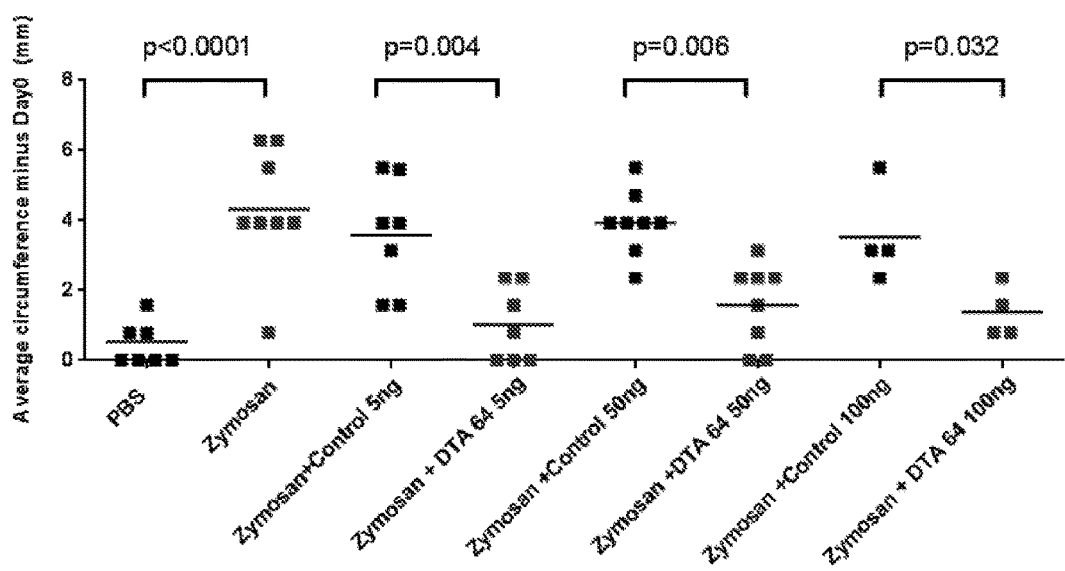
Figure 5C:
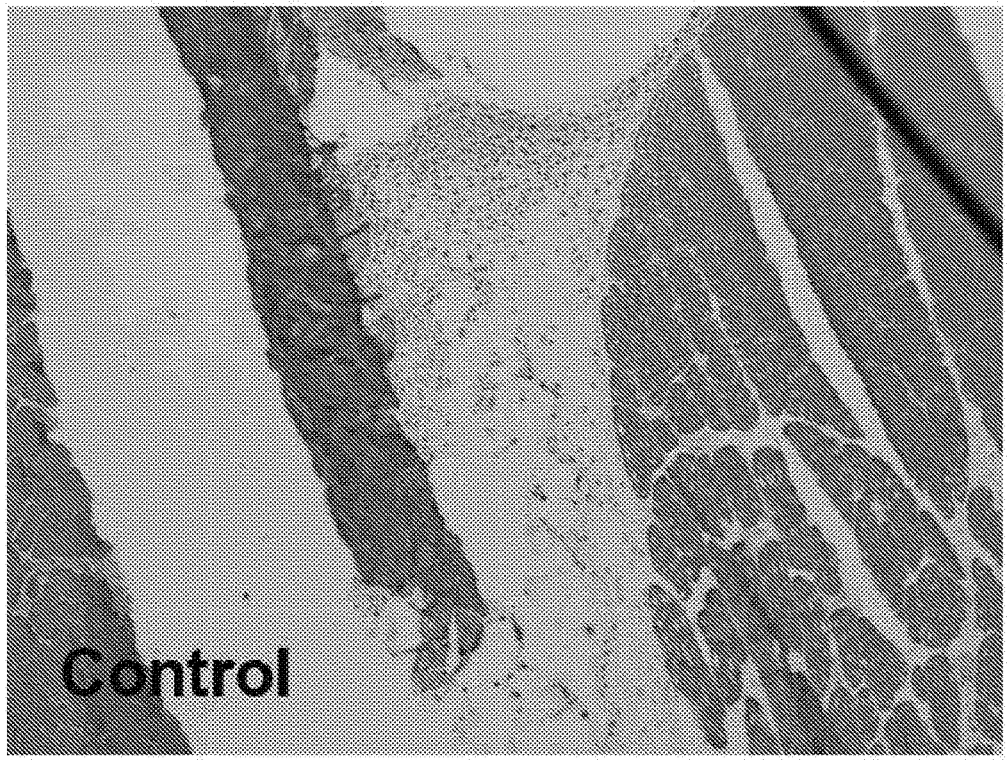
Figure 5C:
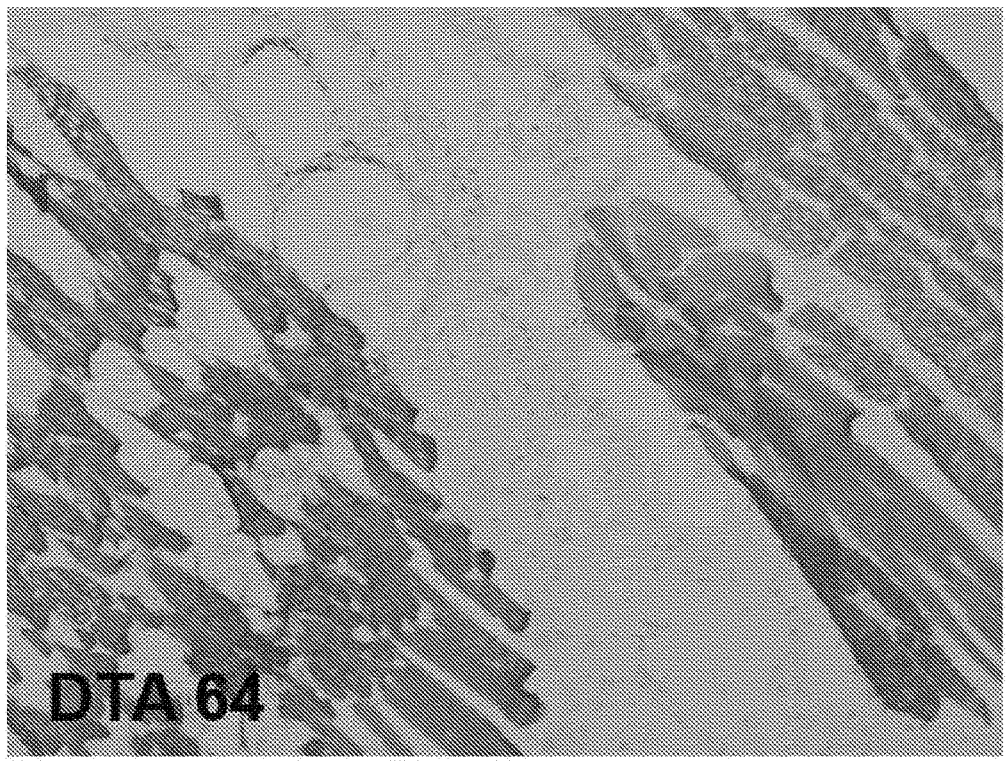
Figure 5D:
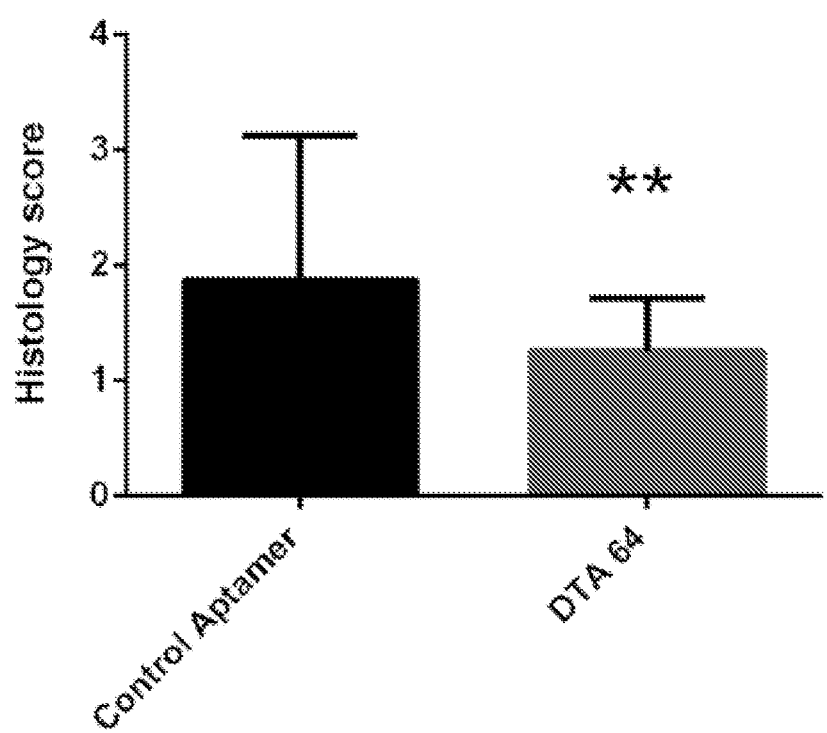
Figure 6:
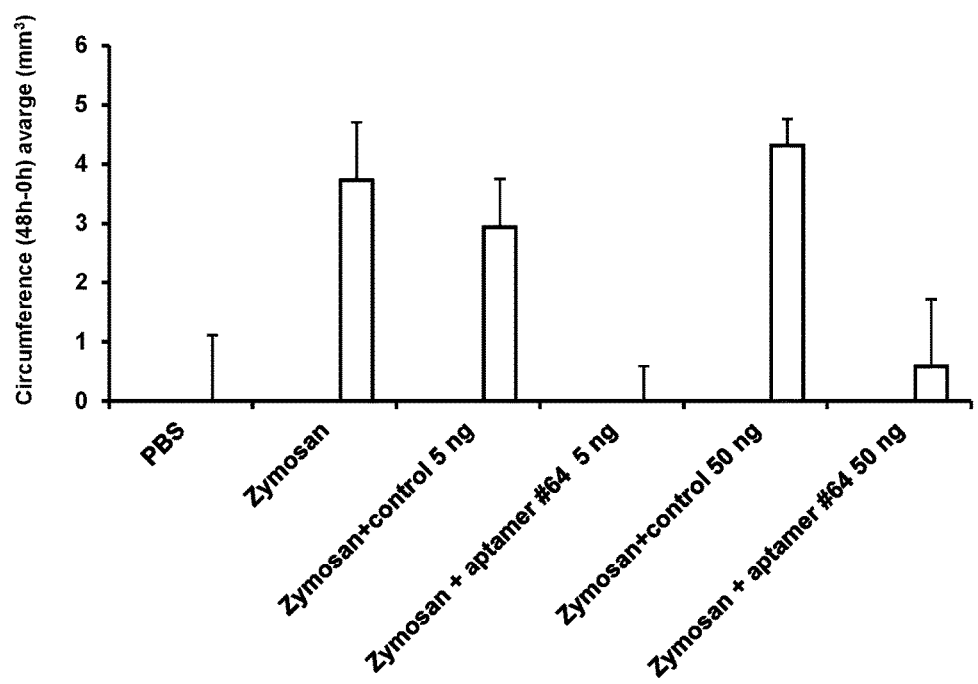
FIG. 6: Shows the effects of DEK aptamers on zymosan induction of joint inflammation.
Figure 7A:
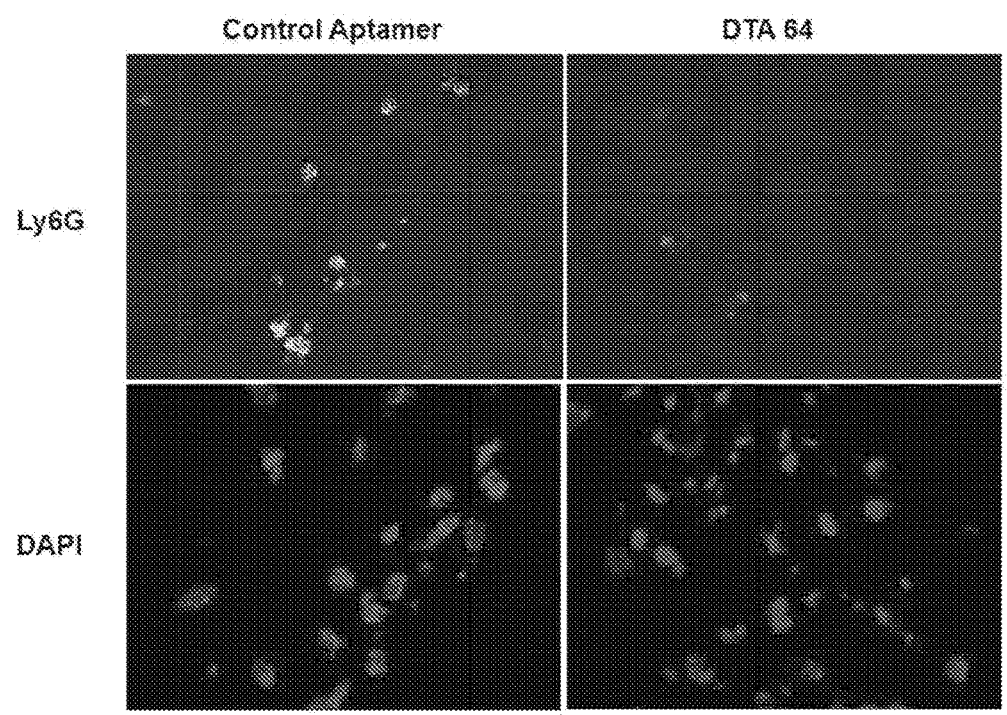
FIG. 7: Shows fluorescent immunohistochemistry staining of joint sections hours after intra-articular injection of either control or anti-DEK aptamer.
Figure 7B:
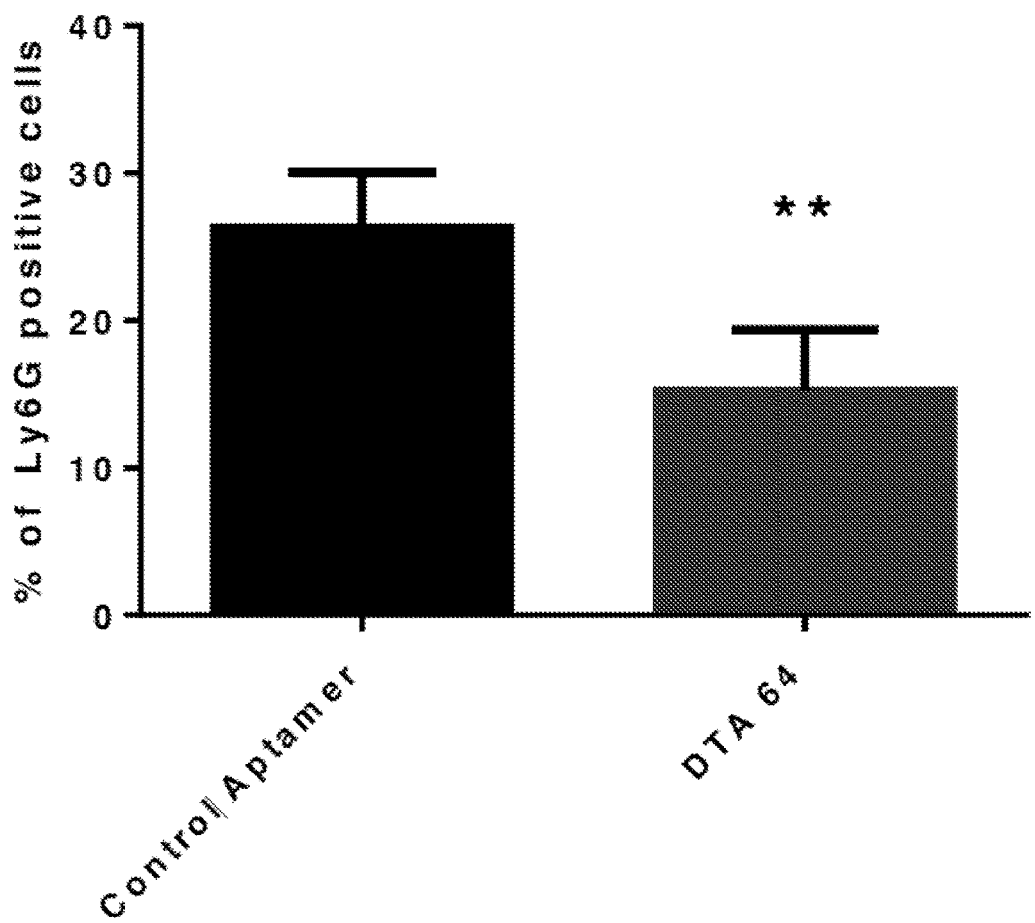

Anti-DEK aptamers were selected using SELEX technology and a single stranded DNA with a 40 nucleotide core flanked by 22 pre-determined bases on each side with high affinity for recombinant DEK protein (FIG. 1) (SEQ ID NO; 6) was tested. To measure its anti-inflammatory capabilities in vivo, it was injected into the knee joint 30 minutes before administration of zymosan; the contralateral knee of each mouse was injected with and equal volume (20 µl) of sterile saline, or with control aptamer (5 or 50 ng/knee) vs. DEK aptamer (5 or 50 ng/contralateral knee). As illustrated in FIG. 5A the contralateral knee was injected with an equal volume (20 µl) of sterile saline. The 12-13 week old mice (129/SVEV on B6) obtained from Jackson laboratory at age of 10 weeks were injected with aptamers 30-60 min before zymosan injection. Circumferences of the knees were measured 24 and 48 hours after injection as described above. Mice were sacrificed 48 hours after injection and knees were harvested for histology and pathological assessment. FIG. 6 shows mean values of increased knee circumference at 48 hours after injection. Measurements of mouse knee circumference at 48 hours demonstrated that administration of 5 ng of DEK aptamer plus zymosan led to almost no inflammation (0 mm$^3$±0.588) (*p=0.00074) (Student's T-test) compared to administration of 5 ng of library control aptamer (2.94 mm$^3$±0.8). Fifty ng of DEK aptamer reduced the inflammation in the knee to 0.58 mm$^3$ (±1.12) following zymosan injection (*p=0.0183). The DEK-targeting aptamer SEQ ID NO: 6 ("DTA 64") significantly reduced joint inflammation at 5 ng/knee (p=0.004), 50 ng/knee (p=0.0006) and 100 ng/knee (p=0.032) compared to control aptamers, as measured by knee circumference 48 hours after injection of aptamers and zymosan (FIG. 5B). Similar results were observed 24 hours after injection. Histopathological assessment of DEK-targeted vs. control aptamer-treated joints revealed an overall significant reduction in inflammatory cell migration in the presence of SEQ ID NO: 6 vs. control aptamer as determined by pathological assessment of H&E sections (FIG. 5C and FIG. 5D). Fluorescent immunohistochemistry staining revealed fewer Ly6G-positive cells in DTA64-treated knees (FIG. 7), similar to the phenotype of DEK-KO mice (see below). FIG. 7A shows joint sections analyzed for neutrophils by immunohistochemistry 48 hours after intra-articular injection of either control or anti-DEK aptamer using the murine neutrophil surface marker LY6-G. Cell nuclei are stained with DAPI. The magnification is 40×. FIG. 7B shows that joints injected with anti-DEK aptamers (i.e., "DTA 64") exhibit significantly lower numbers of Ly6G positive cells as compared to joints injected with control aptamer. Results shown reflect the percentage of Ly6G positive cells from 5 different fields from each joint section from 3 different mice. (*p=0.031 as determined by Students t-test.) In contrast, there was no significant difference in the infiltration of CD11b-positive cells. Accordingly, DEK-targeting aptamers neutralize neutrophil recruitment and the inflammatory response in the ZIA murine model, and protect mice from developing zymosan-induced knee inflammation. DEK-specific aptamer inhibits the development of inflammation in mouse knees induced by zymosan, compared to those mice treated with nonspecific control aptamers (i.e., random single strand DNA molecules of length comparable to DEK aptamers).

These results demonstrate that single-stranded anti-DEK DNA aptamers attenuate inflammation in WT mice subjected to ZIA.

Example 9

This example describes joint inflammation in wild-type (WT) mice compared to DEK knockout (KO) mice in the zymosan-induced arthritis (ZIA) model.

DEK knockout (KO) mice (129/SVEV on B6), were employed. Control mice were generated by back-breeding DEK-KO mice with the B6 WT strain for a minimum of 10 generations, bred as heterozygotes. Mice were housed in specific pathogen-free conditions at the Animal Maintenance Facility of the University of Michigan Medical Center, until they were used for experiments at 10-13 weeks of age.

Figure 8A:
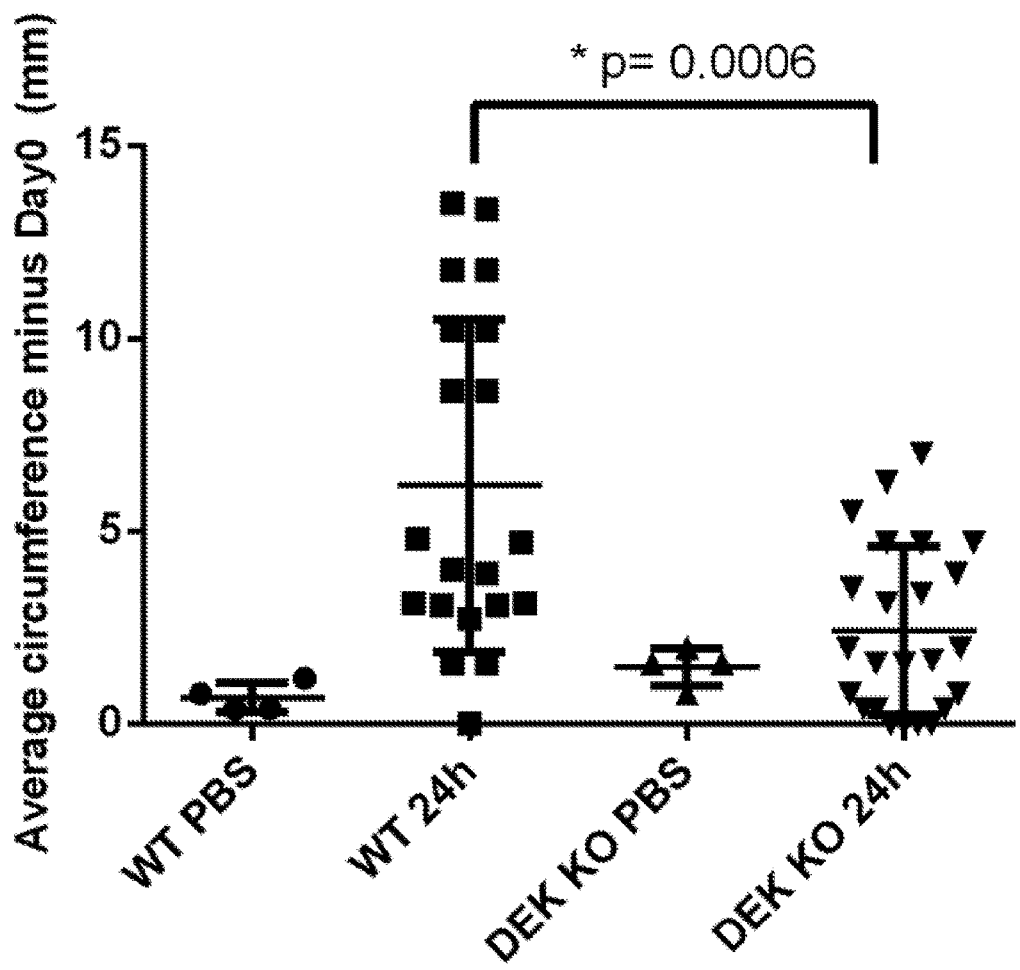
FIG. 8: Shows reduced knee circumference and levels of pro-inflammatory markers in DEK-KO mice.
Figure 8B:
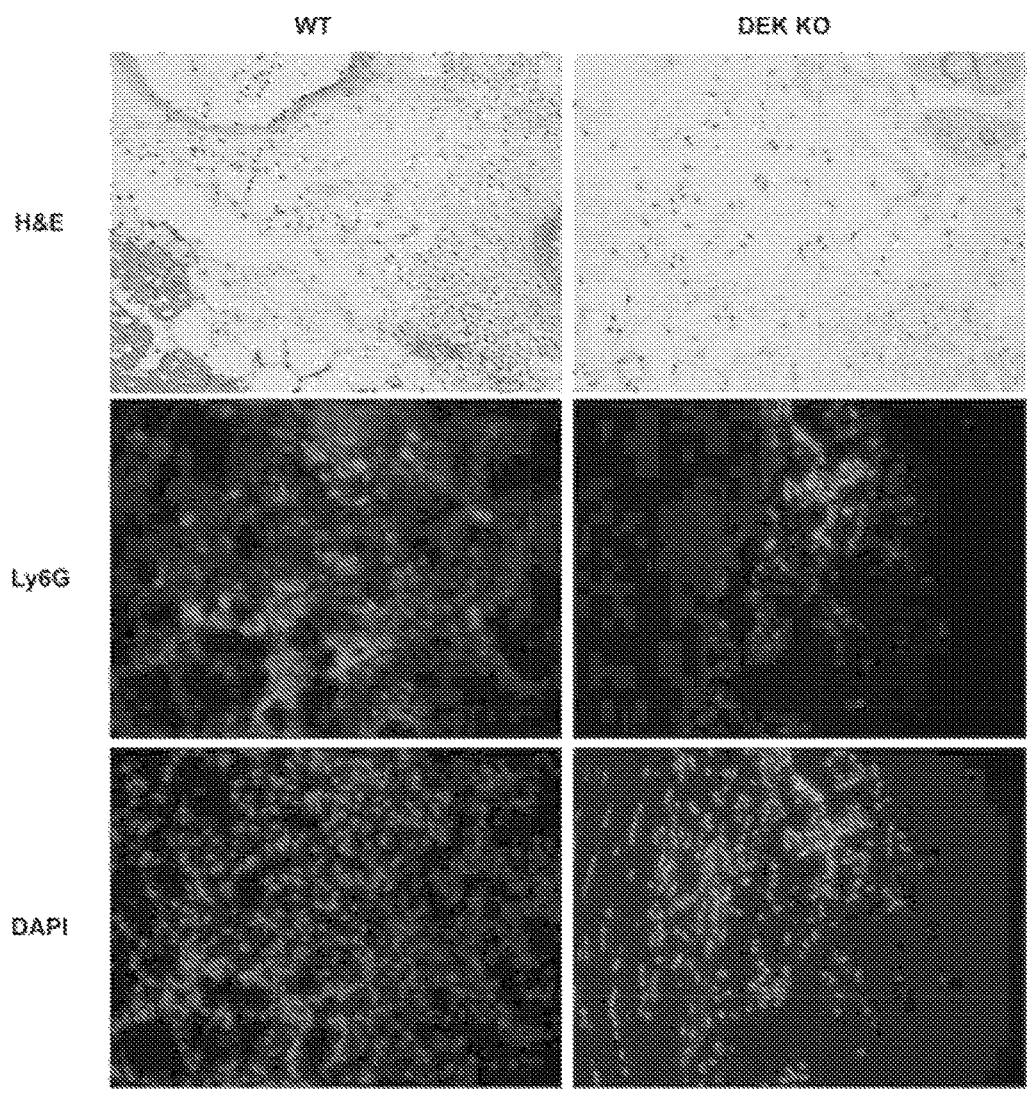
Figure 8C:
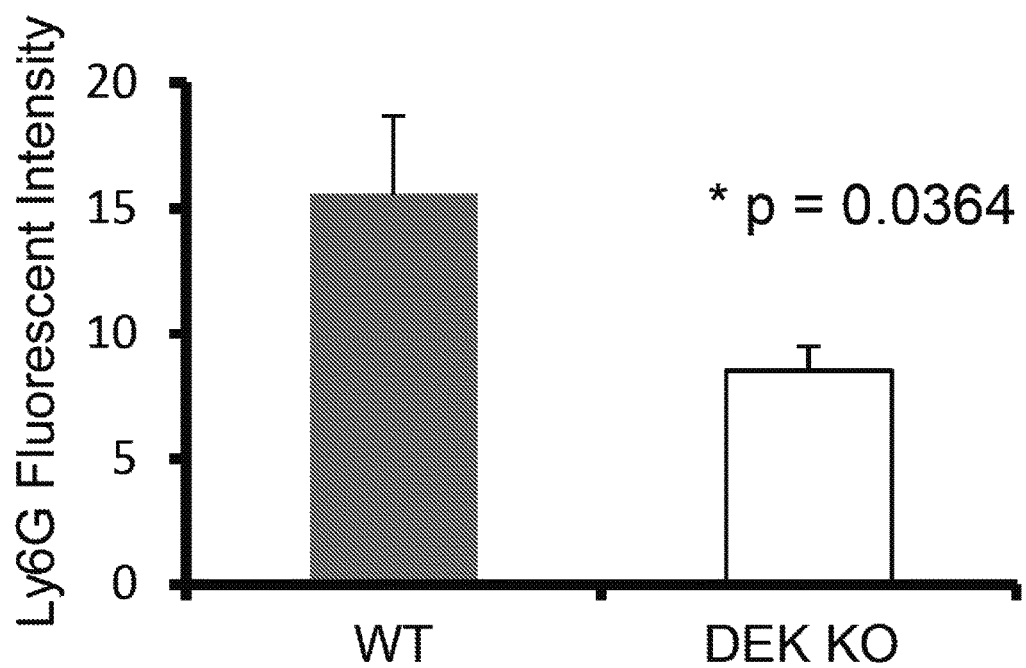
Figure 9:
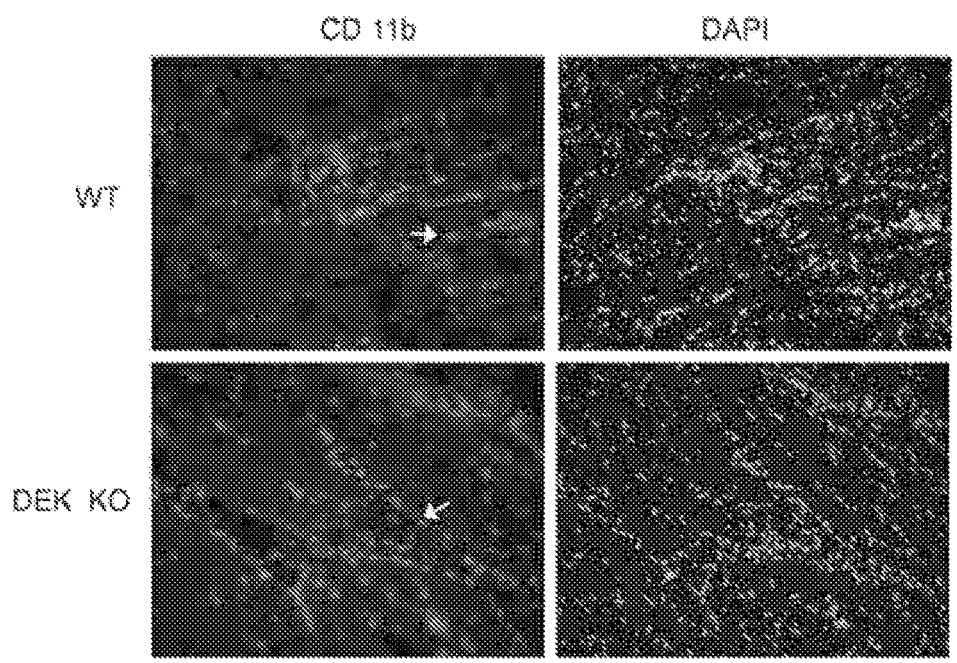
FIG. 9: Shows that monocyte migration in response to zymosan-induced arthritis is the same in WT and DEK-KO mice.

WT mouse knees were at least 2-fold larger (3.794 mm$^3$±0.412) than DEK-KO mouse knees (1.689 mm$^3$±0.282) 24 hours following zymosan injection (FIG. 8A; p=0.0006). Histopathologic analysis of total inflammatory cell infiltration by hematoxylin and eosin (H&E) staining of knee sections 24 hours post-injection demonstrated differences between DEK-KO and WT mice. Immunostaining for the myeloid marker CD11b showed no differences (FIG. 9). FIG. 9 shows that monocyte migration in response to zymosan-induced arthritis is the same in WT and DEK-KO mice. Joint sections from WT and DEK-KO zymosan-injected knees were analyzed for monocytes by immunohistochemistry 24 hours after intra-articular injection using the murine leukocyte/monocytic surface marker CD11b. Examples of positive cells are marked by arrows. Sections were also stained for cell nuclei with DAPI. The magnification is 40×. DEK-KO injected joints exhibit the same number of CD11b positive cells as do WT injected joints.

Together, these results demonstrate that genetic depletion of DEK confers protection against arthritis in a murine model of inflammatory arthritis.

Example 10

This example describes neutrophil extracellular trap (NET) induction in mouse bone marrow neutrophils.

To purify neutrophils from mouse bone marrow, harvested bone marrow was rinsed with 50 mL PBS prior to centrifugation at 500 g×5 min. The pellet was resuspended in 5 mL PBS and cells were layered on a discontinuous gradient of 1 mL Histopaque-1119 and 5 mL Histopaque-1083. Tubes were centrifuged at room temperature (without brake) at 700 g×30 min. All but the last 1.5-2 mL was removed, after which cells were rinsed with 50 mL PBS prior to repeat centrifugation at 500 g×5 min. Cells were resuspended in 5 mL PBS prior to being counted and prepared for immunohistochemistry as described above and below, with the exception that rather than a 1 hour incubation as for human neutrophils, the mouse neutrophils were incubated for of 2 hours with 1 µg/ml LPS to induce NETs.

Figure 10A:
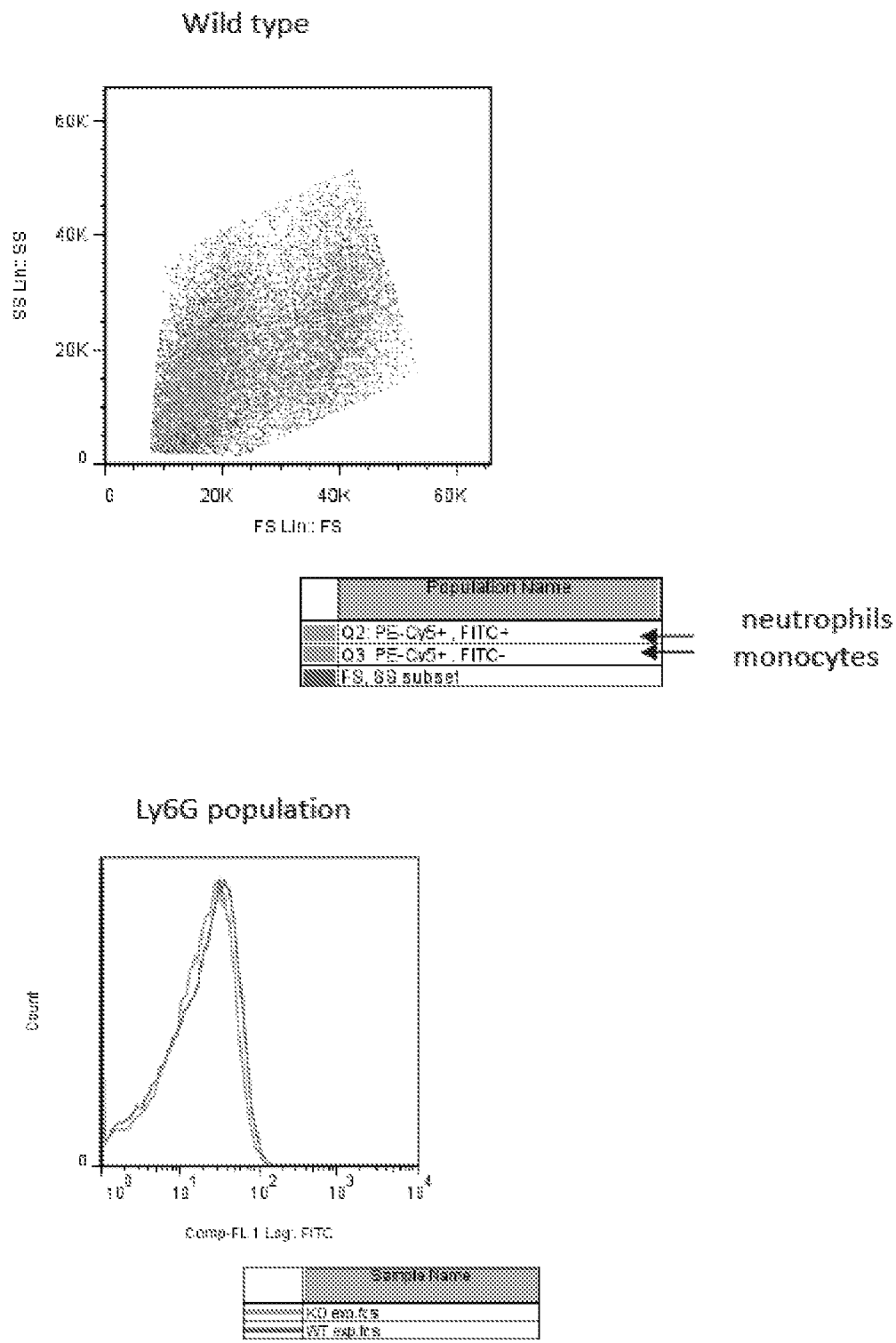
FIG. 10: Shows that neturophils from DEK-KO mice are mature by flow cytometery.
Figure 10B:
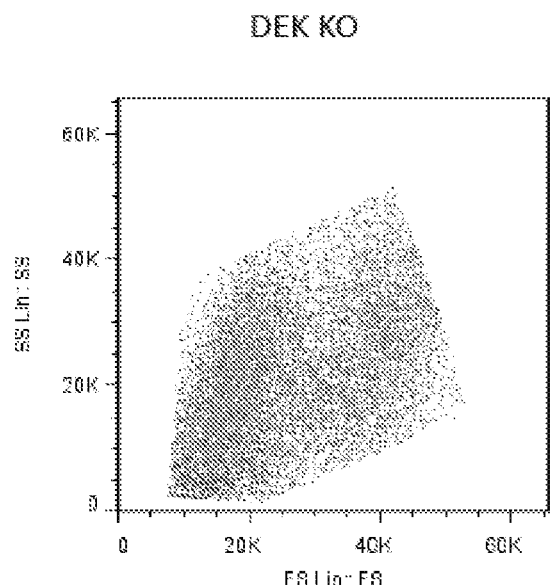
Figure 10B:
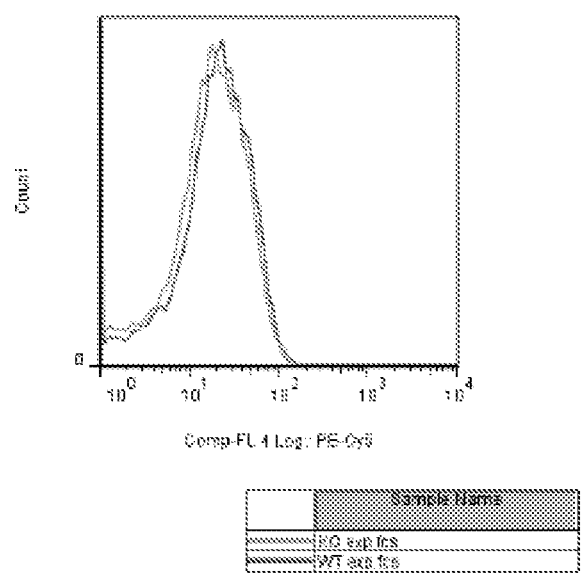
Figure 10C:
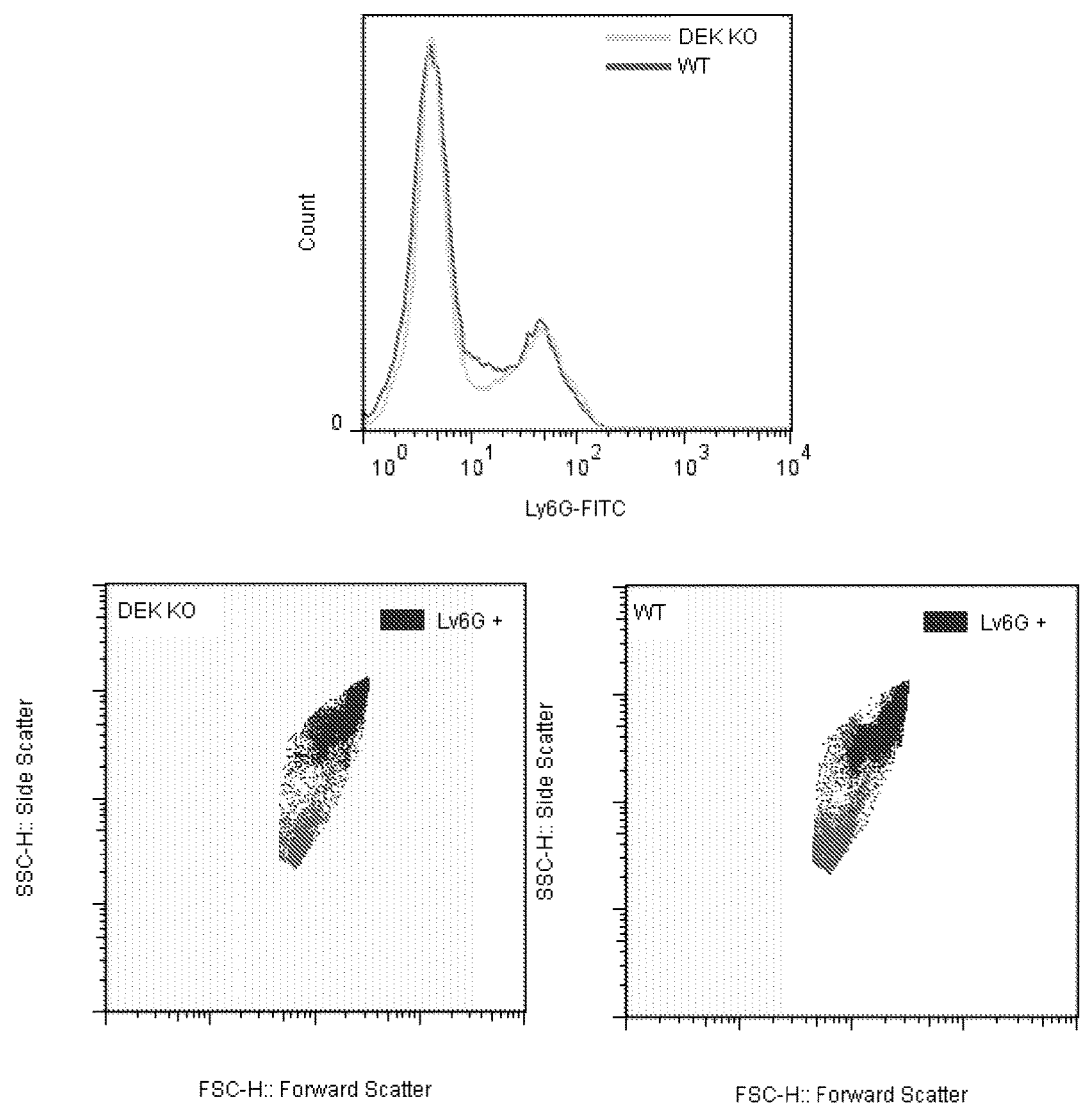
Figure 10D:
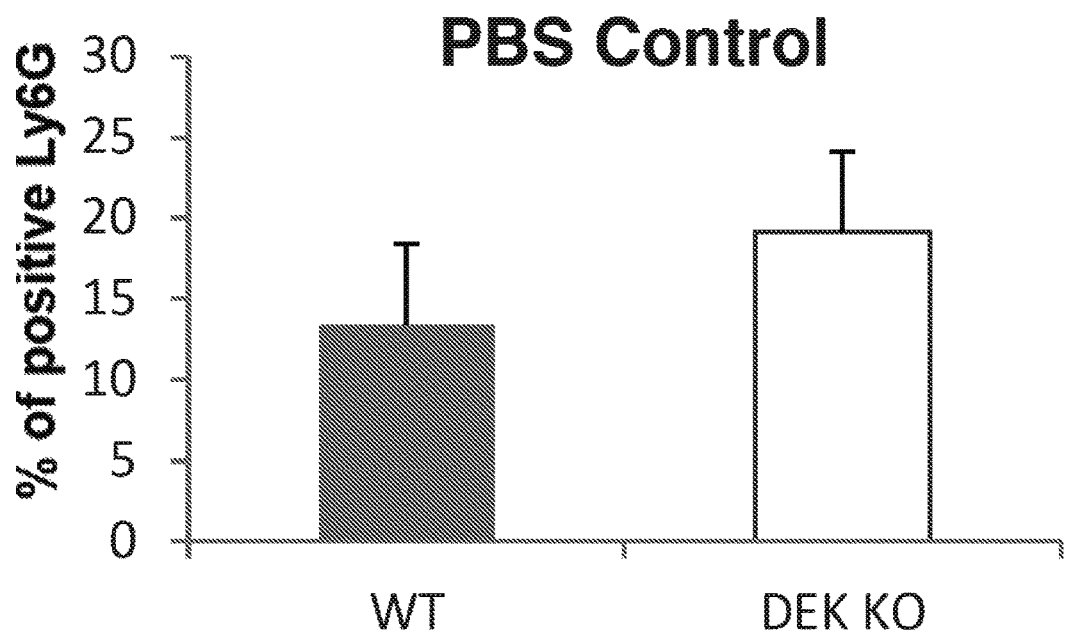
Figure 10E:
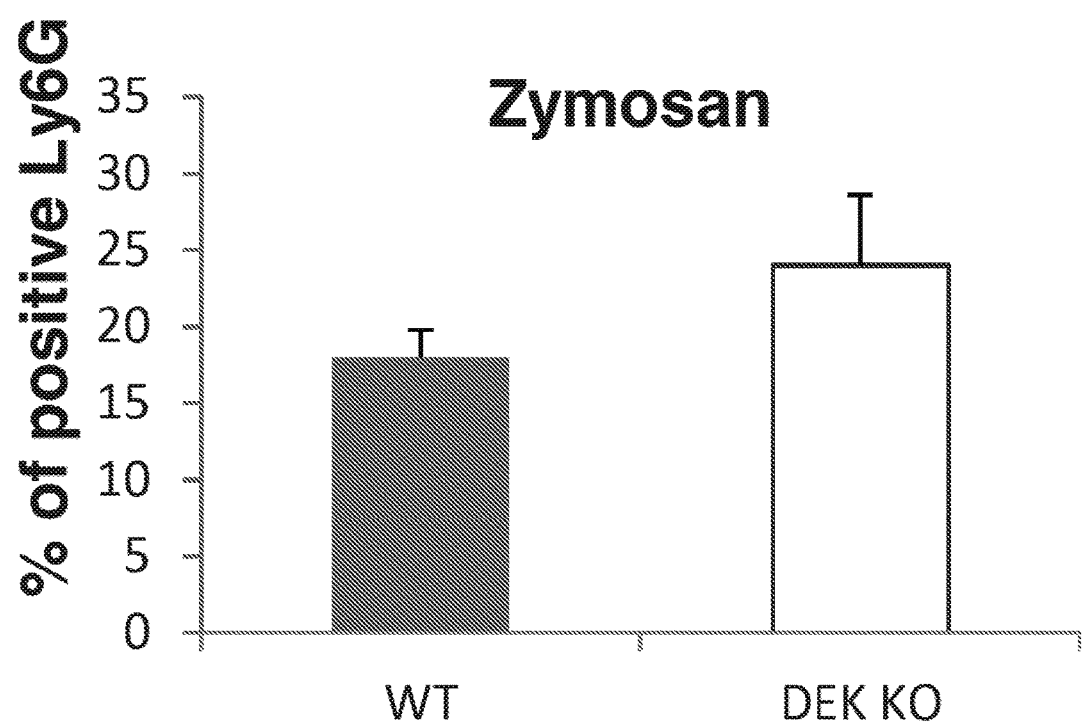
Figure 11A:
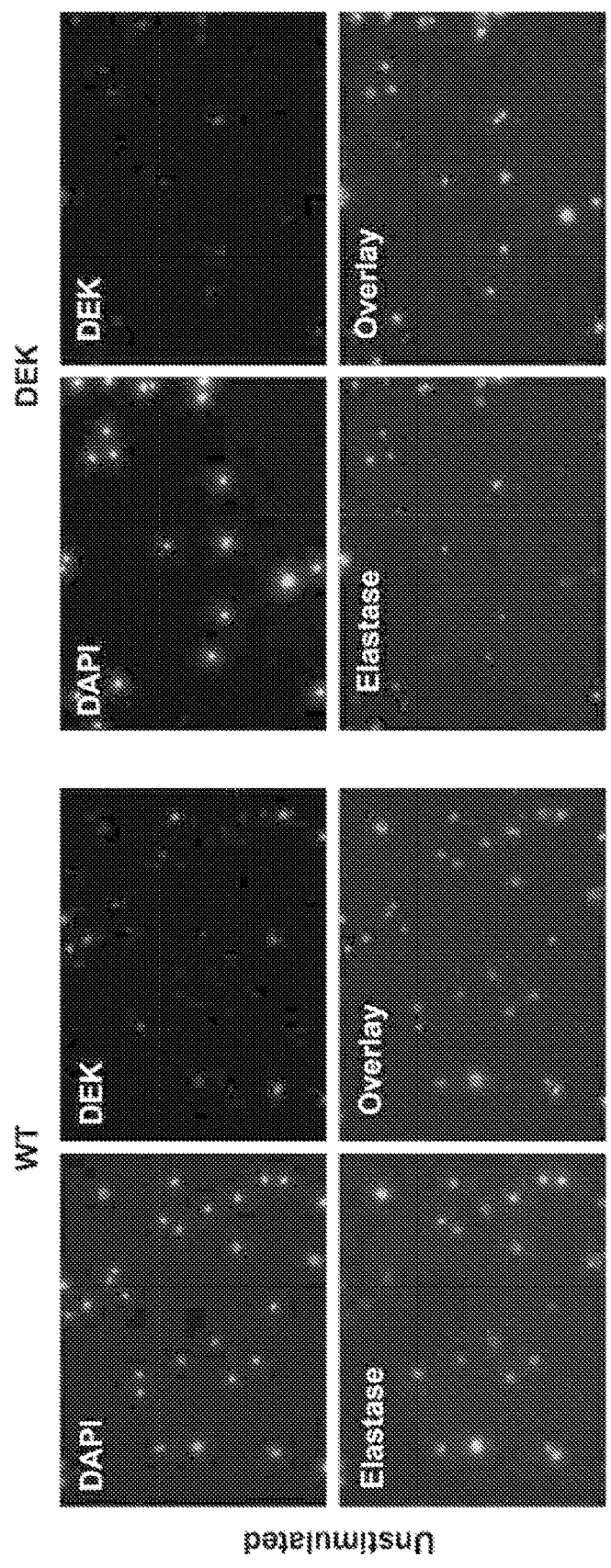
FIG. 11: Shows that neutrophils from DEK-KO mice demonstrate limited capacity to form NETs after LPS stimulation as detected by extracellular co-localization of DAPI and anti-elastase antibody, when compared to neutrophils from WT mice.
Figure 11B:
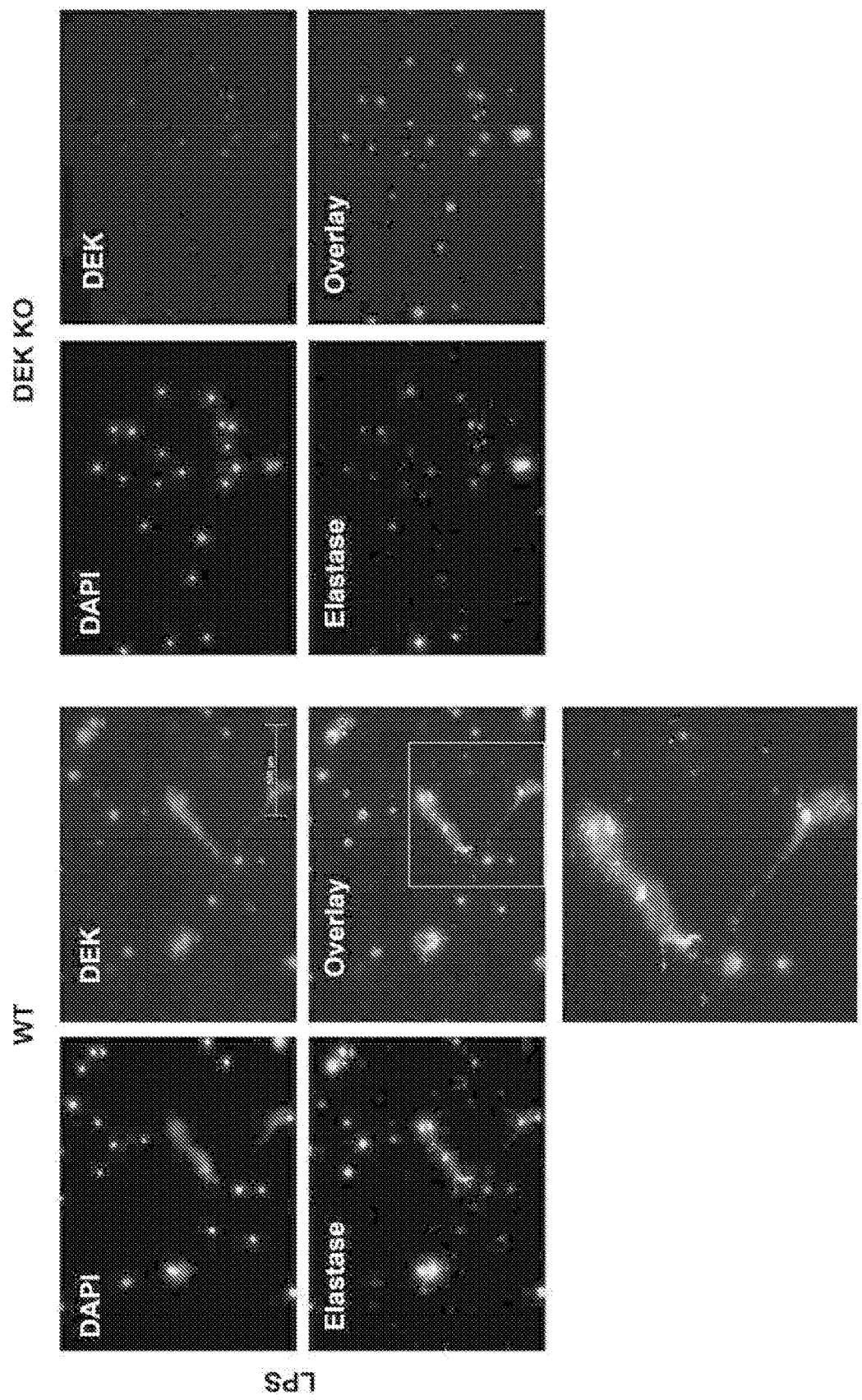
Figure 11C:
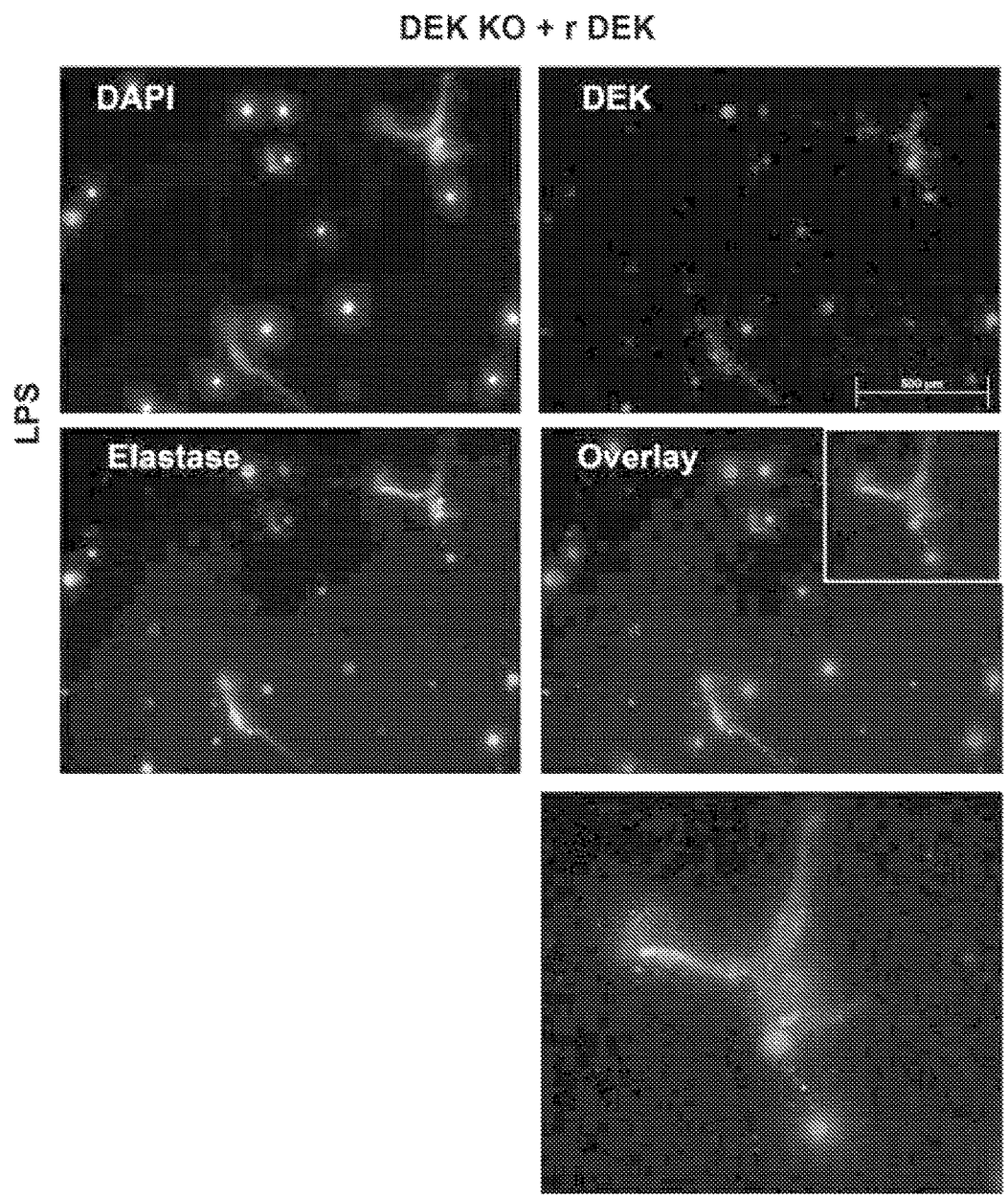
Figure 11D:
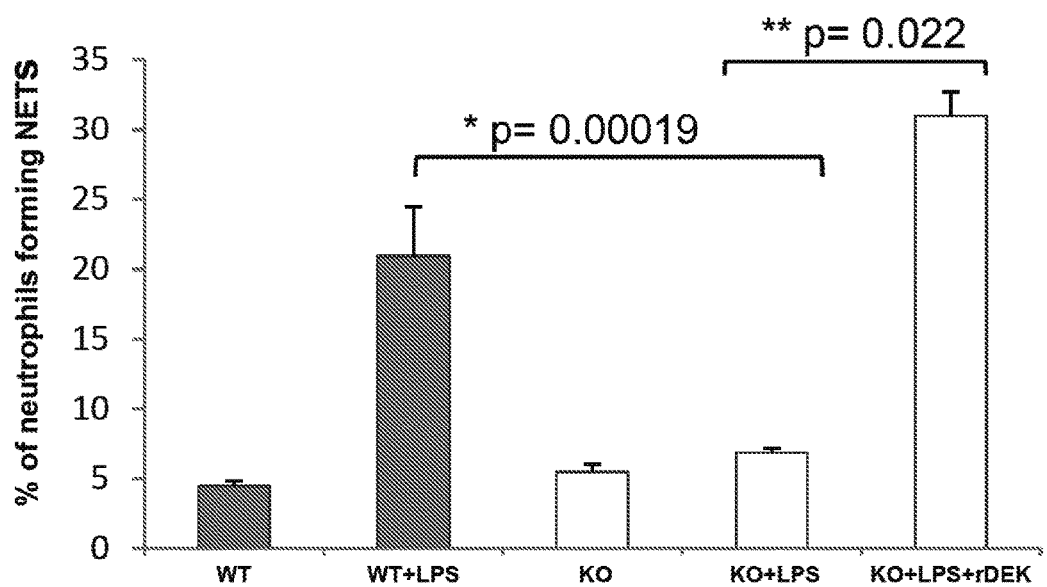
Figure 12A:
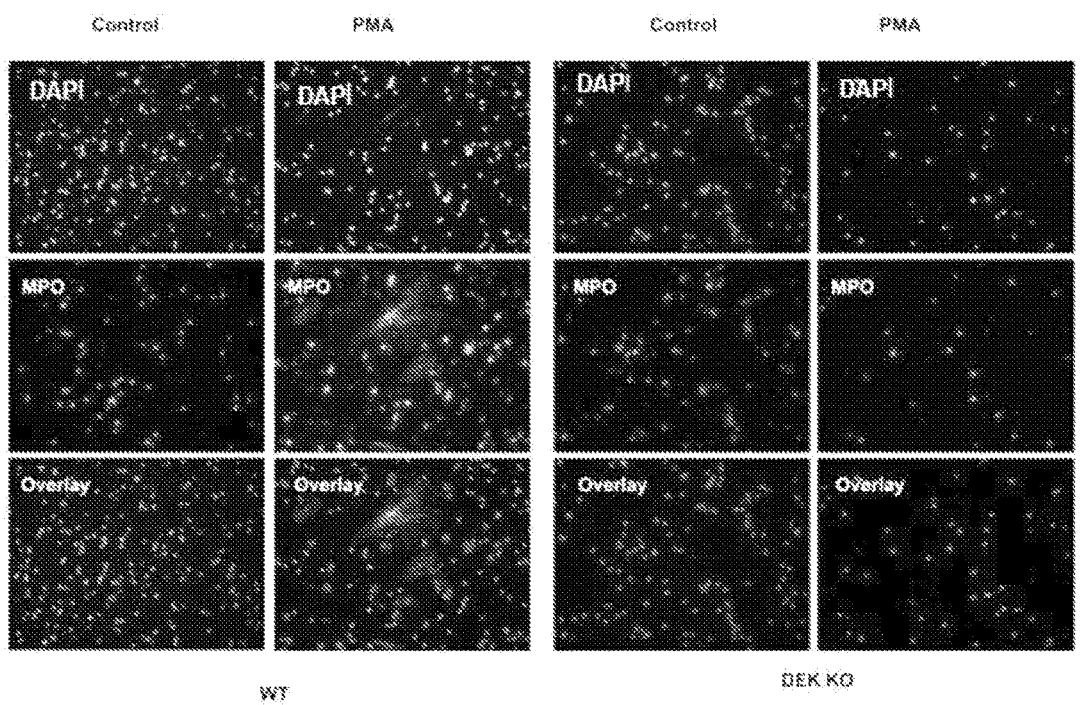
FIG. 12: Shows that minimal NET formation is observed after long-term stimulation of DEK-KO neutrophils.
Figure 12B:
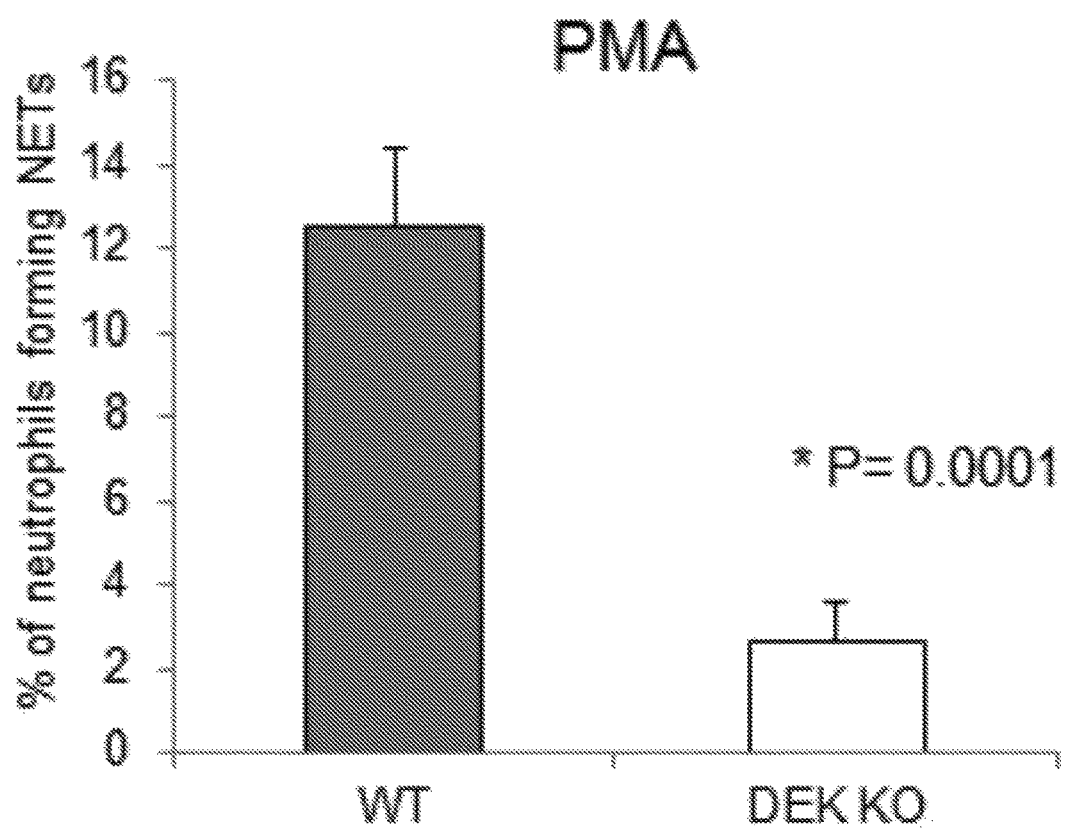

Purified and stimulated neutrophils from the bone marrow of DEK-KO and WT mice were tested for their capacity to generate NETs in vitro. Purity of bone marrow neutrophils from both WT and DEK-KO mice was confirmed by CD11b and Ly6G staining (FIG. 10A and FIG. 10B). Staining for the neutrophil marker Ly6G revealed a significantly reduced neutrophil infiltration in DEK-KO mice as compared to WT mice (FIG. 10A and FIG. 10B). FIG. 10 shows flow cytometry analysis of neutrophils purified from bone marrow of WT (A) and DEK-KO (B) mice using Ly6G-FITC (neutrophils) and CD11b-ECy5 (found on neutrophils and monocytes). No difference in expression of Ly6G in DEK-KO neutrophils was observed when compared to WT as shown by dot plots and histograms. Moreover, no differences in neutrophil nuclear morphology or spontaneous NET formation were observed in unstimulated neutrophils from WT vs. DEK-KO mice (FIG. 11A). However, neutrophils from DEK-KO mice demonstrated limited capacity to form NETs after LPS stimulation, as detected by extracellular co-localization of DAPI and anti-elastase antibody, when compared to neutrophils from WT mice (FIG. 11B and FIG. 11 D; p=0.00019). Parallel observations were noted after phorbol myristate acetate (PMA) activation of neutrophils from DEK-KO and WT mice was extended for up to 8 hours (FIG. 12). FIG. 12 shows that minimal NET formation is seen even after long-term stimulation of DEK-KO neutrophils. FIG. 12A shows neutrophils purified from the bone marrow of WT and DEK-KO mice. Neutrophils were stimulated with PMA for 8 hours and then fixed and stained with MPO (1:500, Dako) and DAPI. No formation of fully-developed NETs was detected from the stimulated DEK-KO cells. WT neutrophils readily generated NETs. FIG. 12B shows the percentage of PMA-stimulated neutrophils with NETs seen in 10 different fields of WT and DEK-KO cells as counted by two independent individuals. Although altered neutrophil development may contribute to the lessened neutrophil-specific response exhibited by DEK-KO mice, bone marrow and peripheral blood neutrophil counts (see below) by Ly6G staining displayed no differences between DEK-KO and WT mice (FIG. 10).

These results demonstrate that neutrophils from DEK-KO mice have reduced capacity to form NETs after short-term and long-term stimulation with PMA.

Example 11

This example describes neutrophil extracellular trap (NET) induction in mouse peripheral blood neutrophils.

Figure 13A:
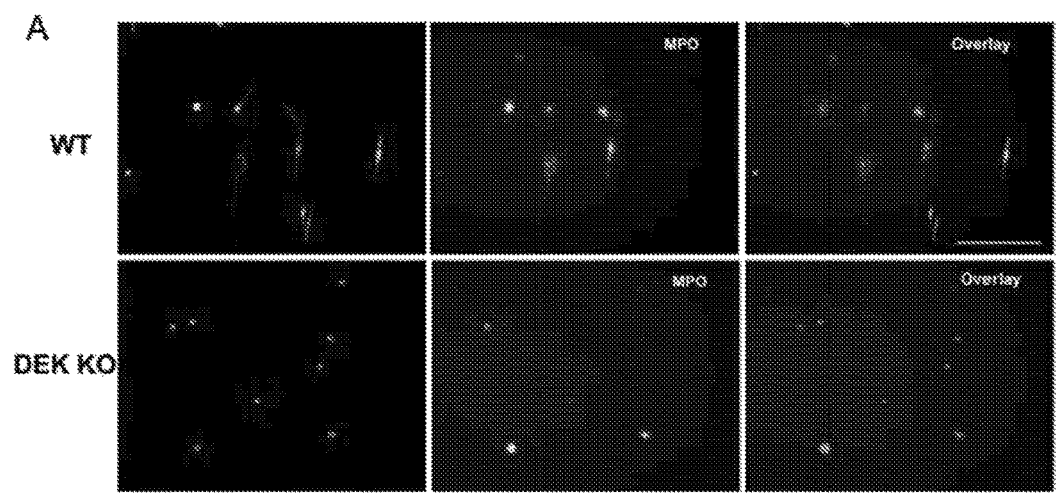
FIG. 13: Shows that mouse peripheral blood neutrophils from DEK-KO mice form fewer NETs in response to stimulation than do peripheral blood neutrophils from WT mice.
Figure 13B:
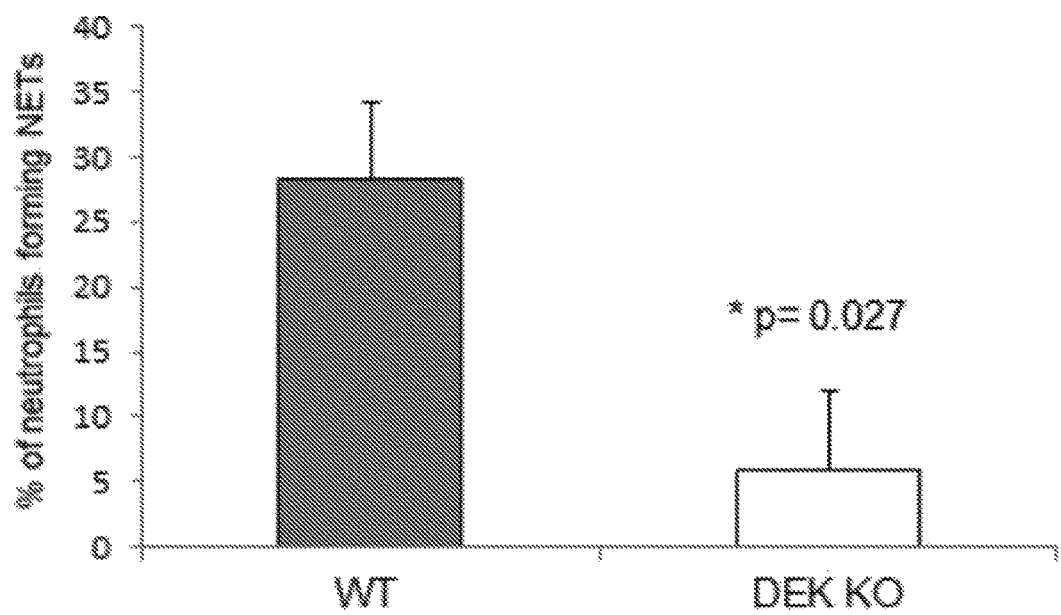

Blood was obtained from WT and DEK-KO mice by cardiac puncture under terminal anesthesia. Blood was collected into heparinized tubes (500 U/1 ml blood). Cells were isolated by Histopaque 1083 in 1:1 ratio in 15 ml tubes. Neutrophils were recovered from the red blood cell (RBC) fraction in the bottom of the tube by 20% dextran solution (half the volume of the RBC), mixed, and RBCs allowed to sediment for 10 min at room temperature. Leukocyte-rich supernatant was collected from the top fraction and washed twice by 8 ml 0.2% BSA in PBS by centrifugation (1500 RPM). Red blood cells were lysed with 2 ml RBC lysis buffer (BioLedgened) for 4 min on ice followed by 10 ml PBS wash. 1-2×10$^6$ cells were plated on coverslips (as described above for isolation of neutrophils from human blood) in RPMI with 2% BSA and stimulated with 1 ng/ml PMA for 2 hours. FIG. 10C shows a representative flow cytometry histogram of whole blood cells obtained from WT and DEK-KO mice using Ly6G-FITC. No difference in expression of Ly6G was detected in DEK-KO v.s WT peripheral blood. FIG. 10D. and FIG. 10E show the percentage of Ly6G positive cells in peripheral blood of WT and DEK-KKO mice 24 hours after the received intraarticular injections with (FIG. 10D) PBS control or (FIG. 10E) zymosan from 3 different WT or KED-KO mice. Reports demonstrate that aberrant granulocyte differentiation results from DEK knockdown in CD34+ human bone marrow cells (Koleva, R. I. et al. C/EBPalpha and DEK coordinately regulate myeloid differentiation. *Blood* 119, 4878-4888, doi:10.1182/blood-2011-10-383083 blood-2011-10-383083 [pii] (2012). Findings in peripheral blood neutrophils were similar to those from bone marrow neutrophils from DEK-KO mice (FIG. 13) i.e., DEK-KO neutrophils are unable to form NETs both in vivo and in vitro. FIG. 13 shows that mouse peripheral blood neutrophils from DEK-KO mice form fewer NETs in response to stimulation than do peripheral blood neutrophils from WT mice. FIG. 13A shows mmuno-staining of peripheral blood neutrophils purified from DEK-KO and WT mice after 2 hour stimulation with 1 ng/ml PMA. Neutrophils were fixed and stained by MPO and DAPI. The magnification is 40×. WT neutrophils show NET formation as expected after PMA stimulation, but minimal NET formation is detected in the stimulated DEK-KO neutrophils as indicated by MPO and DAPI. FIG. 13B shows the percentage of neutrophils that formed NETs after PMA stimulation as calculated from 5 different fields of WT and DEK-KO peripheral blood neutrophils. Reconstitution with recombinant DEK protein one hour prior to activation with LPS rescued the ability of DEK-KO neutrophils to generate NETs (FIG. 11C and FIG. 11D). These results demonstrate that addition of recombinant DEK allows DEK-KO neutrophils to create fully-formed NETs without entry of DEK into the cytoplasm or the nucleus.

Example 12

This example describes $H_2O_2$ generation in mouse bone marrow derived macrophages.

Bone marrow macrophages (BMM) from WT and DEK-KO were plated on 96-well plates. Secretion of $H_2O_2$ was determined colorimetrically using Amplex Red reagent (Molecular Probes, Eugene, Oreg.) according to the instructions of the manufacturer and as previously described (Serezani, C. H., Aronoff, D. M., Jancar, S., Mancuso, P., and Peters-Golden, M. (2005). Leukotrienes enhance the bactericidal activity of alveolar macrophages against *Klebsiella pneumoniae* through the activation of NADPH oxidase. Blood 106, 1067-1075.). Briefly, a solution containing 50 uM Amplex Red reagent and 10 U/mL HRP was prepared in PBS, and 0.1 mL of the suspension was added to BMM cultures (5×10$^5$ per well). Cells were incubated at 37° C. for 60 min. $H_2O_2$ concentrations in the culture media were determined using a standard curve generated with known $H_2O_2$ concentrations with a detection limit of 0.625 nM. Samples were measured at Å560 nM wavelength using a Tecan GENios plate reader (Phenix, Australia).

Figure 14A:
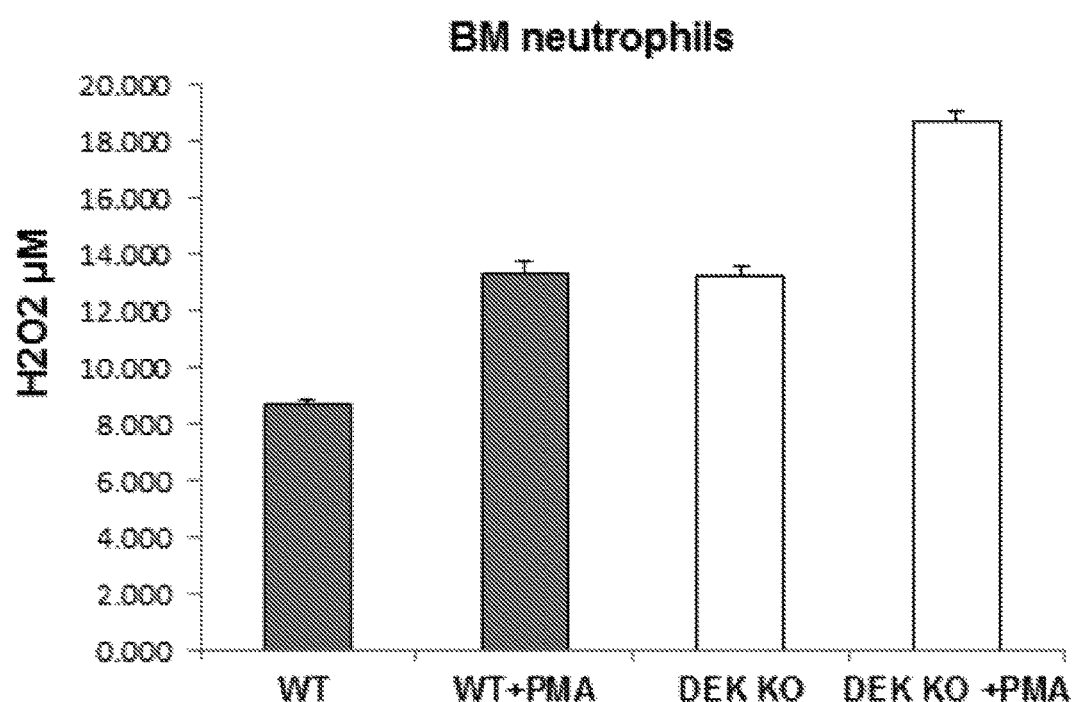
FIG. 14: Shows that peripheral and bone marrow neutrophils from DEK-KO mice express reactive oxygen species (ROS) to the same extent as do those from WT mice before and after PMA stimulation.
Figure 14B:
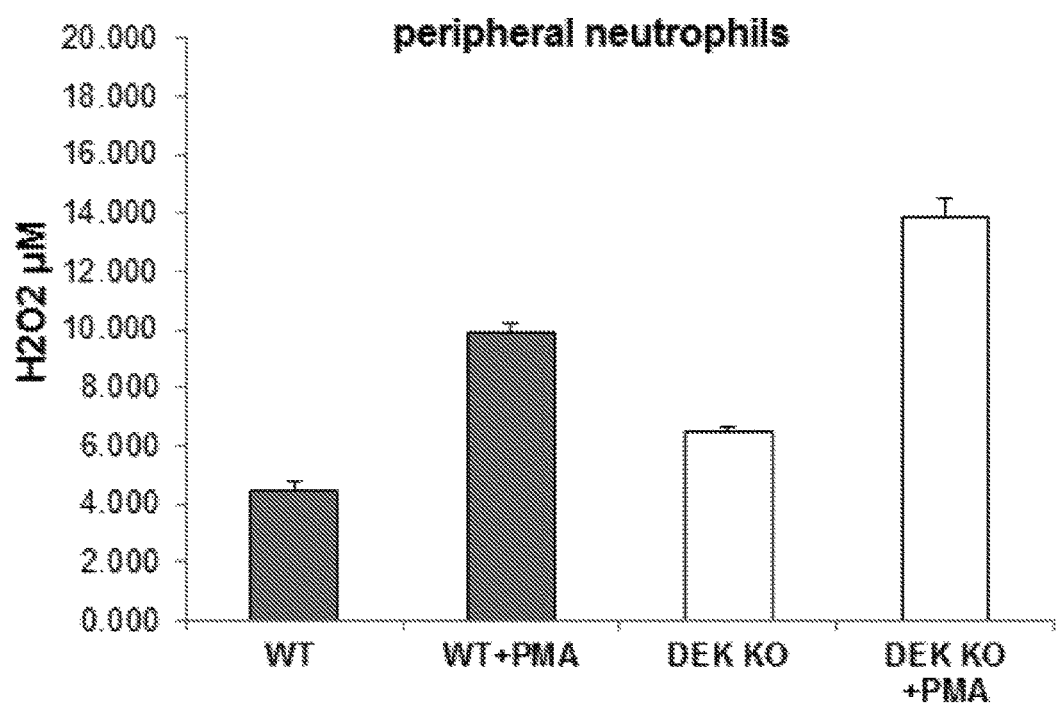

The observed defect in NET formation in the absence of DEK was not explained by a reactive oxygen species (ROS) driven mechanism; no difference in $H_2O_2$ generation was noted between DEK-KO and WT mice (FIG. 14A and FIG. 14B). FIG. 14 shows that peripheral and bone marrow neutrophils from DEK-KO mice express ROS to the same extent as do those from WT mice before and after PMA stimulation. FIG. 14A bone marrow and FIG. 14B peripheral blood neutrophils obtained from DEK-KO and WT mice were incubated with or without PMA (1 ng/ml) prior to determining H2O2 concentration in the supernatants. Data shown represent 2 independent experiments performed in triplicate.

Example 13

This example describes inflammatory cytokines within mouse knee homogenates.

Knees were skinned prior to freezing at −80° C. Frozen knees were homogenized in 0.5 ml of cold PBS, and then centrifuged at 14,000×g for 10 min at 4° C. Supernatants were collected and analyzed for protein concentration and for levels of mouse IL-1α, IL-1β, TNF-α, IL-12p70, IL-12 p40, IL-23, RANTES (Regulated on Activation Normal T cell Expressed and Secreted), MIP-2, IL-10, MCP-1, IFNγ, and TGFβ using ELISA. Splenocytes were purified as previously described (Zhang, M., Berndt, B. E., Chen, J. J., and Kao, J. Y. Expression of a soluble TGF-beta receptor by tumor cells enhances dendritic cell/tumor fusion vaccine efficacy. *J Immunol* 181, 3690-3697, 2008.), and TLR2 was detected by monoclonal anti-TLR2-FITC (Imegenex, IMG-6320C). Ficoll-purified bone marrow of WT control mice and DEK-KO mice or whole blood samples were resuspended in 1% BSA and 1% horse serum in PBS. Samples were spun at 1600 rpm for 5 min at 4° C. Cell pellets were resuspended with anti-Ly6G-FITC and or anti-CD11b-PE-Cy5 (BD Pharmingen, #553312) antibodies and incubated on ice for 30 min. Isotype-matched IgGs were used as negative control antibodies. Samples were centrifuged at 1600 rpm for 5 min at 4° C. and fixed with 2% paraformaldehyde. Cell surface markers were analyzed by FACS. cDNA was prepared from WT and DEK-KO knee joint tissue that was collected 24 hours after zymosan injection. TLR2 levels were assessed as part of a cytokine PCR array (SABiosciences QIAGEN, # MCA, CA).

Figure 8D:
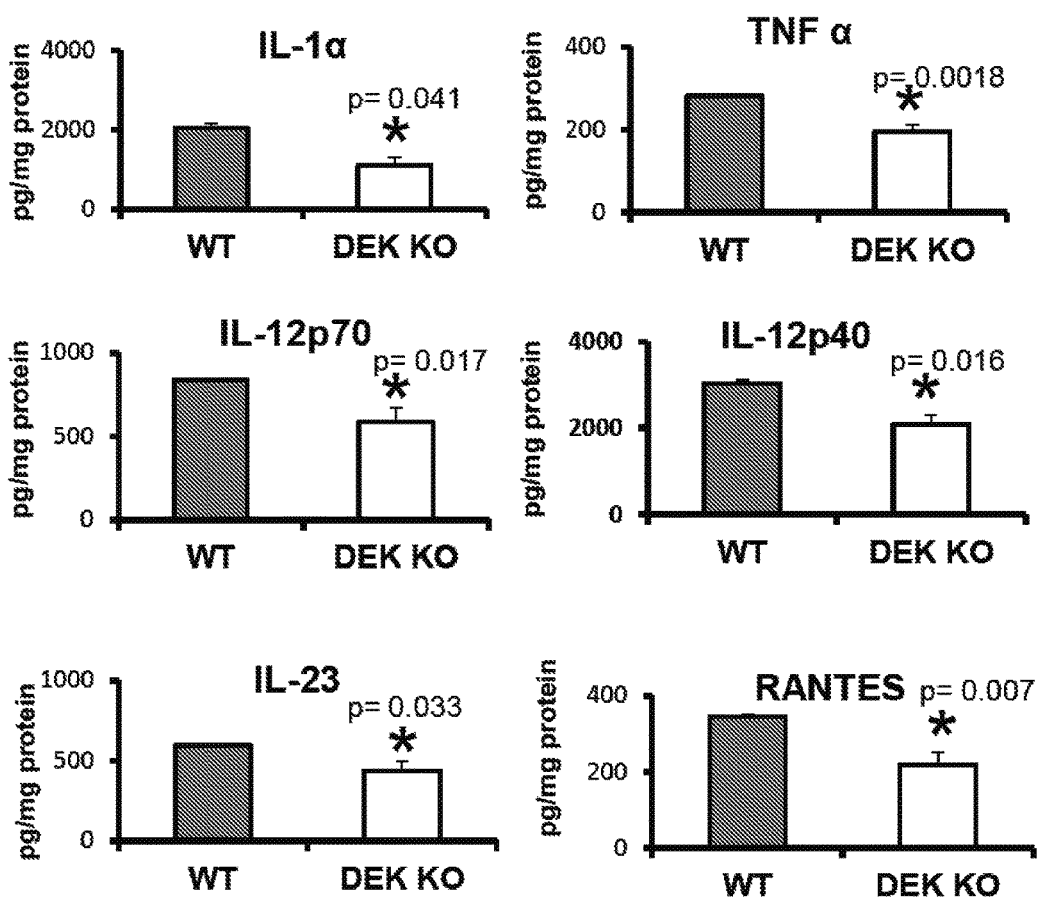
Figure 15A:
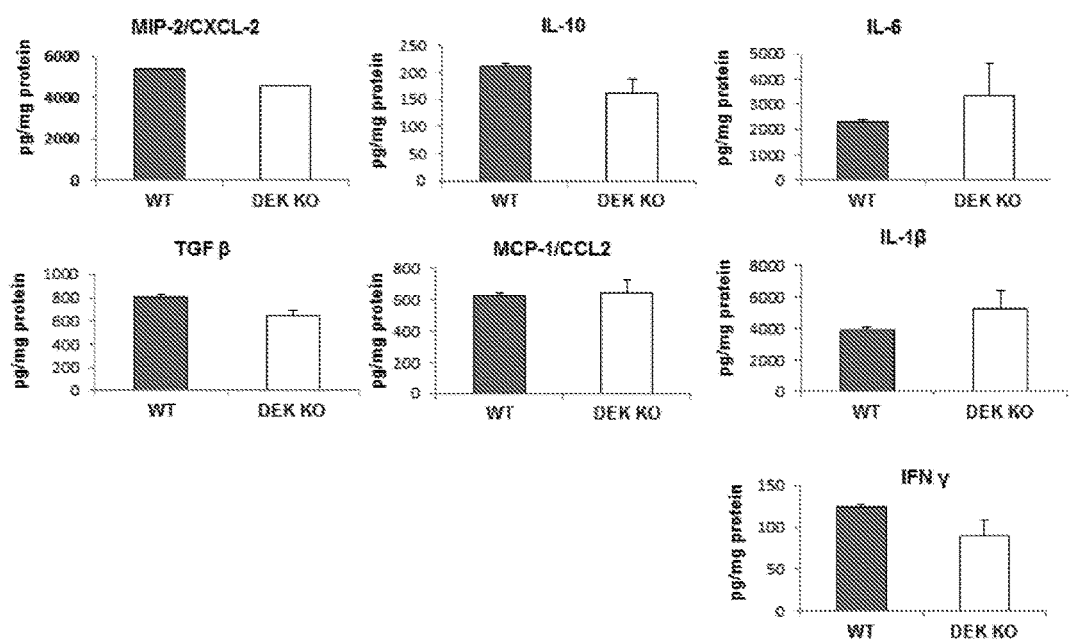
FIG. 15: Shows no difference in expression of certain pro-inflammatory cytokines and TRL2 in DEK-KO vs. WT mice.

In DEK-KO mice, levels of interleukin-1α (IL-1α), tumor necrosis factor-α (TNF-α), IL-12p40, IL-12p70, IL-23, and regulated on activation normal T cell expressed and secreted (RANTES) were all significantly reduced in knee homogenates from DEK-KO mice 24 hours post-injection as compared to WT counterparts (FIG. 8D). In contrast, other inflammatory cytokines did not display significant differences (FIG. 15A). FIG. 15 shows that no significant differences in expression of certain pro-inflammatory cytokines and TLR2 between DEK-KO vs. WT mice were observed. FIG. 15A shows no significant difference in IL-6, IL-1β, MIP-2, IL-10, IFN-γ, TGF-β and MCP-1 levels in knee homogenates of WT and DEK-KO mice after zymosan injection. Cytokine levels were analyzed by ELISA and normalized by protein concentration.

Figure 15B:
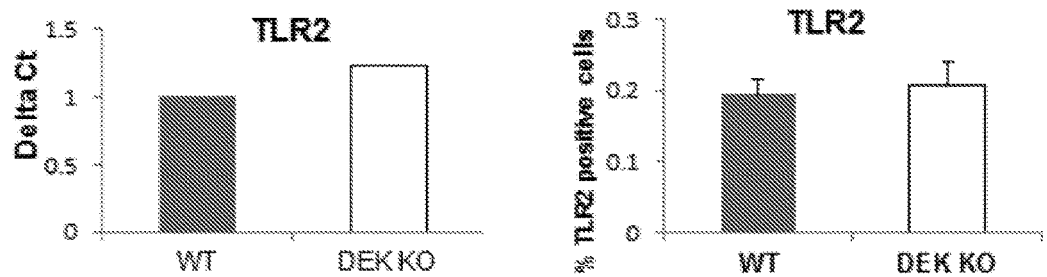
Figure 16:
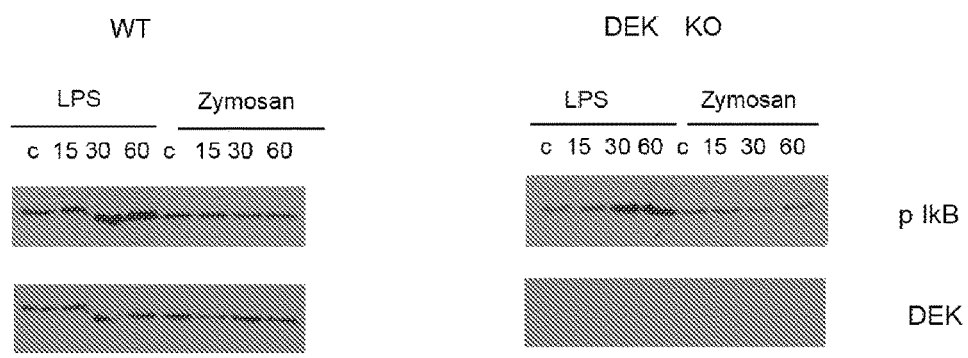
FIG. 16: Shows that DEK-KO and WT cells exhibit similar NF-κB signaling after stimulation.

To test if the difference in inflammatory responses between WT and DEK-KO mice is due to differences in cell signaling, the expression levels of the cell surface receptor for zymosan, toll-like receptor 2 (TLR2) was analyzed. TLR2 mRNA and protein levels in knee homogenates and cells purified from WT spleens did not differ from expression detected in DEK-KO mice (FIG. 15B). FIG. 15B shows that TLR2 levels of expression are similar in DEK-KO and WT mice. cDNA was prepared from WT or DEK-KO zymosan-injected knees and qPCR was used to determine TLR2 RNA levels, which showed no significant differences (left panel). TLR2 levels were also measured by flow cytometry of cells isolated from naïve WT and DEK-KO spleens (right panel). Low levels of TLR2 were detected, but no difference in TLR2 expression was observed consistent with the RNA data shown in the left panel. Moreover, NF-κB, a regulator of inflammatory cytokines, was not differentially regulated in DEK-KO vs. WT bone marrow macrophages and neutrophils upon in vitro stimulation with LPS or zymosan (FIG. 16). FIG. 16 shows that bone marrow-derived macrophages collected from WT and DEK-KO mice were stimulated with 1 μg/ml LPS or Zymosan for the indicated times. Levels of phosphorylated IκB (p IκB) were analyzed in the cytosolic fraction. DEK-KO mice develop significantly less inflammation compared to WT mice in the setting of ZIA as measured by marked changes in joint circumference and cytokine profile, and a decrease in neutrophil migration. These effects are not due to differences in neutrophil development or cell signaling events.

These results demonstrate that homogenates of zymosan-injected joints from DEK-KO vs. WT mice had significantly lower levels of inflammatory cytokines such as IL-1α, TNF-α, and RANTES, the latter of which can be produced by T-cells in response to TNF-α and IL-1-α, IL-1a and TNF-α, inflammatory cytokines that have been targeted successfully in the treatment of JIA, rheumatoid arthritis, and other autoimmune diseases (Nash, P. T. & Florin, T. H. Tumour necrosis factor inhibitors. *Med J Aust* 183, 205-208, doi:nas10250_fm [pii] (2005), Lovell, D. J., Bowyer, S. L. & Solinger, A. M. Interleukin-1 blockade by anakinra improves clinical symptoms in patients with neonatal-onset multisystem inflammatory disease. *Arthritis Rheum* 52, 1283-1286, doi:10.1002/art.20953 (2005) are produced in greater abundance in WT as compared to DEK-KO mice. The lower levels of IL-12p40, IL-12p70, and IL-23 in the joints of DEK-KO vs. DEK WT mice injected with zymosan indicates that DEK has an effect on T-cell response.

These results demonstrate that DEK regulates the production of both inflammatory cytokines and NETs. (Keshari, R. S. et al. Cytokines induced neutrophil extracellular traps formation: implication for the inflammatory disease condition. *PLoS One* 7, e48111, doi:10.1371/journal.pone.0048111 (2012).)

These results demonstrate that depletion of DEK confers protection against arthrities in a murine model of inflammatory arthrities with reduced levels of pro-inflammatory cytokines in the knees of DEK-KO mice.

Example 14

This example describes immunohistochemistry in sections of mouse joints.

Frozen sections of mouse joints were thawed rapidly and then fixed in 2% paraformaldehyde/PBS (pH=7.4) for 12 min at room temperature. Sections were washed twice for 2 min in PBS, and then permeabilized in 0.05% Triton X-100 in PBS for 10 min at room temperature. Sections were washed with PBS 3 times for 5 min each, followed by blocking with 10% normal goat serum overnight at 4° C. Sections were probed with rabbit anti-MPO (Dako Denmark A0398) at dilution of 1:500, rat anti-Ly6C/Ly6G antibody (BD Pharmingen 550327) at a dilution of 1:20 for 3 hours at room temperature, or with custom-made rabbit anti-DEK antibody diluted in 10% normal goat serum at a dilutions of 1:50, 1:100, or 1:200 overnight at 4° C. After washing in PBS for 5 min×3, sections were incubated with secondary antibody; goat anti-rat IgG-AlexaFluor 594 (Invitrogen A-11007), at 1:200 for Ly6C/Ly6G or goat anti-rabbit IgG-AlexaFluor 594 (Invitrogen A-11037) at 1:200 for DEK. Antibodies were diluted in 10% normal goat serum; sections were incubated for 45 min at room temperature.

Figure 17A:
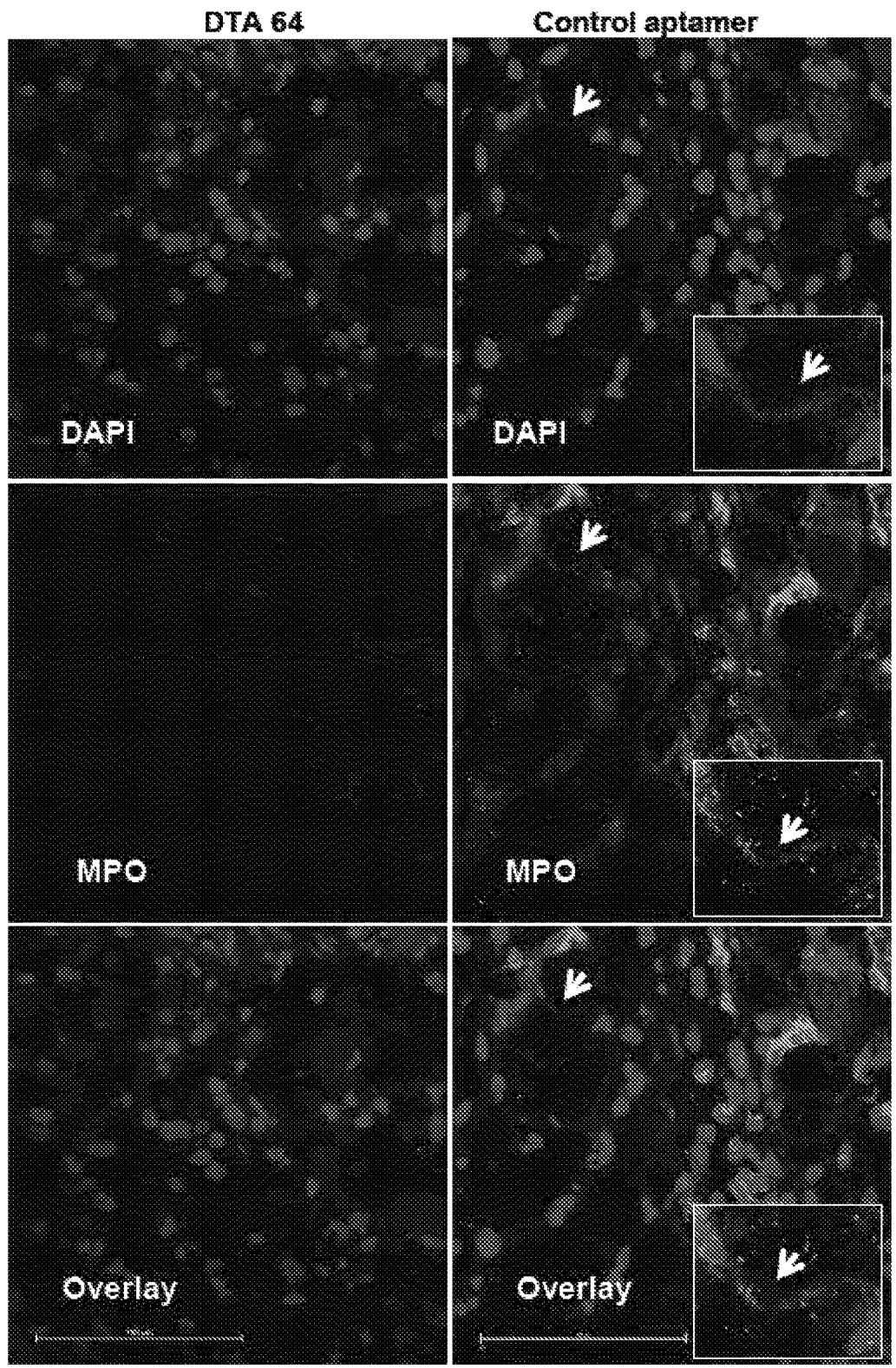
FIG. 17: Shows immunostaining of non-permeabilized sections of knees from mice treated with SEQ ID NO: 6 compared to control aptamer, and the presence of extracellular DNA colocalizing with MPO, in keeping with the presence of NETs in joints injected with zymosan and treated with control aptamer control, but not with the anti-DEK aptamer.
Figure 17B:
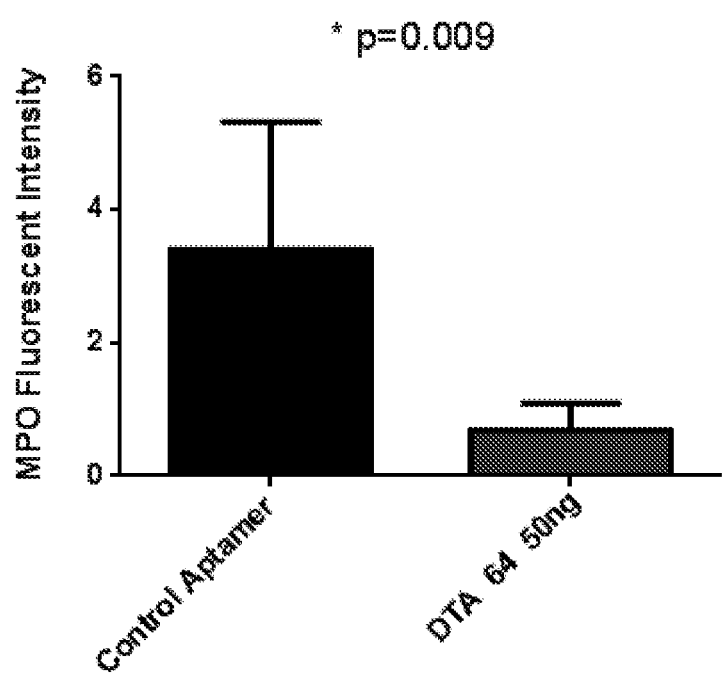
Figure 17C:
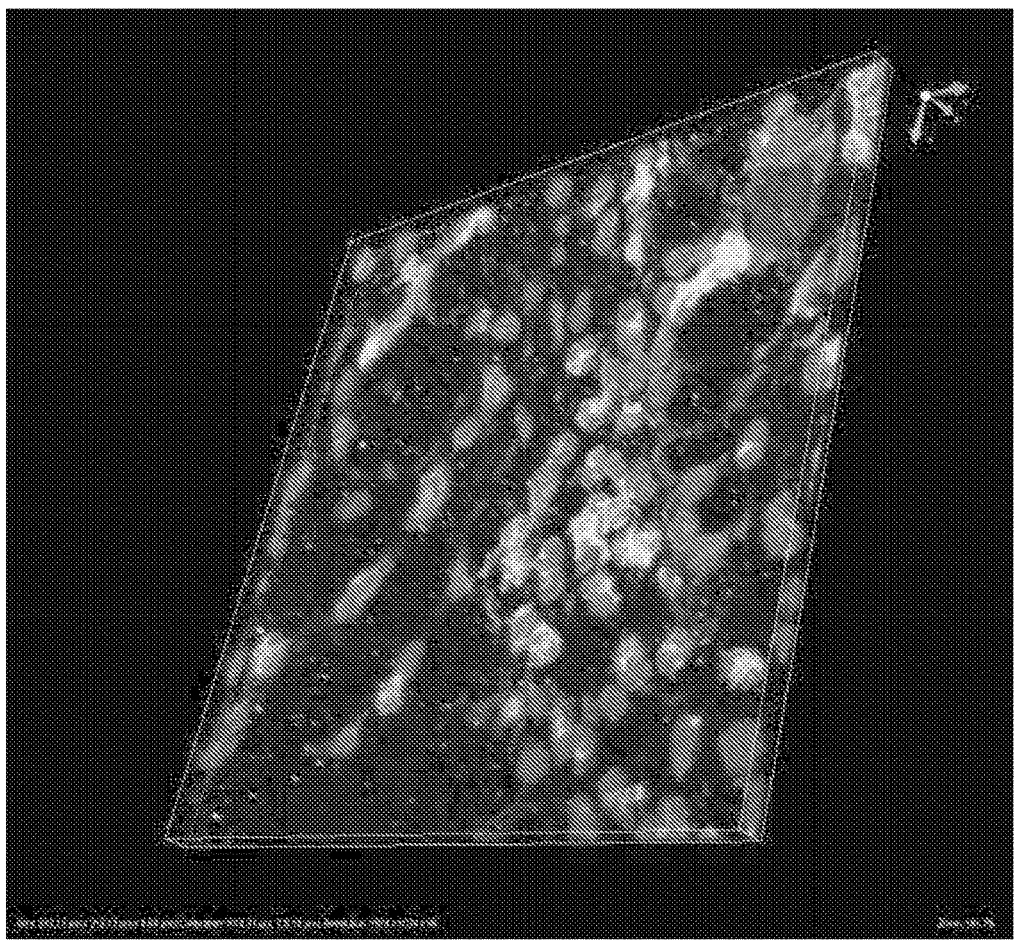

Immunostaining of non-permeabilized sections of the knees from mice treated with SEQ ID NO: 6 compared to control aptamer for myeloperoxidase (MPO), a known marker of NETs, revealed a reduction in staining (FIG. 17A and FIG. 17B). Co-localization of MPO and extracellular DAPI staining further indicates that the reduction in MPO staining reflects a reduction in extracellular NETs in the SEQ ID NO: 6-treated mice. Combining all the Z-stacks to a 3-D imaging of the knee section further demonstrates the presence of extracellular DNA colocalizing with MPO, supporting the presence of NETs in joints injected with zymosan and treated with control aptamer control, but not with the anti-DEK aptamer (FIG. 17C).

Example 15

This example describes DEK protein in synovial fluid (SF) of patients with juvenile idiopathic arthritis (JIA).

SFs were obtained from JIA patients during therapeutic arthrocentesis by medical staff of the Pediatric Rheumatology division at the University of Michigan. SFs were diluted 1:1 with PBS followed by separation on Histopaque-1077.

Neutrophils were plated on cover slips as described above without additional stimulation. Neutrophils were purified from synovial fluids (SFs) and subjected to immunohistochemical analysis using monoclonal anti-DEK antibody (FIG. 5C, bottom).

Neutrophils purified from SFs of JIA patients are significantly activated, such that they form NETs without stimulation. The NETs demonstrated positive DEK staining, and significant co-localization of DEK with elastase, LL-37, and DNA (stained by Hoechst). Affinity-purified DEK autoantibodies isolated from the SFs of JIA patients that show specific recognition of DEK (Ng, E. W. et al. Pegaptanib, a targeted anti-VEGF aptamer for ocular vascular disease. *Nat Rev Drug Discov* 5, 123-132, doi:10.1038/nrd1955 (2006.) recognized NETs formed by synovial neutrophils (FIG. 5D).

Example 16

This example describes purification of DEK antibodies from human synovial fluid (SF).

SulfoLink Coupling Gel (Pierce Biotechnology, Rockford, Ill., USA) was used to couple the recombinant human DEK protein and purify DEK antibodies. 100 μg of the DEK protein was dissolved in 500 μl of coupling buffer [(1×NET buffer: 50 mM Tris, 150 mM NaCl, 5 mM EDTA, pH 8.5)] coupled to 500 μl of washed SulfoLink gel (in a 10 ml chromatography column) by mixing with the resin for 20 min followed by 40 min incubation. Non-specific binding sites were blocked with 50 mM cysteine by mixing for 15 min followed by 30 min incubation. The column was washed with 16× column volume of 1 M NaCl followed by another wash with distilled water. The column was equilibrated with 1×NET buffer prior to the affinity purification step. All steps were performed at room temperature.

Human synovial fluids were adjusted to 10 mM Tris, pH 8.0 and centrifuged to remove any precipitates. A total of 3 to 5 ml of synovial fluids was used to purify DEK antibodies on the prepared column. The column was mixed and then rotated for at least 4 h (up to 16 hours) at room temperature. The column was washed with 10× column volume of 1×NET buffer+0.5 M NaCl+0.5% NP-40 followed by a wash with 1×NET buffer+0.5% NP-40, another wash of 1×NET buffer and a final wash of 0.1×NET buffer. Antibody was eluted with 0.1 M glycine (pH 3.0) and neutralized with 1M Tris (pH 8.0). The antibodies are highly specific for recombinant DEK (Ng, E. W. et al. Pegaptanib, a targeted anti-VEGF aptamer for ocular vascular disease. *Nat Rev Drug Discov* 5, 123-132, doi:10.1038/nrd1955 (2006).

These results demonstrate that NETs are formed spontaneously bye JIA synovial neutrophils.

Example 17

This example describes extracellular and intracellular DEK.

Figure 18A:
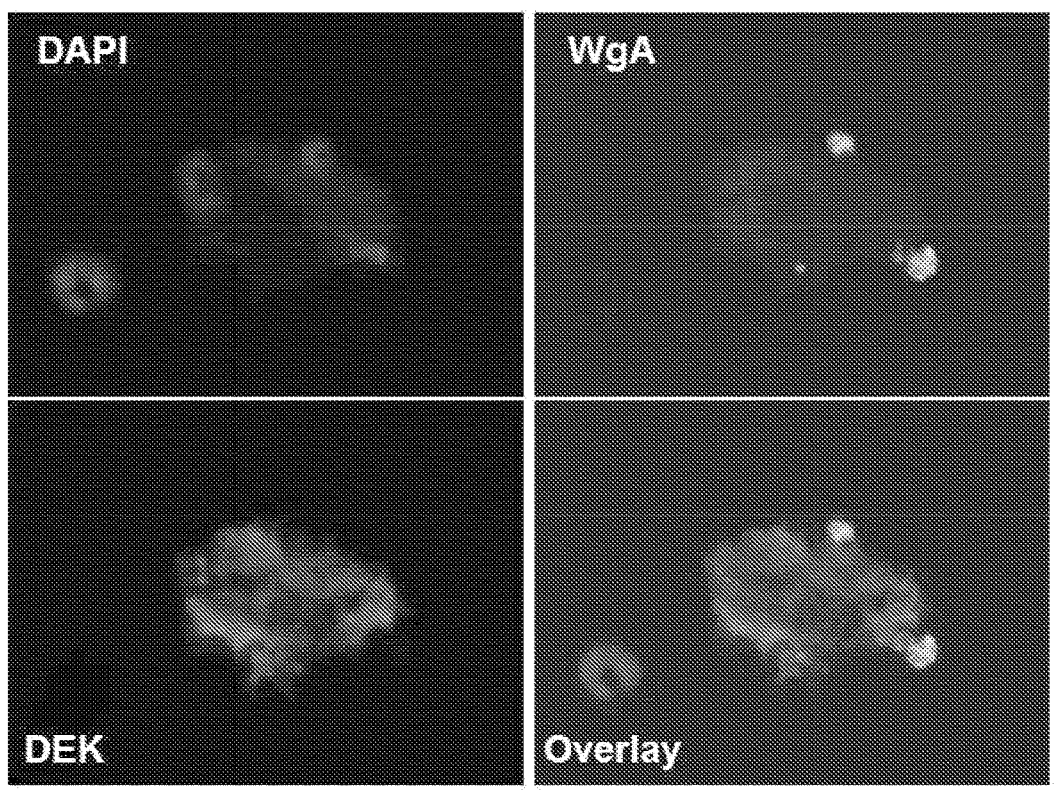
FIG. 18: Shows that DEK is present with NETs in the extracellular space of DEK-KO neutrophils.
Figure 18B:
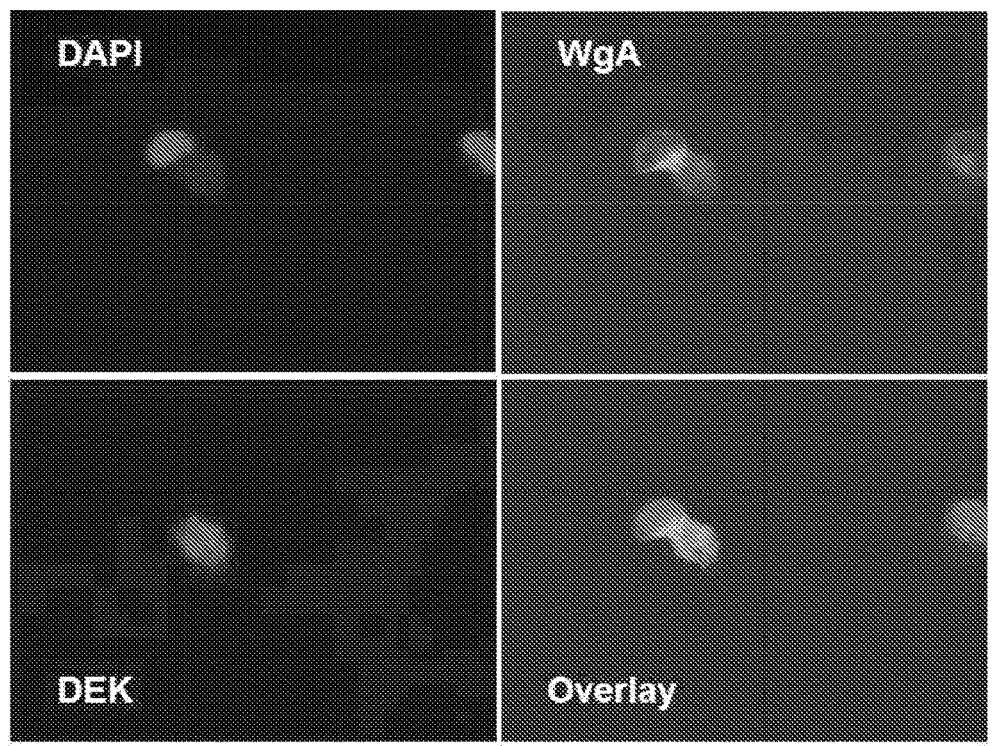
Figure 18C:
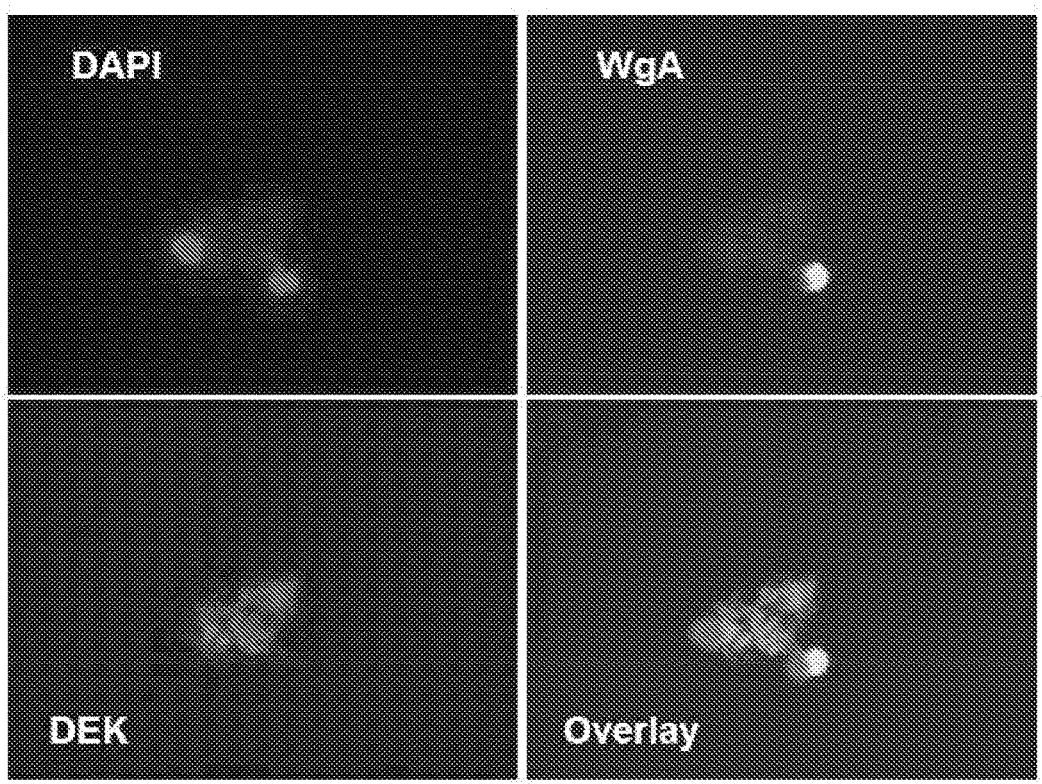
Figure 19:
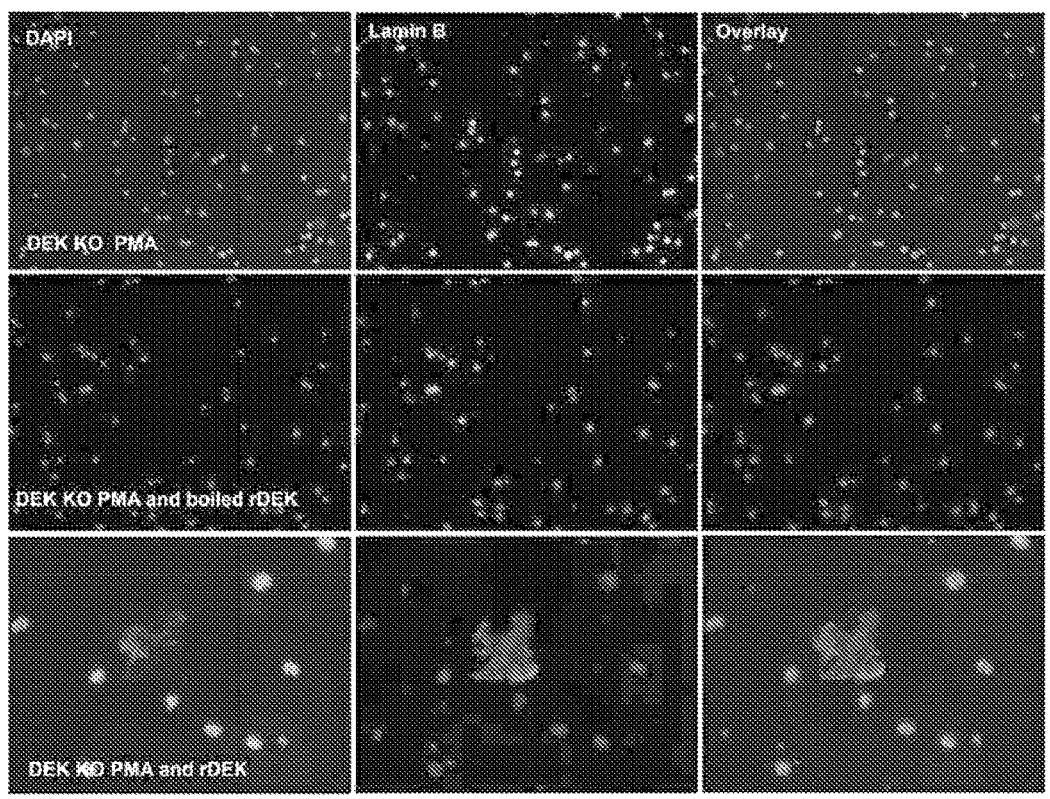
FIG. 19: Shows that bioactive DEK needed to restore NEY formation by DEK-KO neutrophils.

DEK participates in global heterochromatin integrity within the nucleus (Kappes, F. et al. The DEK oncoprotein is a Su(var) that is essential to heterochromatin integrity. *Genes Dev* 25, 673-678, doi:10.1101/gad.2036411 25/7/673 [pii] (2011).) Since NETs are chromatin-containing structures, DEK may affect chromatin structure and hence NET formation by one of two basic mechanisms: (1) DEK is known to modulate intranuclear chromatin structure, and in a number of different cell types recombinant DEK is taken up by cells and can go directly to the nucleus and affect chromatin structure and cell function (Saha, A. K. et al. Intercellular trafficking of the nuclear oncoprotein DEK. *Proc Natl Acad Sci USA* 110, 6847-6852, doi:10.1073/pnas.1220751110 1220751110 [pii] (2013).), in this capacity, DEK may participate in the early events of NET formation; (2) DEK may affect NET formation in the cytoplasm or extracellular space. To test if extracellular rDEK enters the nucleus of DEK-KO neutrophils to restore NET formation, recombinant DEK was added and the nuclear envelope was stained with Lamin B. As shown in FIG. 11E, recombinant DEK does not enter the nucleus of the neutrophil, but associates with the NET structures. In addition, the cell was stained with wheat germ agglutinin (WGA), a cytoplasm marker, and again recombinant DEK added to neutrophils does not enter the cell, and is found primarily mainly in the extracellular space (FIG. 18). FIG. 18 shows DEK-KO neutrophils treated with recombinant DEK prior to PMA stimulation. Cells were fixed at FIG. 18A 2 hours, FIG. 18B 3 hours and FIG. 18C 4 hours of PMA treatment, and then permeabilized and stained for DEK and wheat germ agglutinin (WGA), a cytoplasm marker. DEK is detected outside of the cell in the NETs. Accordingly, DEK does not promote NET formation from within the cell, but acts as a component of NET architecture in the extracellular space. Denaturation of recombinant DEK protein prior to addition to DEK-KO neutrophils prevented restoration of NET formation (FIG. 19). FIG. 19 shows that bioactive DEK is needed to restore NET formation by DEK-KO neutrophils. DEK-KO neutrophils were treated with boiled recombinant DEK (middle panel) or native recombinant DEK (lower panel) prior to PMA stimulation. Cells were fixed and stained for DEK and Lamin B. NETs were observed only with the native recombinant DEK, further confirming the specific role of biologically competent DEK in NET biology. In aggregate, these findings indicate that bioactive DEK plays a central role in NET formation through its effects on the extracellular chromatin component of these structures. These results indicate that neutrophils release DEK into the extracellular space, and that DEK participates in extracellular structures that regulate innate immunity and generation of autoantibodies.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

INCORPORATION BY REFERENCE

All publications, published patent documents, and patent applications cited herein are hereby incorporated by reference to the same extent as though each individual publication, published patent document, or patent application was specifically and individually indicated as being incorporated by reference.

We claim:

1. A method of treating or ameliorating an inflammatory condition in a patient, comprising administering to said patient a therapeutically effective amount of a single-stranded anti-DEK DNA aptamer, and a pharmaceutically acceptable carrier, wherein said anti-DEK DNA aptamer is SEQ ID NO:1, SEQ ID NO: 2 or SEQ ID NO:6.

2. The method of claim 1, wherein said inflammatory condition is one or more conditions selected from arthritis, rheumatoid arthritis, juvenile rheumatoid arthritis, and inflammatory disease or an autoimmune disease.

3. The method of claim 1, wherein said patient is a human patient and the DEK is human DEK.

4. The method of claim 1, further comprising administering to said patient one or more anti-inflammatory agents.

5. A kit comprising a pharmaceutical composition comprising a therapeutically effective amount of a single-stranded anti-DEK DNA aptamer, wherein said anti-DEK DNA aptamer is SEQ ID NO:1, SEQ ID NO: 2 or SEQ ID NO:6, optionally one or more anti-inflammatory agents, and instructions for administering said pharmaceutical composition to a patient diagnosed with arthritis, rheumatoid arthritis, juvenile rheumatoid arthritis, or uveitis.

6. A composition comprising a therapeutically effective amount of a single-stranded anti-DEK DNA aptamer that specifically binds to DEK, wherein said anti-DEK DNA aptamer is SEQ ID NO:1, SEQ ID NO: 2 or SEQ ID NO:6.

* * * * *

UNITED STATES PATENT AND TRADEMARK OFFICE
CERTIFICATE OF CORRECTION

PATENT NO. : 10,138,486 B2
APPLICATION NO. : 15/557757
DATED : November 27, 2018
INVENTOR(S) : David Markovitz et al.

It is certified that error appears in the above-identified patent and that said Letters Patent is hereby corrected as shown below:

In the Specification

In the STATEMENT REGARDING FEDERALLY SPONSORED RESEARCH OR DEVELOPMENT section, Column 1, Line 14 reads:
"This invention was made with government support under R01 AI062248, R01 AI062248, R03 AR056748-01, and K01 AR055620 awarded by the National Institute of Health. The government has certain rights in the invention."

Whereas it should read:
"This invention was made with government support under AR056748, AR055620, and AI087128 awarded by the National Institutes of Health. The government has certain rights in the invention."

Signed and Sealed this
Nineteenth Day of February, 2019

Andrei Iancu
*Director of the United States Patent and Trademark Office*